(12) United States Patent
Menchen et al.

(10) Patent No.: US 8,058,414 B2
(45) Date of Patent: Nov. 15, 2011

(54) UNNATURAL POLYMERASE SUBSTRATES THAT CAN SUSTAIN ENZYMATIC SYNTHESIS OF DOUBLE STRANDED NUCLEIC ACIDS FROM A NUCLEIC ACID TEMPLATE AND METHODS OF USE

(75) Inventors: Steven Menchen, Fremont, CA (US); Barnett Rosenblum, San Jose, CA (US); Paul Kenney, Sunnyvale, CA (US); Shoeb Khan, Foster City, CA (US); Zhaochun Ma, Sunnyvale, CA (US); Jer-Kang Chen, Palo Alto, CA (US); Joe Y. Lam, Castro Valley, CA (US); Boli Huang, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/355,487

(22) Filed: Jan. 16, 2009

(65) Prior Publication Data

US 2009/0269759 A1    Oct. 29, 2009

Related U.S. Application Data

(60) Provisional application No. 61/048,808, filed on Apr. 29, 2008, provisional application No. 61/136,732, filed on Sep. 29, 2008.

(51) Int. Cl.
*C07G 3/00* (2006.01)
*C07H 21/02* (2006.01)
*C07H 21/04* (2006.01)
*C07H 19/04* (2006.01)
*C12Q 1/68* (2006.01)
*C12P 19/34* (2006.01)

(52) U.S. Cl. .... 536/4.1; 536/23.1; 536/24.3; 536/24.33; 536/26.6; 435/6; 435/91.1

(58) Field of Classification Search ............... 536/4.1, 536/23.1, 24.3, 24.33, 26.6; 435/6, 91.1
See application file for complete search history.

(56) References Cited

U.S. PATENT DOCUMENTS 6,664,079 B2   12/2003   Ju et al.
(Continued)

FOREIGN PATENT DOCUMENTS

WO          00/36152 A       6/2000
(Continued)

OTHER PUBLICATIONS

Mitra, et al., "Fluorescent in situ sequencing on polymerase colonies," Analytical Biochemistry, vol. 320 (1), pp. 55-65 (2003).

(Continued)

*Primary Examiner* — Jezia Riley

(57) ABSTRACT

Nucleotide analogs that can sustain the enzymatic synthesis of double-stranded nucleic acid from a nucleic template are described. The nucleotide analogs include: (i) a base selected from the group consisting of adenine, guanine, cytosine, thymine, uracil and their analogs; (ii) a label attached to the base or analog of the base via a cleavable linker; (iii) a deoxyribose; and (iv) one or more phosphate groups. The linker and/or the label inhibits template directed polymerase incorporation of a further nucleotide substrate onto an extended primer strand. In addition, cleavage of the linker leaves a residue attached to the base which is not present in the natural nucleotide and which does not inhibit extension of the primer strand. The nucleotide analogs can therefore be used as reversible terminators in sequencing by synthesis methods without blocking the 3' hydroxyl group. Methods of sequencing DNA using the substrates are also described.

25 Claims, 50 Drawing Sheets

U.S. PATENT DOCUMENTS

| | | | |
|---|---|---|---|
| 6,811,979 B2 * | 11/2004 | Taing et al. ................ 435/6 |
| 7,345,159 B2 | 3/2008 | Ju et al. | |
| 2007/0117103 A1 | 5/2007 | Buzby | |
| 2008/0003571 A1 | 1/2008 | McKernan et al. | |
| 2009/0062129 A1 | 3/2009 | McKernan et al. | |

FOREIGN PATENT DOCUMENTS

| | | |
|---|---|---|
| WO | 2004018493 A1 | 4/2004 |
| WO | 2007010251 A2 | 1/2007 |
| WO | 2007010254 A1 | 1/2007 |
| WO | WO-2009/134469 | 11/2009 |

OTHER PUBLICATIONS

Nakane, et al., "Nanopore sensors for nucleic acid analysis," Condens. Matter 15 (32), R1365-1393 (2003).

Levene, et al., "Zero-mode waveguides for single-molecule analysis at high concentrations," Science 299 (5607), pp. 682-686 (2003).

Braslavsky, et al., "Sequence information can be obtained from single DNA molecules," PNAS 100 (7), pp. 3960-3964 (2003).

Ju, et al., "Four color DNA sequencing by synthesis using cleavable fluorescent nucleotide reversible terminators," PNAS, vol. 35 (52), pp. 19635-19640 (2006).

Wu, et al., "Termination of DNA synthesis by N6-alkylated, not 3'-O-alkylated, photo-cleavable 2'-deoxyadenosine triphosphates," Nucleic Acids Research, 35 (19), pp. 6339-6349 (2007).

Wu, et al., "3'-O-modified nucleotides as reversible terminators for pyrosequencing," PNAS, 104 (42), pp. 16462-16467 (2007).

Ju, et al., "Four-color DNA sequencing by synthesis using cleavable fluorescent nucleotide reversible terminators," Proceedings of the National Academy of Sciences of USA, vol. 103, No. 52, pp. 19635-19640 (2006).

Li, et al., "A photocleavable fluorescent nucleotide for DNA sequencing and analysis," Proceedings of the National Academy of Sciences of USA, vol. 100, No. 2, pp. 414-419 (2003).

PCTUS2009031297, International Search Report mailed May 8, 2009.

US09/31297 International Preliminary Report on Patentability and Written Opinion Mailed Nov. 11, 2010.

* cited by examiner

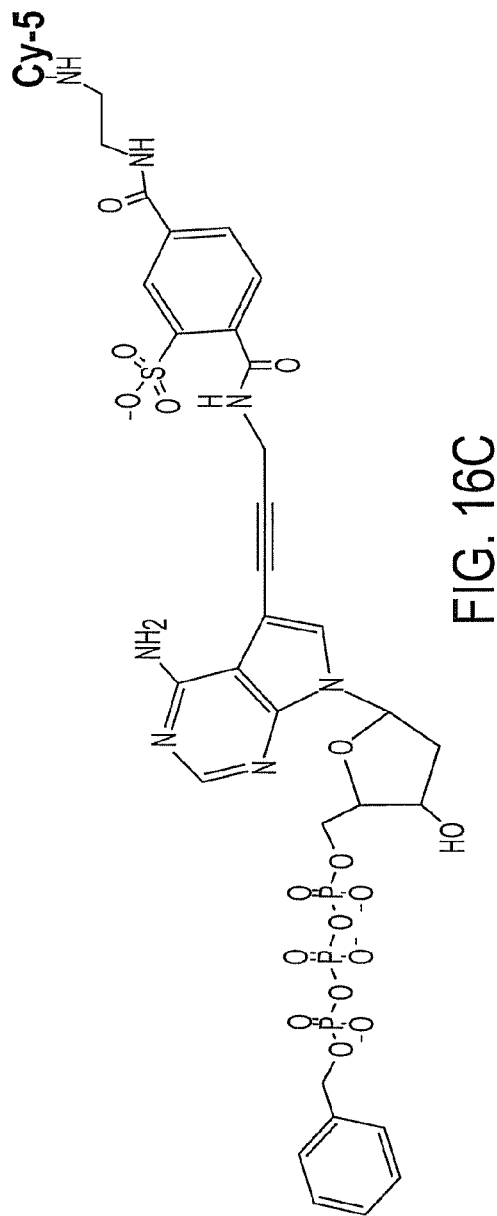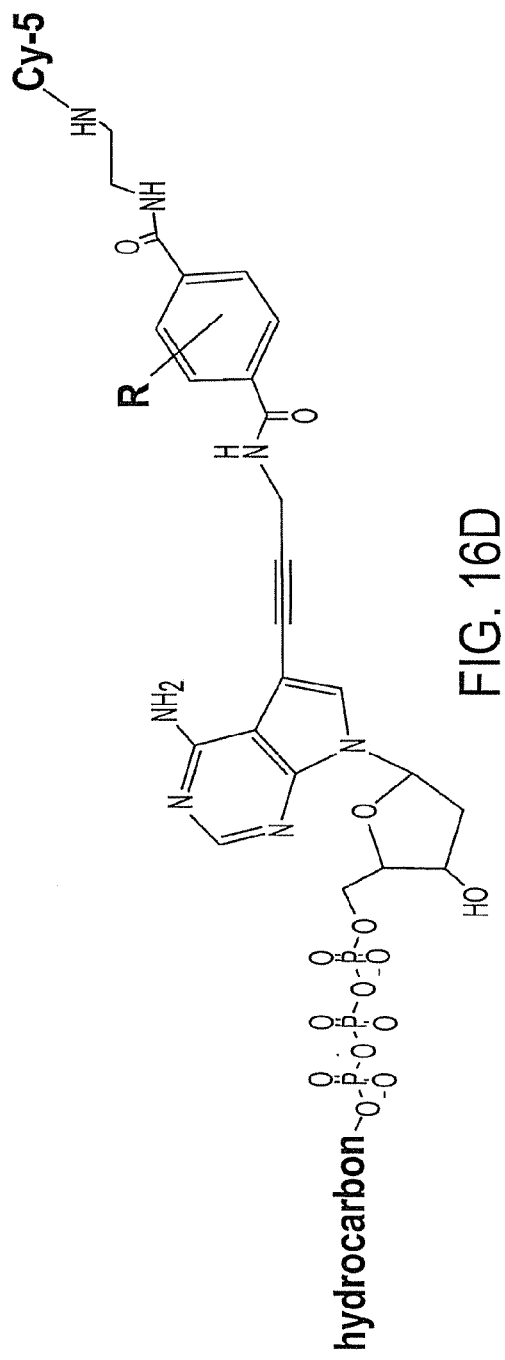
FIG. 16C
FIG. 16D

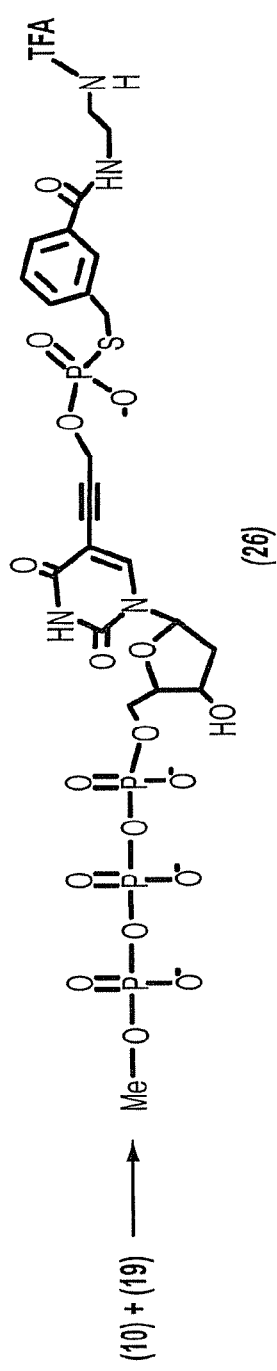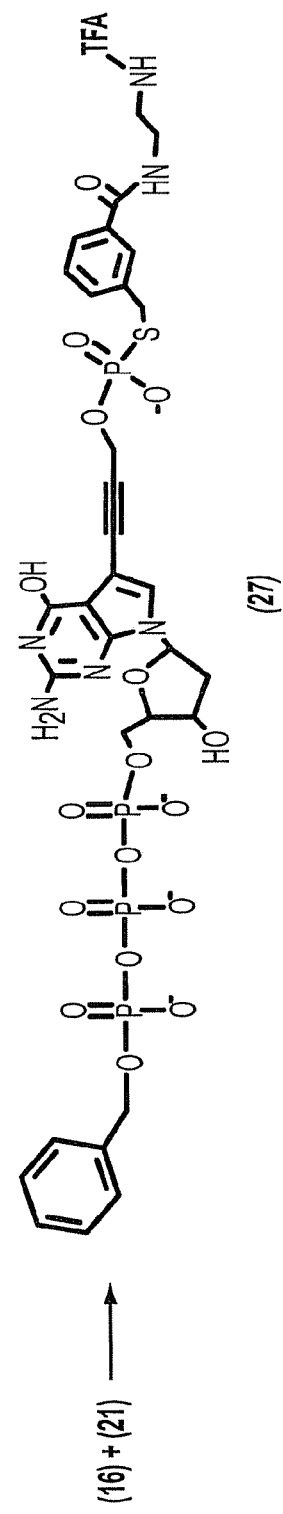
FIG. 32
FIG. 33

(12) + (25)

(16) + (25)

```
                              SEQUENCE LISTING

<160> NUMBER OF SEQ ID NOS: 26

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aagaagaaga agaagaagaa gaagaagaag aagaagaaga ag                            42

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtgactggc cgtcgtttac a                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctgtactggc cgtcgtttac a                                                  21

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 cccccgtgt gtgctaaact ggccgtcgtt ttaca                                    35

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=g, c or t

<400> SEQUENCE: 5 cccccgtgt gtgctanact ggccgtcgtt ttaca                                    35
```

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtaaaacga cggccagt                                                       18

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 7 cccccgtgt gtgcttnact ggccgtcgtt ttaca                                     35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 8 cccccgtgt gtgctnnact ggccgtcgtt ttaca                                     35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 9 cccccgtgt gtgctntact ggccgtcgtt ttaca                                     35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 10 cccccgtgt gtgctncact ggccgtcgtt ttaca                                     35
```

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 11 cccccccgtgt gtgctngact ggccgtcgtt ttaca                              35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: n=a, c, g or t/u, unknown, or other

<400> SEQUENCE: 12 cccccccgtgt gtgctnaact ggccgtcgtt ttaca                              35

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 cccccccgtgt gtgcttaact ggccgtcgtt ttaca                              35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 cccccccgtgt gtgctatact ggccgtcgtt ttaca                              35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 cccccccgtgt gtgctagact ggccgtcgtt ttaca                              35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic

```
oligonucleotide

<400> SEQUENCE: 16 cccccccgtgt gtgctttact ggccgtcgtt ttaca                              35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 cccccccgtgt gtgcttgact ggccgtcgtt ttaca                              35

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 cccccccgtgt gtgcttcact ggccgtcgtt ttaca                              35

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 cccccccgtgt gtgctcgact ggccgtcgtt ttaca                              35

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 cccccccgtgt gtgctggact ggccgtcgtt ttaca                              35

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 cccccccgtgt gtgctgaact ggccgtcgtt ttaca                              35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22 cccccgtgt gtgctgtact ggccgtcgtt ttaca                         35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 cccccgtgt gtgctgcact ggccgtcgtt ttaca                         35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 cccccgtgt gtgctccact ggccgtcgtt ttaca                         35

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 cccccgtgt gtgctcaact ggccgtcgtt ttaca                         35

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 cccccgtgt gtgctctact ggccgtcgtt ttaca                         35
```

UNNATURAL POLYMERASE SUBSTRATES THAT CAN SUSTAIN ENZYMATIC SYNTHESIS OF DOUBLE STRANDED NUCLEIC ACIDS FROM A NUCLEIC ACID TEMPLATE AND METHODS OF USE This application claims the benefit of Provisional U.S. Patent Application Ser. No. 61/048,808, filed on Apr. 29, 2008 and Provisional U.S. Patent Application Ser. No. 61/136,732, filed on Sep. 29, 2008. Each of the aforementioned applications is incorporated by reference herein in its entirety.

Pursuant to the provisions of 37 C.F.R. §1.52(e)(5), the sequence listing text file named 68523_Seq_Listing.txt, created on Jan. 16, 2009 and having a size of 7,129 bytes, and which is being submitted herewith, is incorporated by reference herein in its entirety.

The section headings used herein are for organizational purposes only and should not be construed as limiting the subject matter described herein in any way.

FIELD

This application relates generally to polymerase substrates and to methods of sequencing nucleic acids such as DNA or RNA using the substrates.

INTRODUCTION

Nucleic acid sequencing typically involves cloning the nucleic acid of interest to prepare bulk samples of defined nucleic acid fragments followed by analysis of the bulk nucleic acids. Sequencing by synthesis has been proposed as a method to achieve fast de novo sequencing. Sequencing by synthesis can involve the analysis of an ensemble of amplified single molecules of nucleic acid, or the analysis of single molecules of nucleic acid and can theoretically be used to examine native genomic DNA without the need for bacterial cloning or other forms of amplification.

There still exists a need, however, for improved methods of sequencing by synthesis and single molecule nucleic acid sequencing.

SUMMARY

A compound represented by the following formula (I) is provided:

(I)

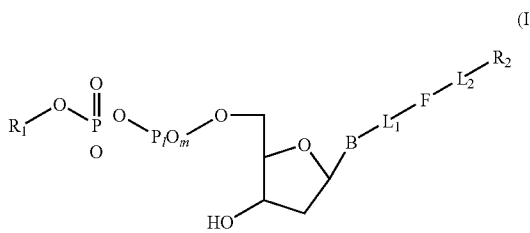

wherein:

B is a base selected from the group consisting of adenine, guanine, cytosine, uracil, thymine, or their respective analogs;

$L_1$ is a group that forms a linkage between the base B and F;

F is a heteroatom that forms a linkage between $L_1$ and $L_2$;

$L_2$ is a chemically labile group with respect to its attachment to F and forms a chemical linkage to $R_2$;

$L_3$ is either H or a chemically labile group comprising a heteroatom which forms a chemical linkage to $R_2$;

each $R_2$ is, independently, a group comprising a reporter;

$R_1$ is a substituent (e.g., a reporter or quencher at the terminus of the polyphosphate) that suppresses the template directed polymerase incorporation rate of the nucleoside triphosphate onto the 3' end of an extending oligonucleotide prior to cleavage of $L_2$-$R_2$ from the previous incorporation event;

$L_2$-$R_2$ prevents the template directed polymerase incorporation of the compound of the formula (I) onto the 3' end of an extending oligonucleotide onto which a compound of the formula (I) has been incorporated;

l is an integer; and m=3l−1.

A compound which has a structure represented by the following formula (II) is also provided:

(II)

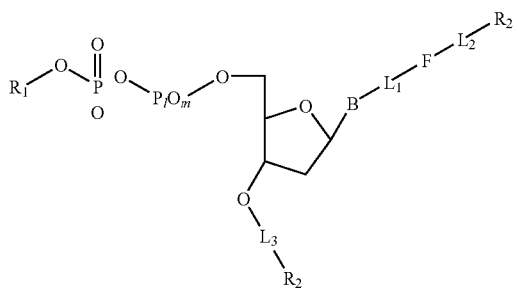

wherein B, $R_1$, $L_1$, F, $L_2$, $R_2$, l and m are defined as set forth above for formula (I).

A method of sequencing a nucleic acid is also provided which comprises:

(a) hybridizing a primer to a target polynucleotide to form a primer-target duplex, wherein the target polynucleotide is attached to a solid support at the 3' or 5' end of the target polynucleotide;

(b) contacting the primer-target duplex with a polymerase and one or more nucleotide analogs to incorporate a nucleotide analog onto the 3' end of the primer thereby forming an extended primer strand, wherein the incorporated nucleotide analog terminates the polymerase reaction and wherein each of the one or more nucleotide analogs comprises: (i) a base selected from the group consisting of adenine, guanine, cytosine, thymine, uracil and their analogs; (ii) a label attached to the base or analog thereof via a cleavable linker; (iii) a deoxyribose; and (iv) one or more phosphate groups, wherein the label is unique for the base and wherein the combination of the polyphosphate terminal substituent, the linker and/or the label inhibits the template directed polymerase incorporation of a further nucleotide analog onto the extended primer strand;

(c) washing the surface of the solid support to remove unincorporated nucleotide analogs;

(d) detecting the unique label attached to the just-incorporated nucleotide analog to thereby identify the just-incorporated nucleotide analog;

(e) cleaving the cleavable linker between the just incorporated nucleotide analog and the unique label thereby allowing the incorporation of a further nucleotide analog onto the extended primer strand;

(f) washing the surface of the solid support to remove cleaved compound fragments; and (e) repeating steps (b), (c), (d), (e) and (f).

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way. The patent or application file contains at least one drawing executed in color. Copies of this patent or patent application publication with color drawing(s) will be provided by the Office upon request and payment of the necessary fee.

FIG. 6 is a schematic illustrating the use of a reversible terminator having a free 3'-hydroxyl group showing cleavage of the reporter from the incorporated reversible terminator on the end of the strand followed by incorporation of another reversible terminator to the end of the strand wherein:

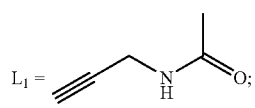

F=An oxygen atom;

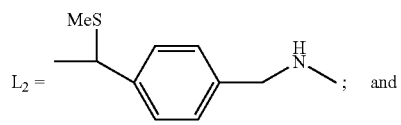

$R_2$=Dye.

Figure 7:
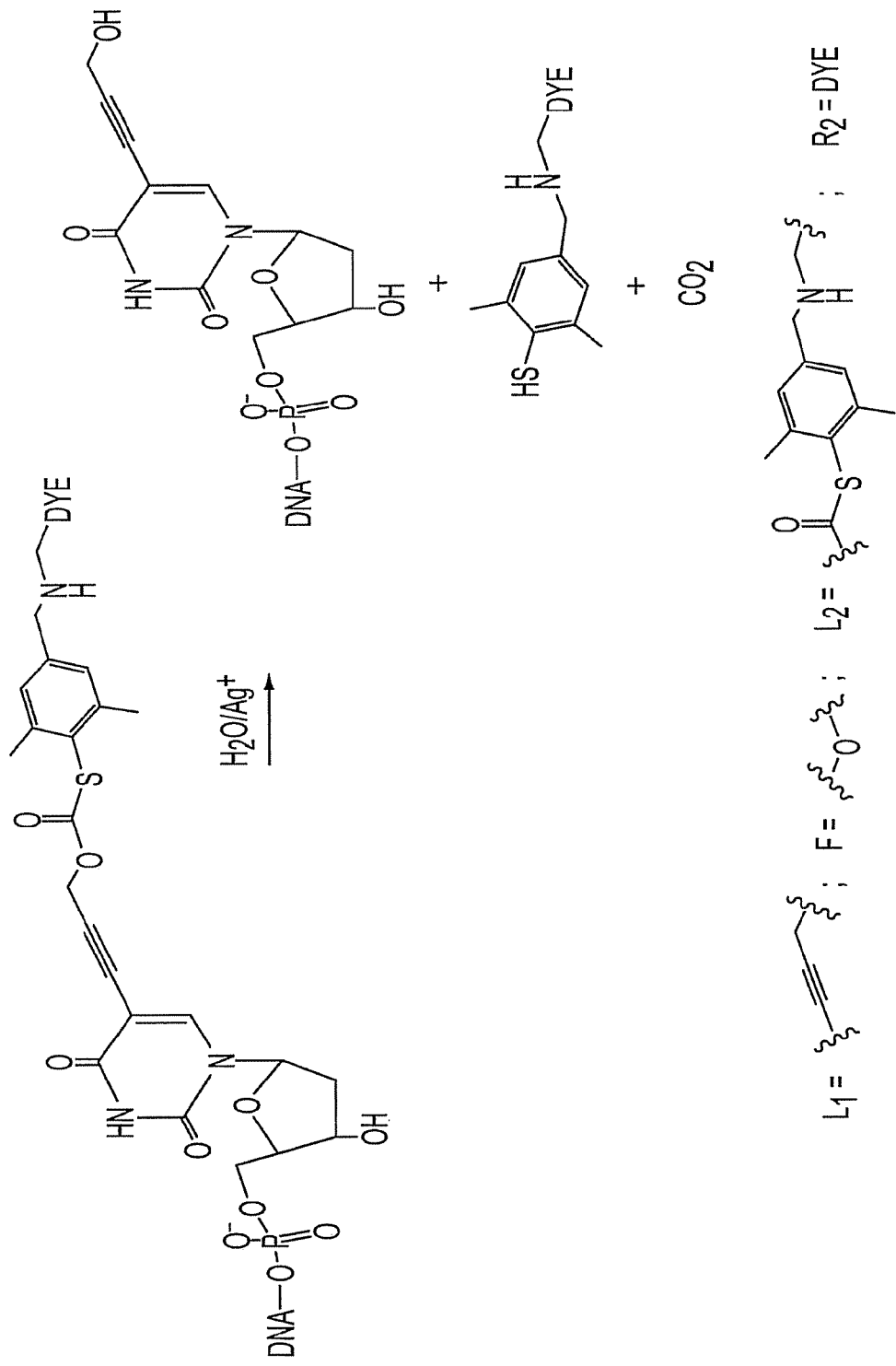

FIG. 7 is a schematic showing the structure of a first reversible terminator having a silver ion cleavable linker and illustrating the chemistry involved with silver ion chemical cleavage.

Figure 8:
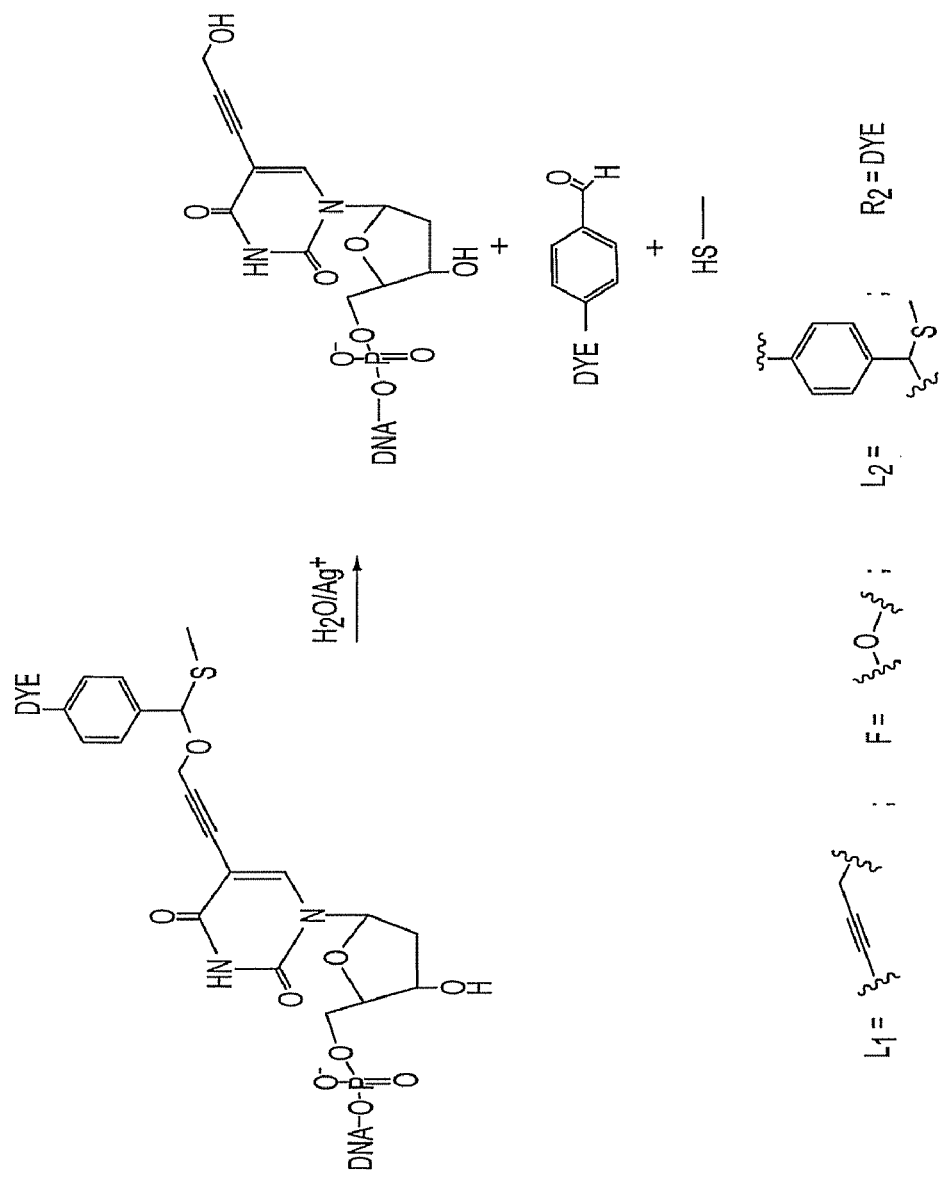
Figure 9A:
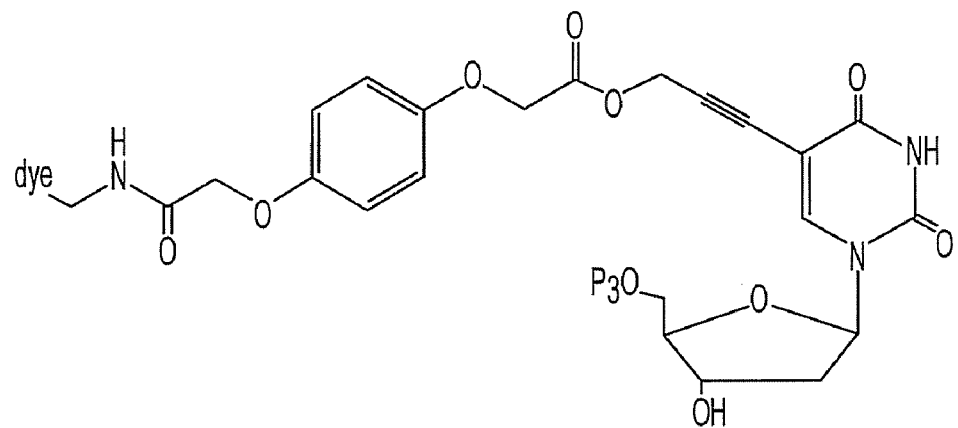
Figure 9B:
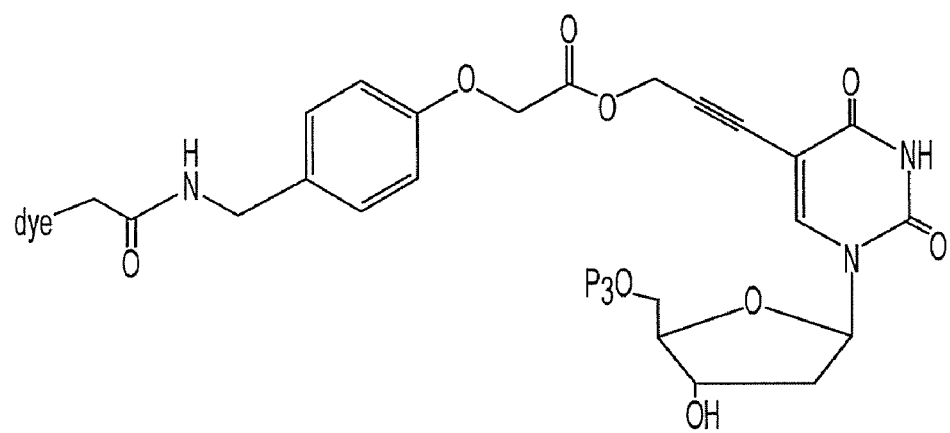
Figure 9C:
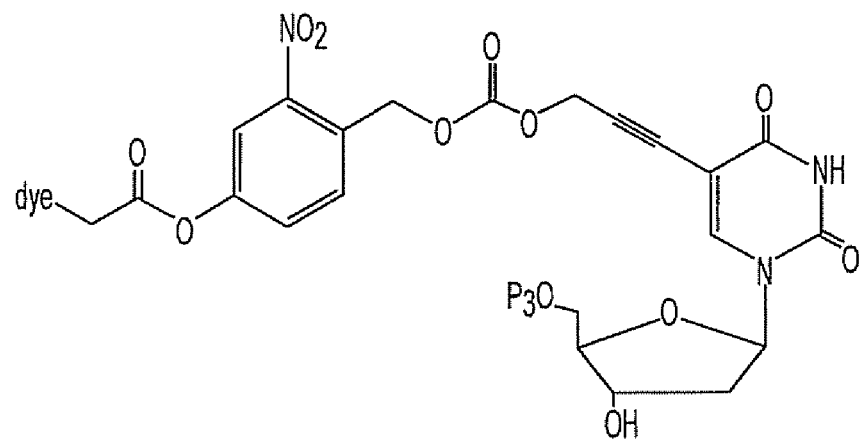
Figure 9D:
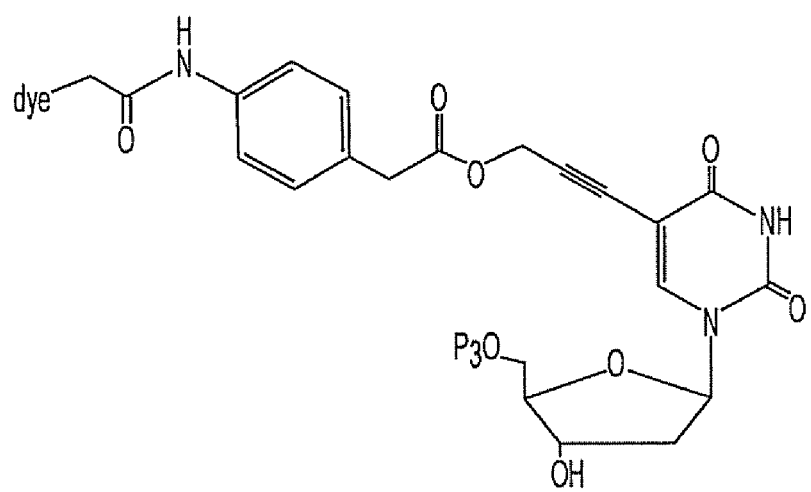
Figure 10A:
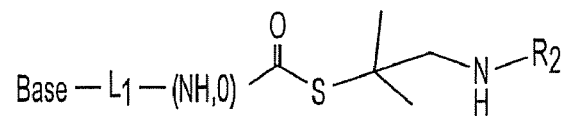
Figure 10B:
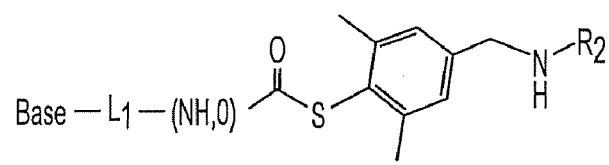
Figure 10C:
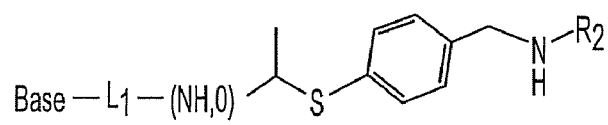
Figure 10D:
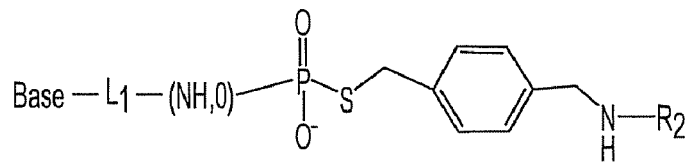

FIG. 8 is a schematic showing the structure of a second reversible terminator having a silver ion cleavable linker and illustrating the chemistry involved with silver ion chemical cleavage.

FIGS. 9A-9D are schematics illustrating the structure of reversible terminators having linkers between the base and the reporter that can be cleaved by a basic compound such as ammonia.

FIGS. 10A-10D are schematics illustrating the structure of silver ion cleavable linkers that can be cleaved in a single silver ion step or in multiple steps comprising silver ions to yield hydroxyl or amino groups at the terminal end of the linker residue.

Figure 11:
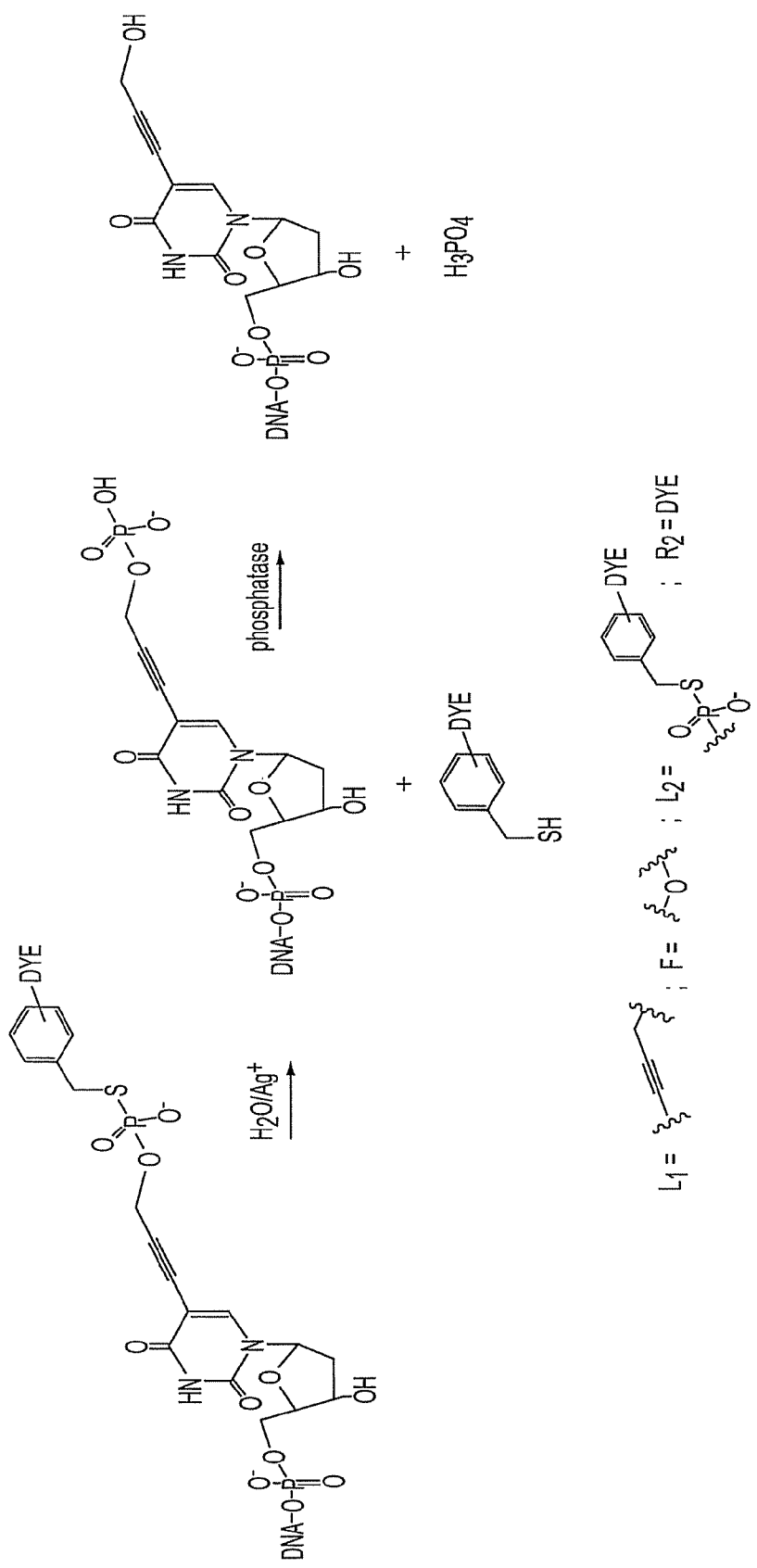

FIG. 11 is a schematic illustrating the use of silver ion cleavable groups which leave a phosphate terminal group on the residue.

Figure 12:
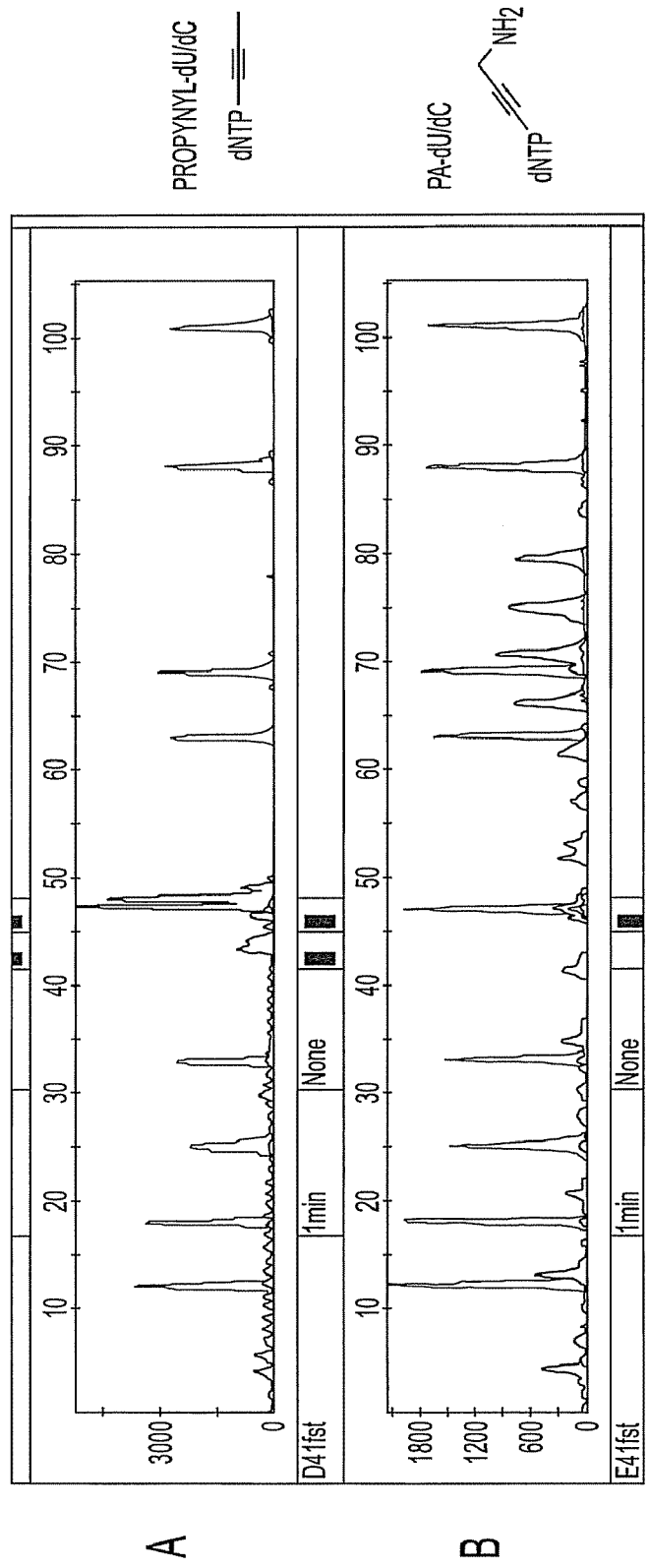

FIGS. 12A and 12B are electropherograms showing polymerase extension over an $(AAG)_{14}$ [SEQ ID NO: 1] template using a dUTP analog having residues with methyl terminal groups on the base (FIG. 12A) and a dUTP analog having residues with amino terminal groups on the base (FIG. 12B).

Figure 13:
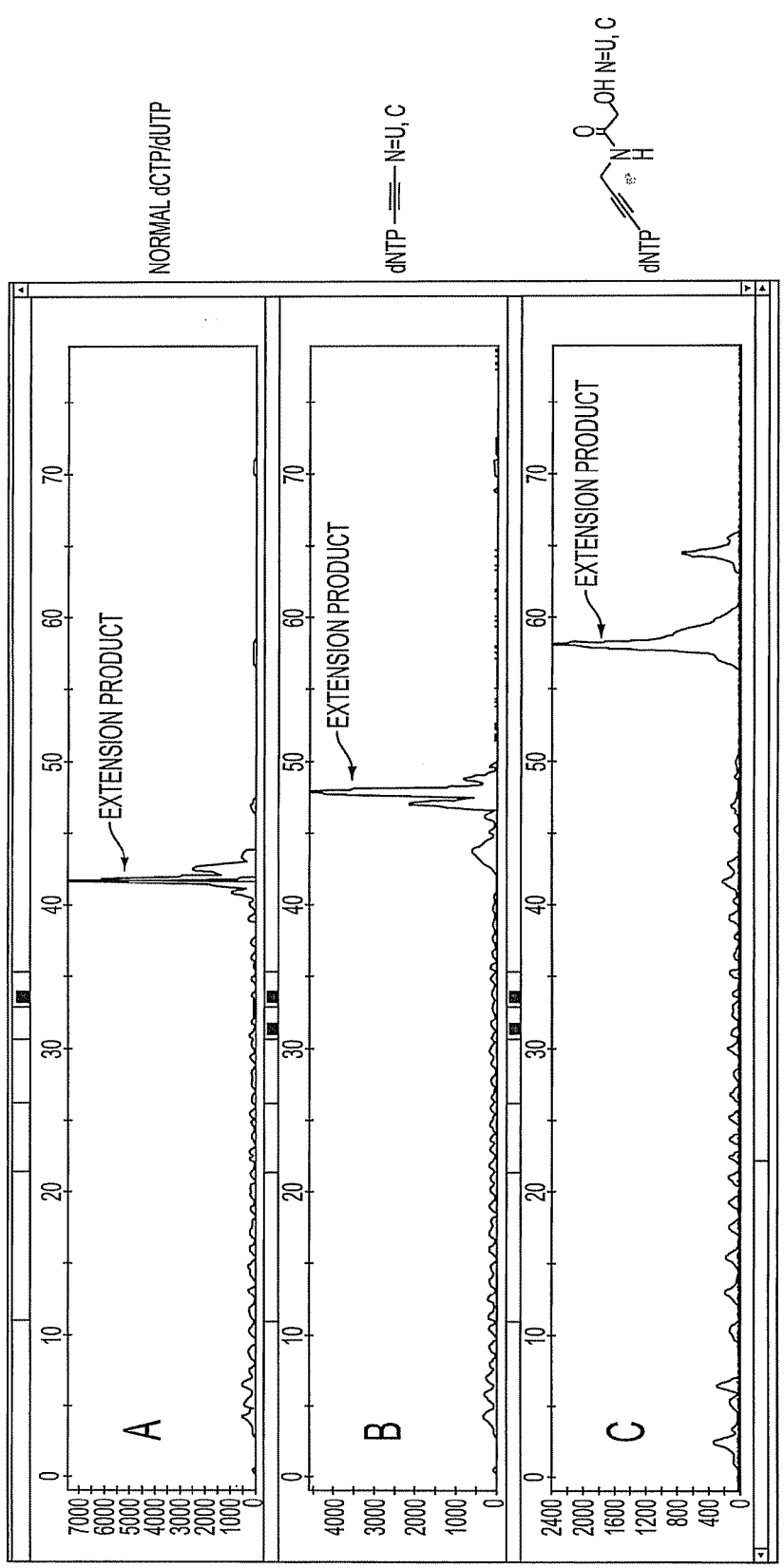

FIGS. 13A, 13B and 13C are electropherograms showing polymerase extension over an $(AAG)_{14}$ [SEQ ID NO: 1] template with natural dCTP/dTTP (FIG. 13A), a dNTP analog having residues with a methyl terminal group on the base (FIG. 13B), and a dNTP analog having residues with a hydroxyl terminal group on the base (FIG. 13C), wherein N is U or C.

Figure 14:
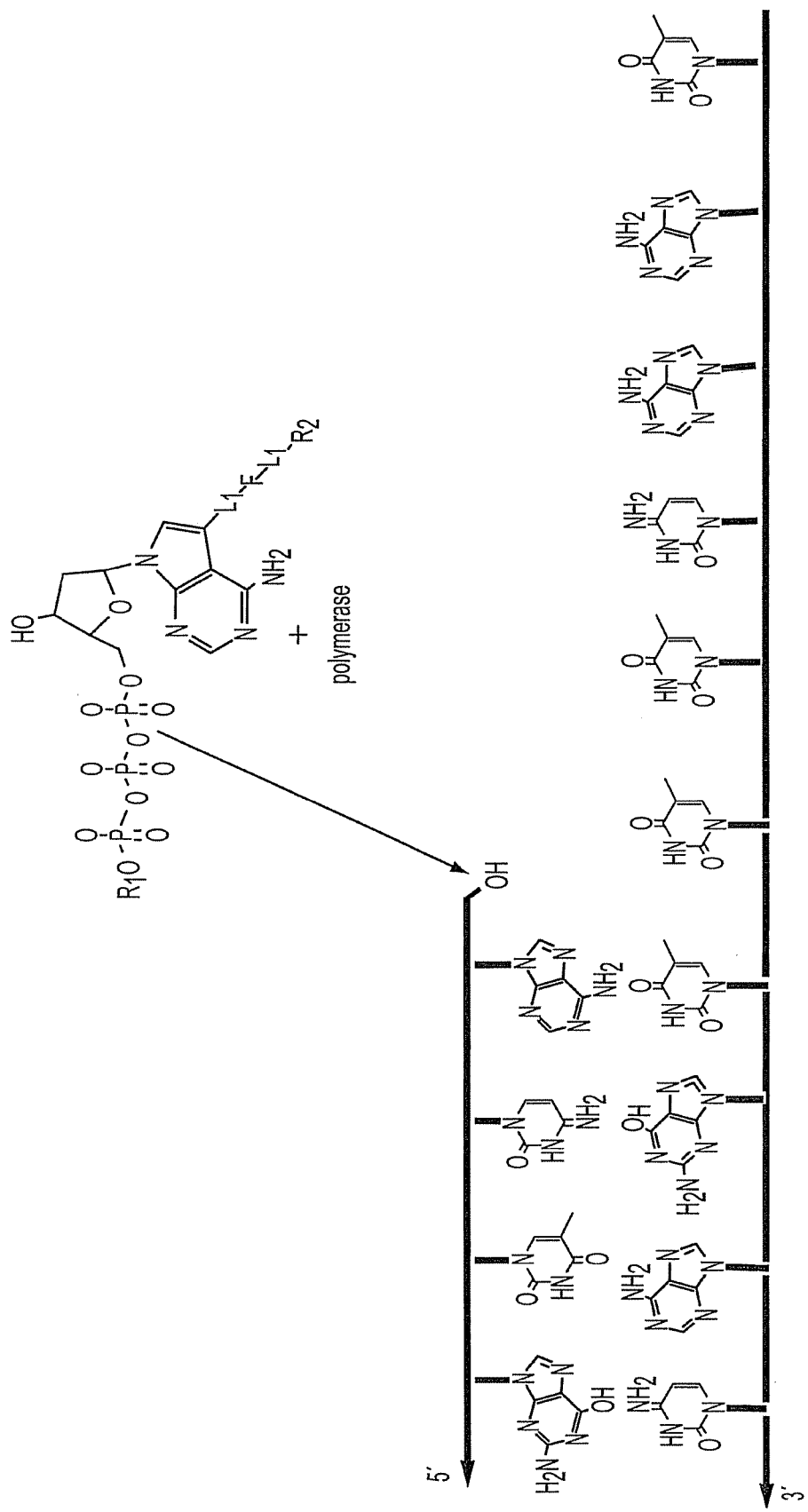

FIG. 14 is a schematic illustrating the polymerase directed addition of a nucleotide analog having a γ-phosphate substituent ($R_1$) and a substituent on the base to the 3' end of a nucleic acid over a template.

Figure 15:
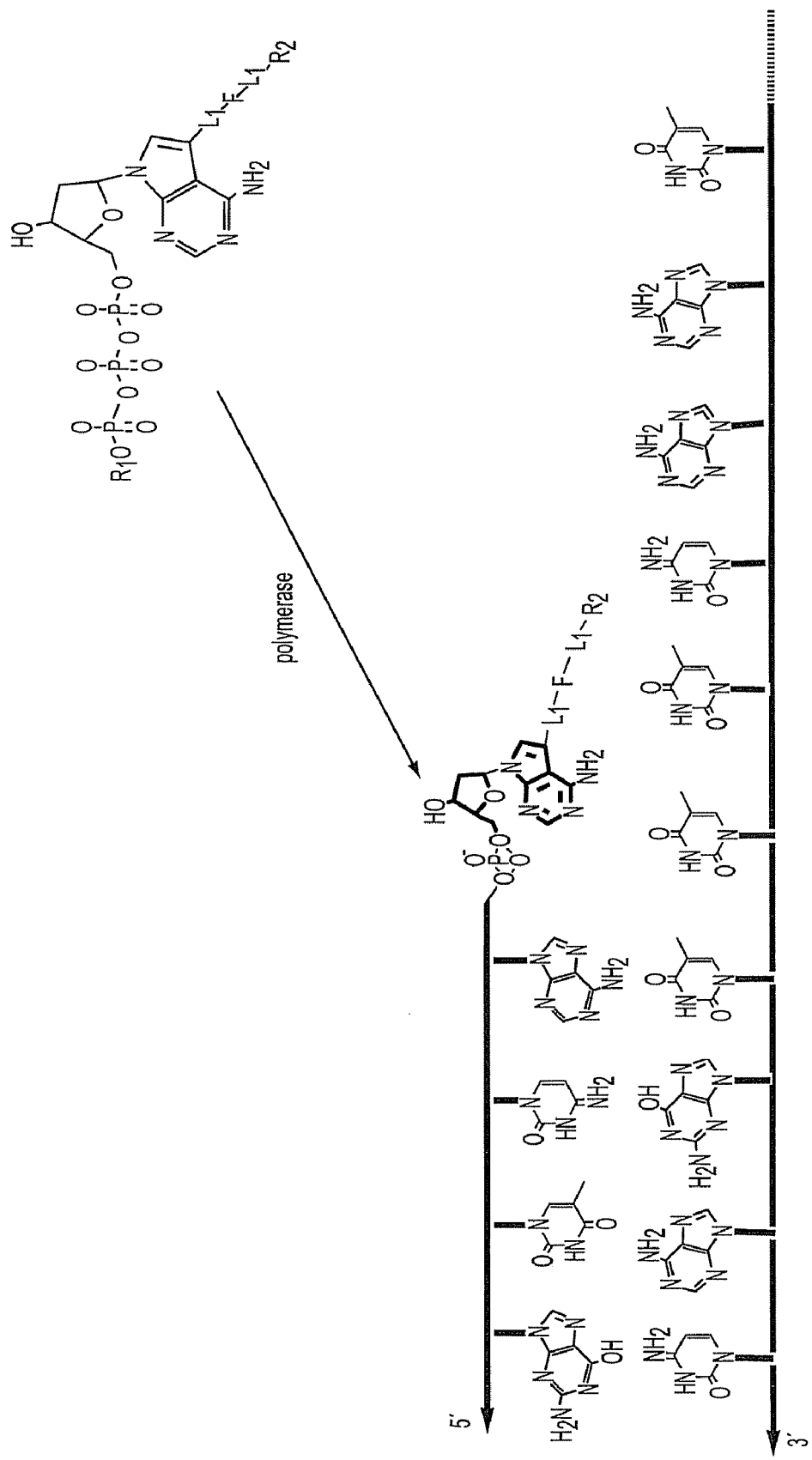

FIG. 15 is a schematic illustrating variations in the γ-phosphate substituent ($R_1$). When the γ-phosphate substituent ($R_1$) is a hydrocarbon group, a second nucleotide analog cannot be added to the 3' end of the nucleic acid until the substituent is removed from the base via cleavage and when $R_1$ is H, extension occurs at the 3' end of the nucleic acid.

Figure 16A:
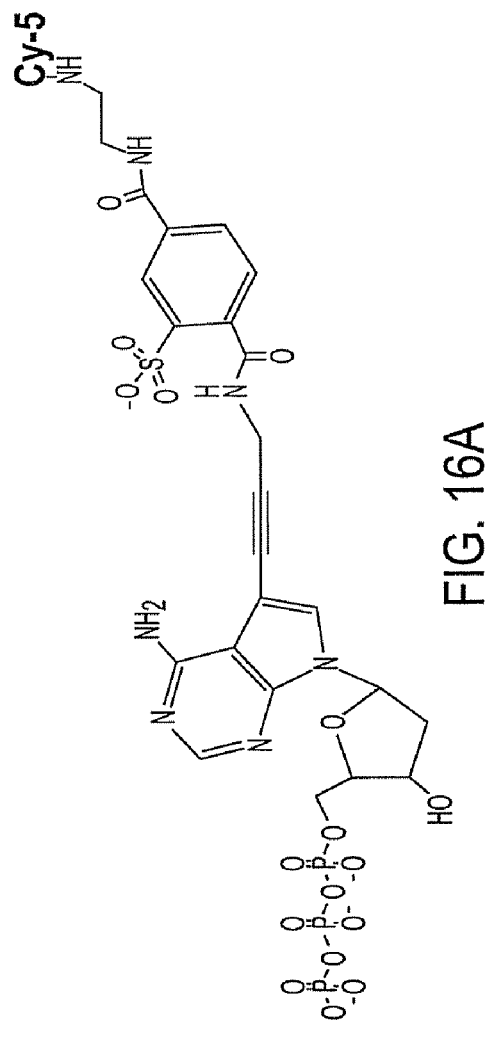

FIGS. 16A-16D are schematics showing the chemical structures of four different non-cleavable nucleotide analogs, dATP-L-Cy5, dCTP-L-Cy3, Benz-dATP-L-Cy5 and HC-dATP-L-Cy5, respectively, wherein the dATP-L-Cy5 and dCTP-L-Cy3 analogs do not have a γ-phosphate substituent and wherein the Benz-dATP-L-Cy5 analog shown in FIG. 16C has a benzyl group as a γ-phosphate substituent and the HC-dATP-L-Cy5 analog shown in FIG. 16D has a hydrocarbon group (i.e., HC) as a γ-phosphate substituent.

Figure 17A:
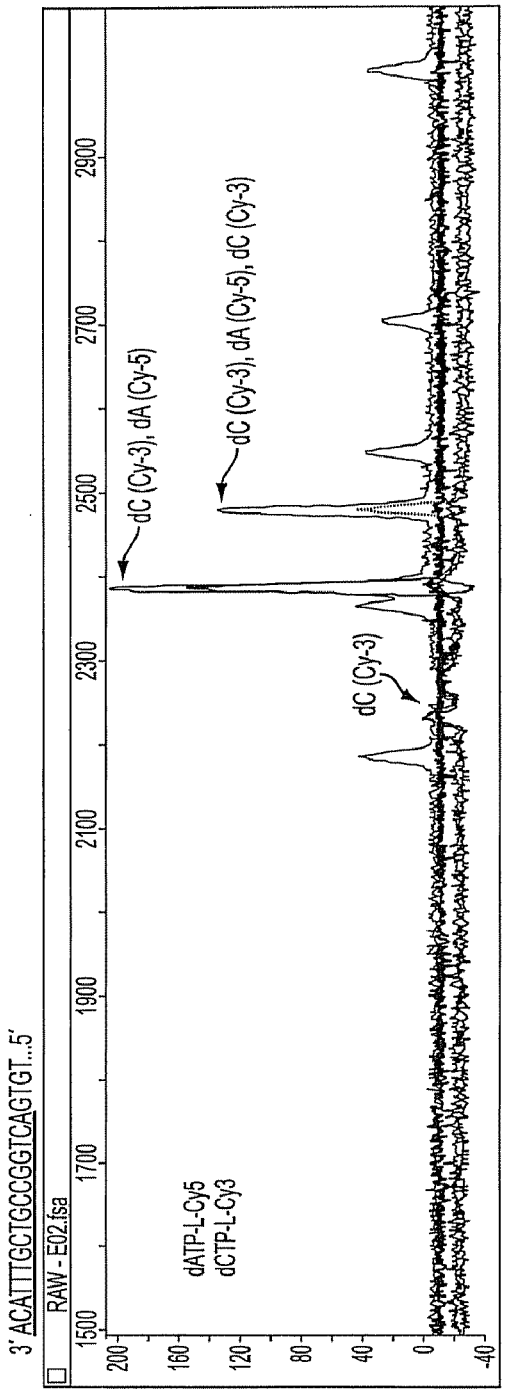
Figure 17B:
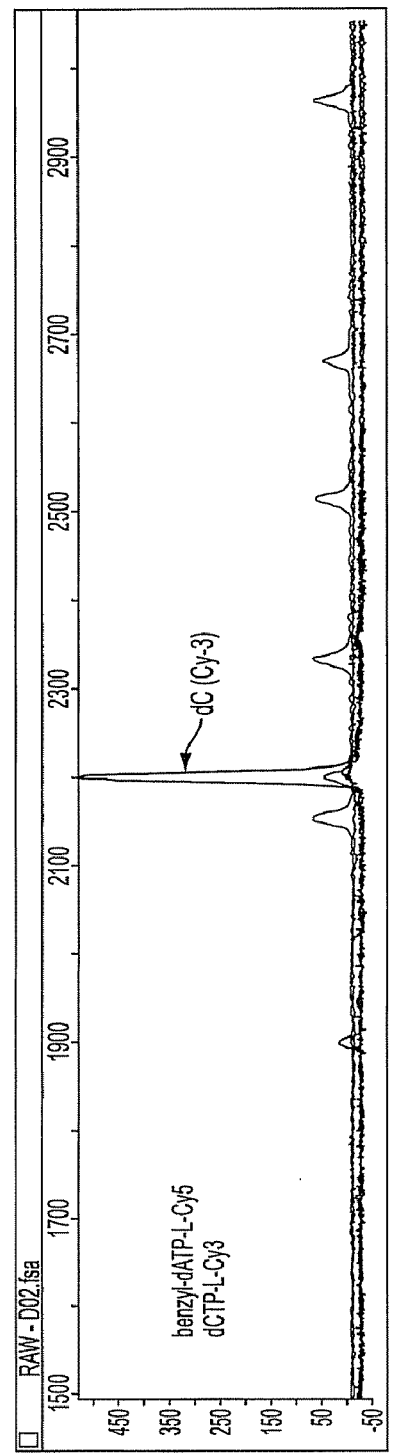

FIGS. 17A and 17B are electropherograms illustrating the termination effect of a γ-phosphate benzyl substituent on the nucleotide analog.

Figure 18:
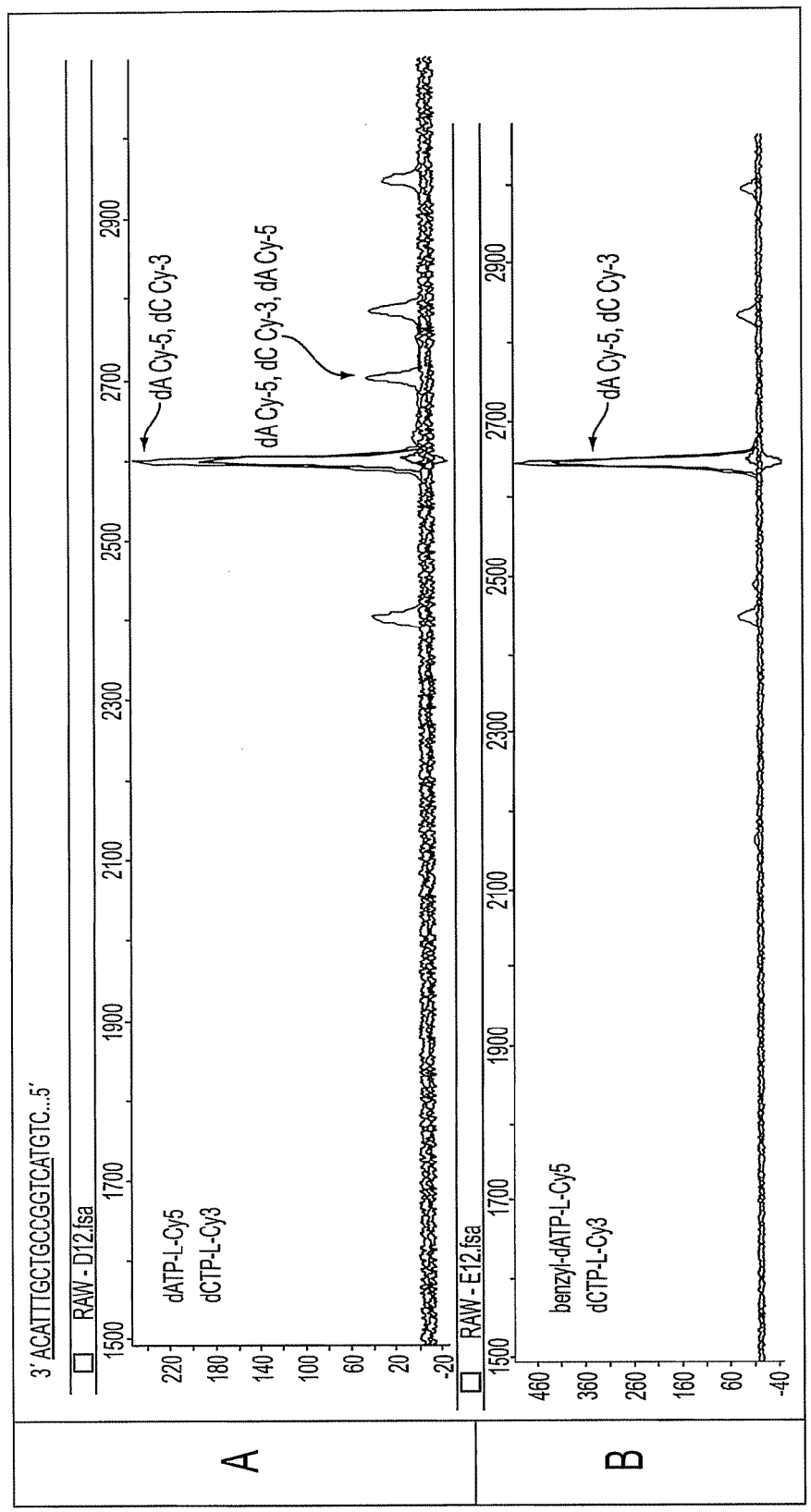

FIGS. 18A and 18B are electropherograms illustrating that a nucleotide analog which does not have a γ-phosphate substituent (e.g., the nucleotide analog of FIGS. 16A or 16B) can be incorporated after a nucleotide analog having a γ-phosphate benzyl substituent (e.g., the nucleotide analog of FIGS. 16C or 16D).

Figure 19:
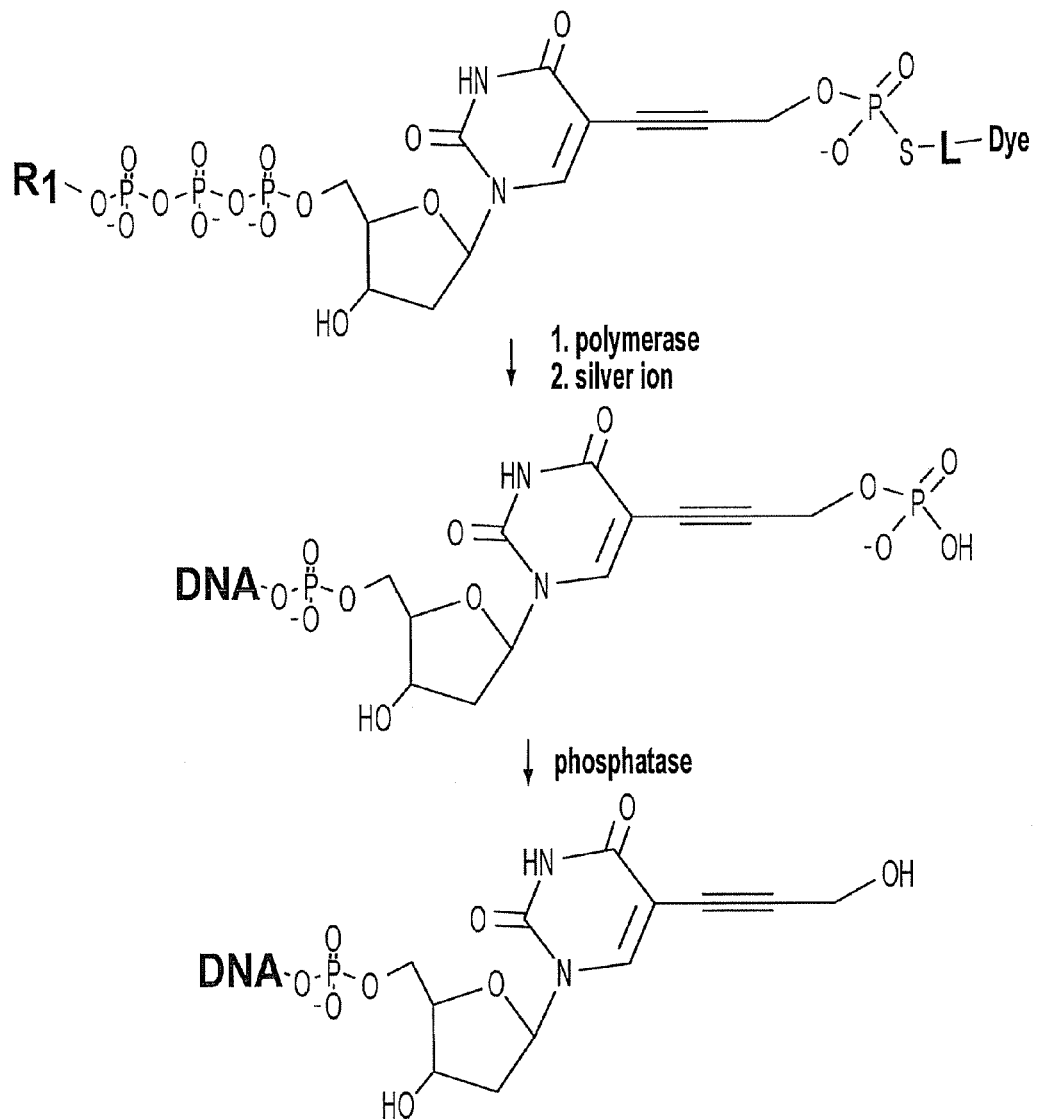

FIG. 19 illustrates the use of reversible terminators having silver ion cleavable linkers between the dye and the base wherein terminator activity is selectively controlled by the presence of a γ-phosphate substituent (R) and the Linker group (L) linking the base to the dye.

Figure 20:
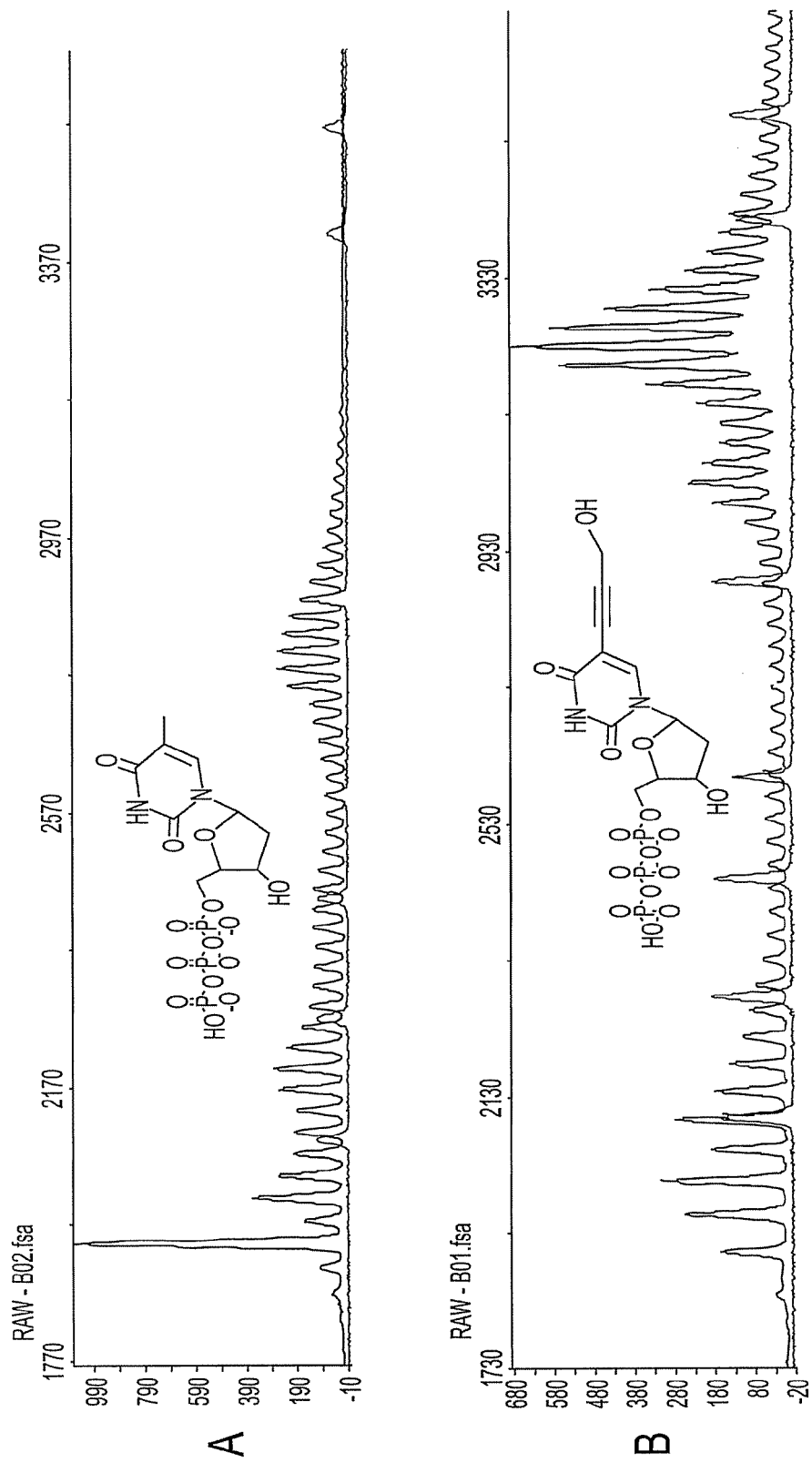

FIGS. 20A and 20B are electropherograms showing incorporation data for a 31 p(dA) template (i.e., 31 contiguous dA's) using Therminator II polymerase with dTTP (FIG. 20A) and a dUTP nucleotide analog having a propargyl alcohol residue on the base (FIG. 20B).

FIGS. 21A-21D are electropherograms showing the termination properties of γ-phosphate substituted dUTP analogs having an O-propargyl-S-substituent at the 5 position.

FIGS. 22A-22D are electropherograms showing the misincorporation properties of γ-phosphate substituted dUTP analogs having an O-propargyl-S-substituent at the 5 position.

Figure 23:
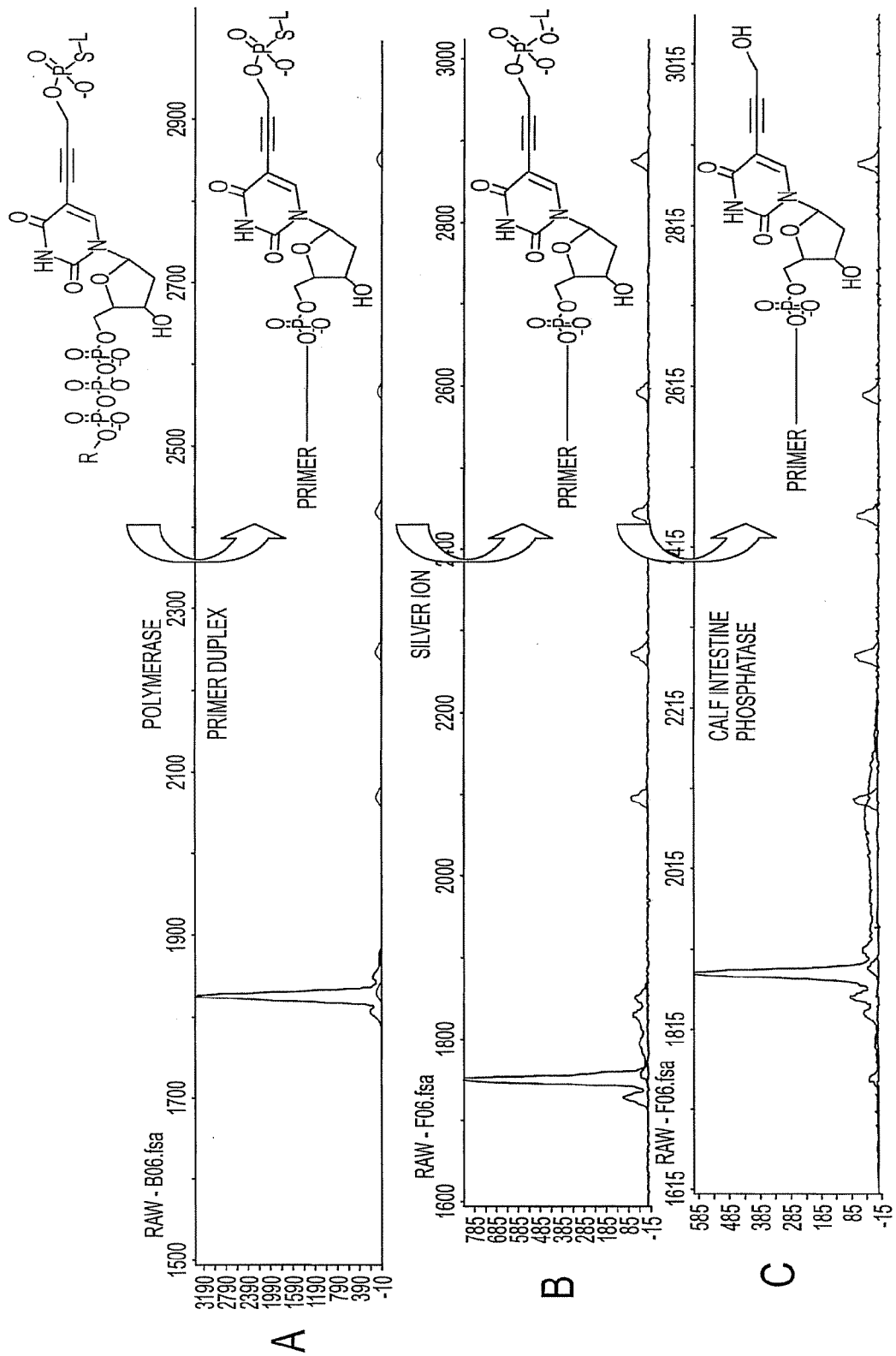

FIGS. 23A-23C are electropherograms and a schematic showing the cleavage reactions needed to regenerate the 3'-hydroxyl for the next termination event wherein FIG. 23A shows the incorporation of dU onto a primer-target duplex, FIG. 23B shows a nearly quantitative cleavage of the linker with silver ions to the phosphate and FIG. 23C shows the loss of the phosphate group from the fragment by treatment with Calf Intestine Phosphatase.

Figure 24:
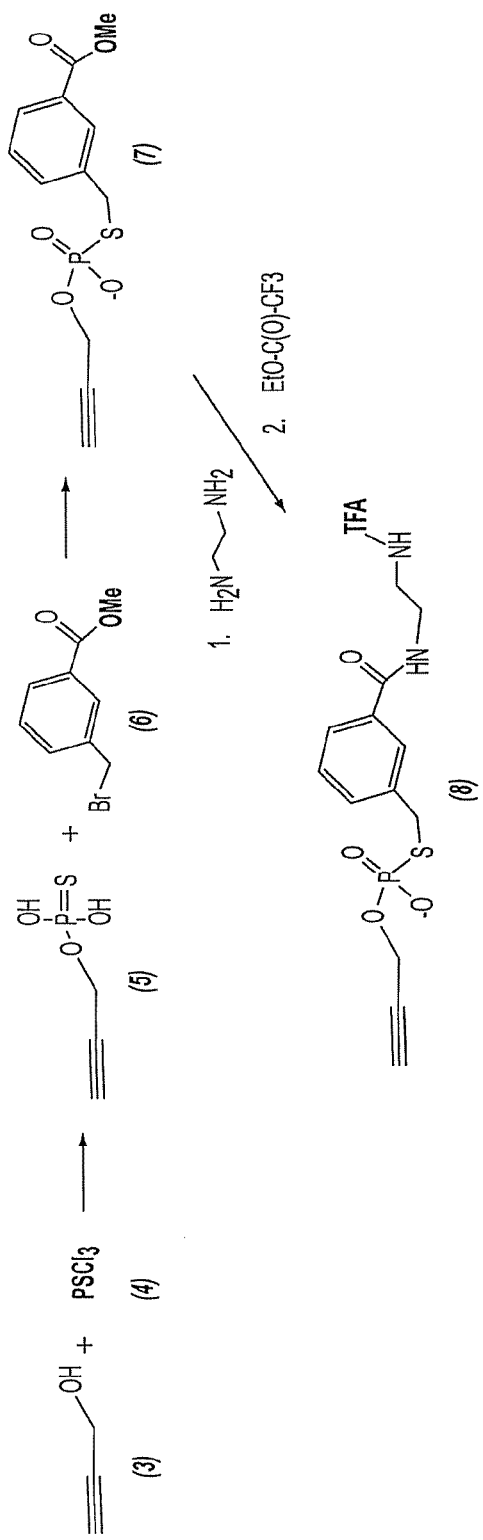

FIG. 24 is a schematic illustrating the synthesis of a propargyl ester of phosphorothiolate linker (8).

Figure 25:
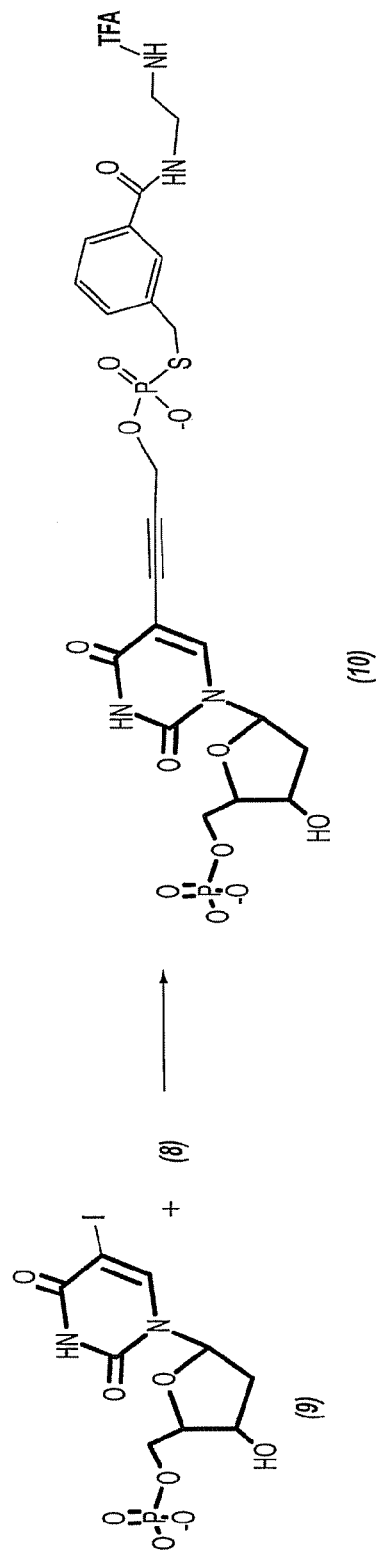

FIG. 25 is a schematic illustrating the synthesis of dU 5'-monophosphate (10).

Figure 26:
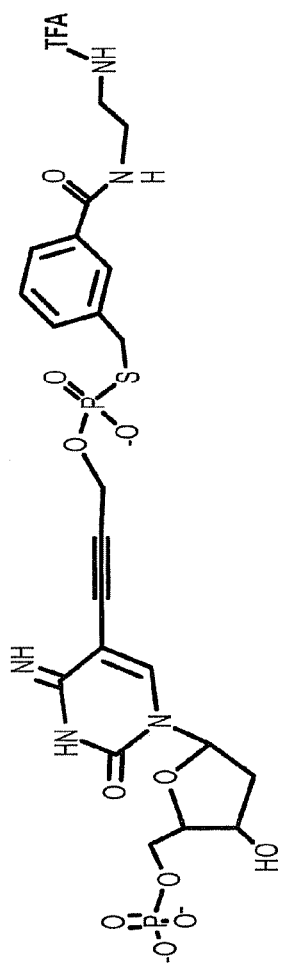

FIG. 26 is a schematic illustrating the synthesis of dC 5'-monophosphate (12).

Figure 27:
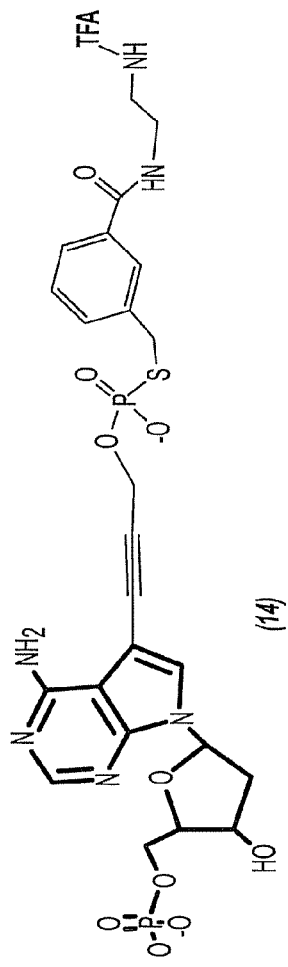

FIG. 27 is a schematic illustrating the synthesis of dA 5'-monophosphate (14).

Figure 28:
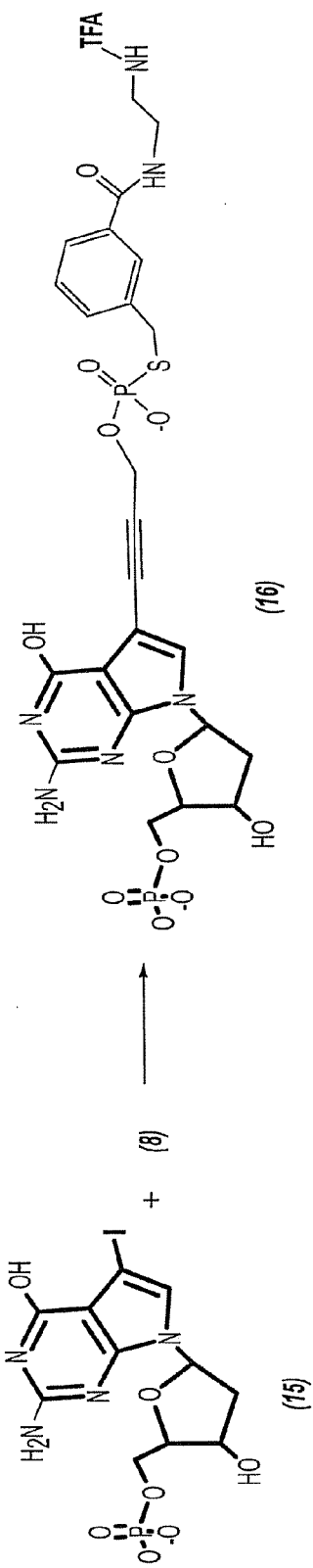

FIG. 28 is a schematic illustrating the synthesis of dG 5'-monophosphate (16).

Figure 29:
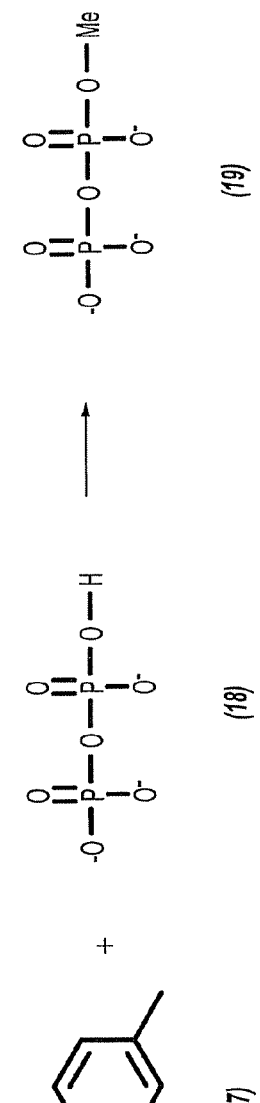

FIG. 29 is a schematic illustrating the synthesis of methylpyrophosphate (19).

Figure 30:
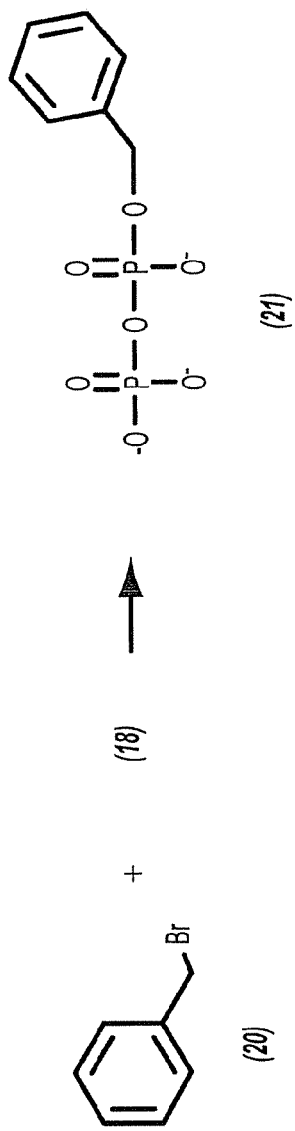

FIG. 30 is a schematic illustrating the synthesis of benzylpyrophosphate (21).

Figure 31:
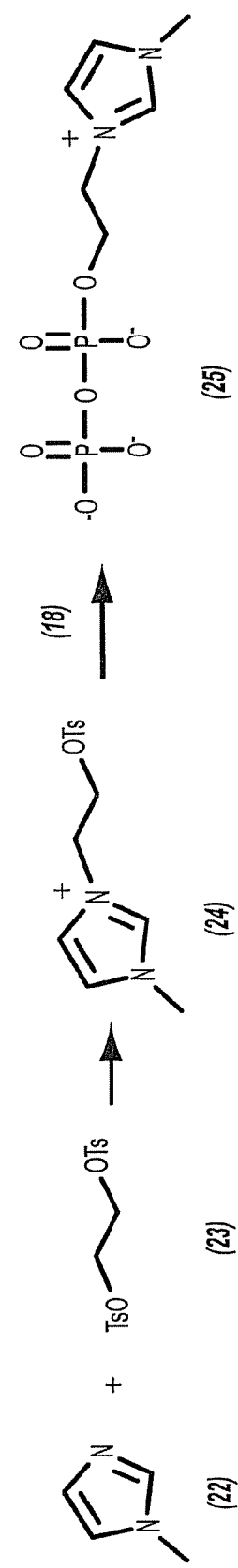

FIG. 31 is a schematic illustrating the synthesis of 2-(N-(3-methylimidazolium))-ethyl pyrophosphate (25).

FIG. 32 is a schematic illustrating the synthesis of γ-methyl-dUTP (26).

FIG. 33 is a schematic illustrating the synthesis of γ-benzyl-dATP (27).

Figure 34:
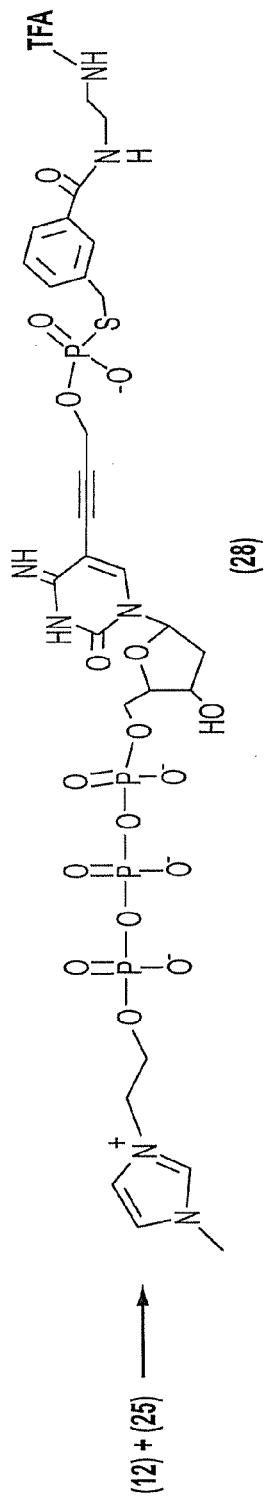

FIG. 34 is a schematic illustrating the synthesis of γ-(2-(N-(3-methylimidazolium))-ethyl)-dCTP (28).

Figure 35:
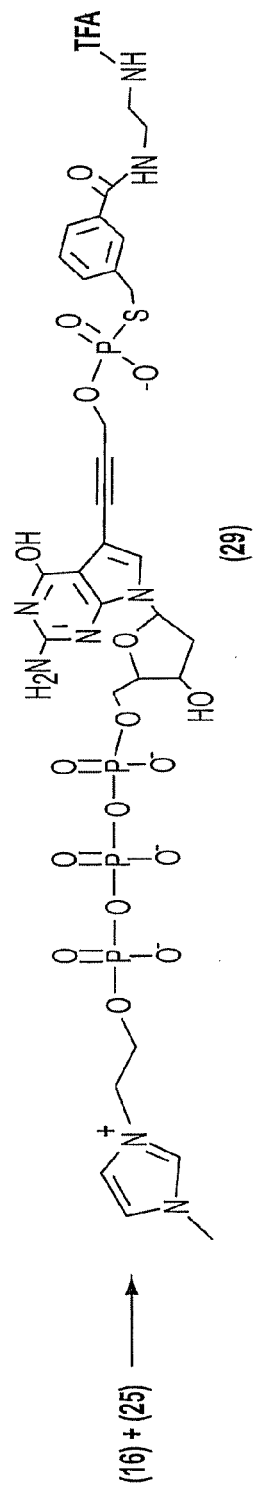

FIG. 35 is a schematic illustrating the synthesis of γ-(2-(N-(3-methylimidazolium))-ethyl)-dGTP (29).

Figure 36A:
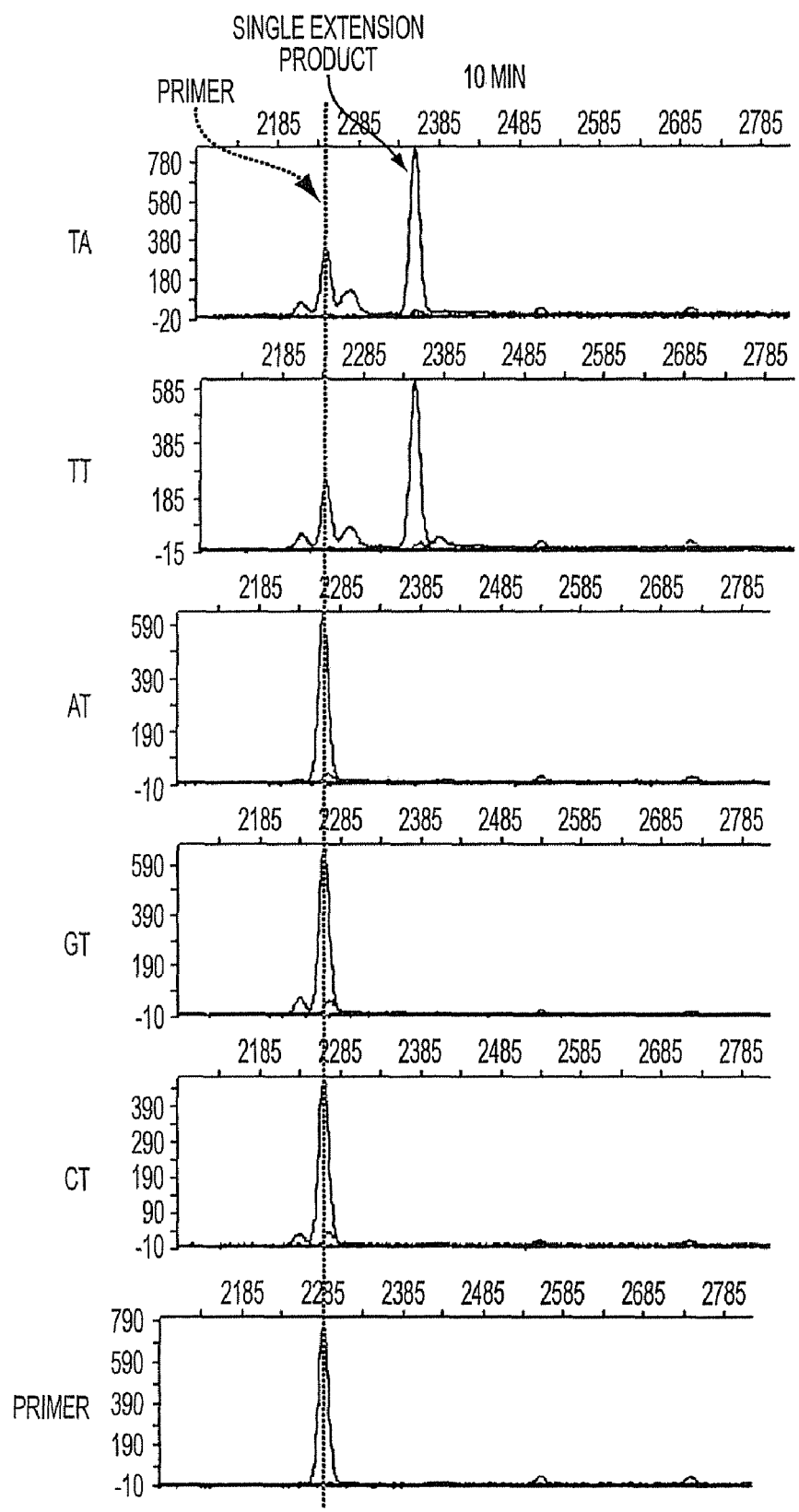
Figure 36B:
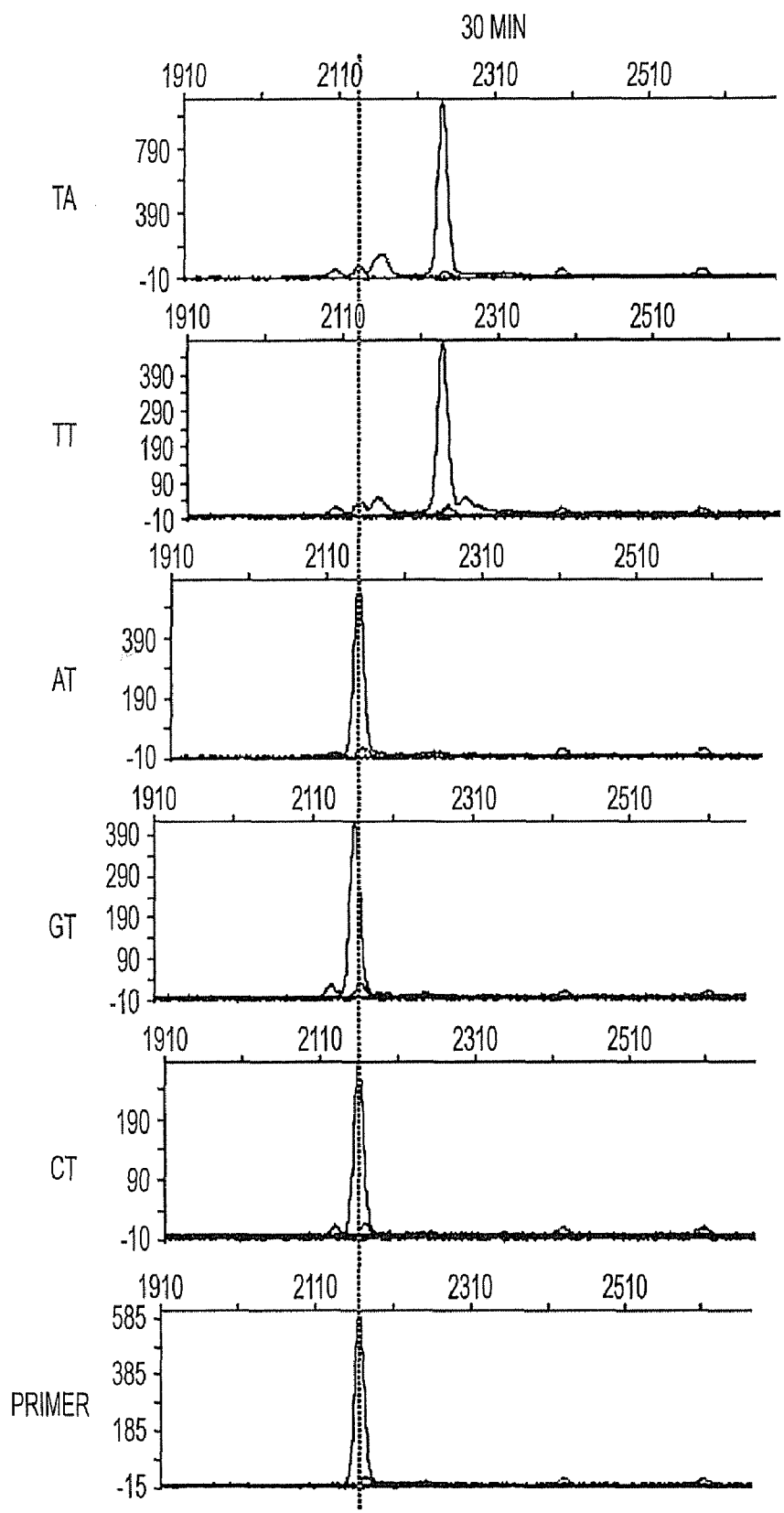
Figure 36C:
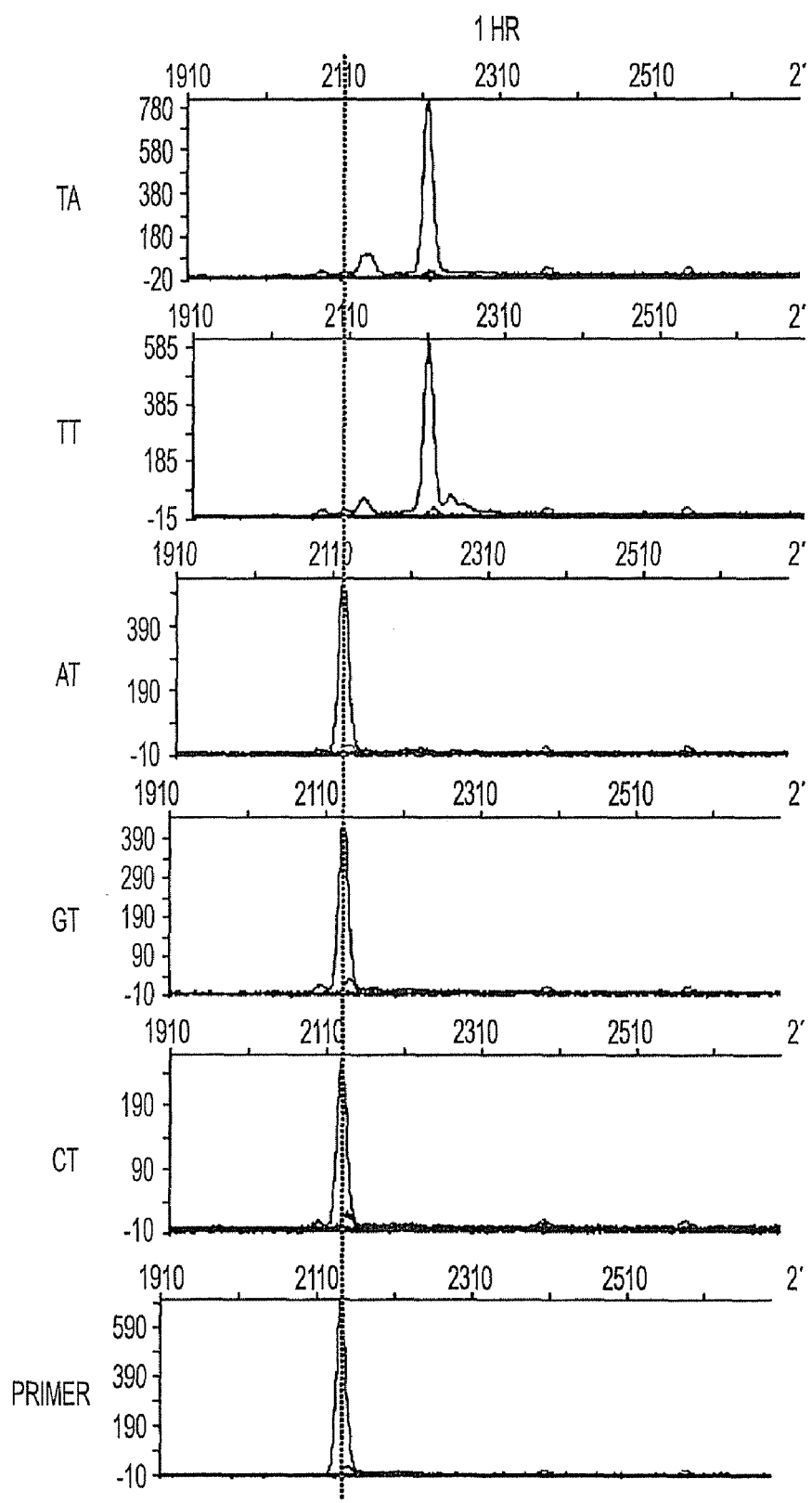

FIG. 36 are electropherograms showing the termination and mis-incorporation properties of γ-benzyl-dATP.

Figure 37A:
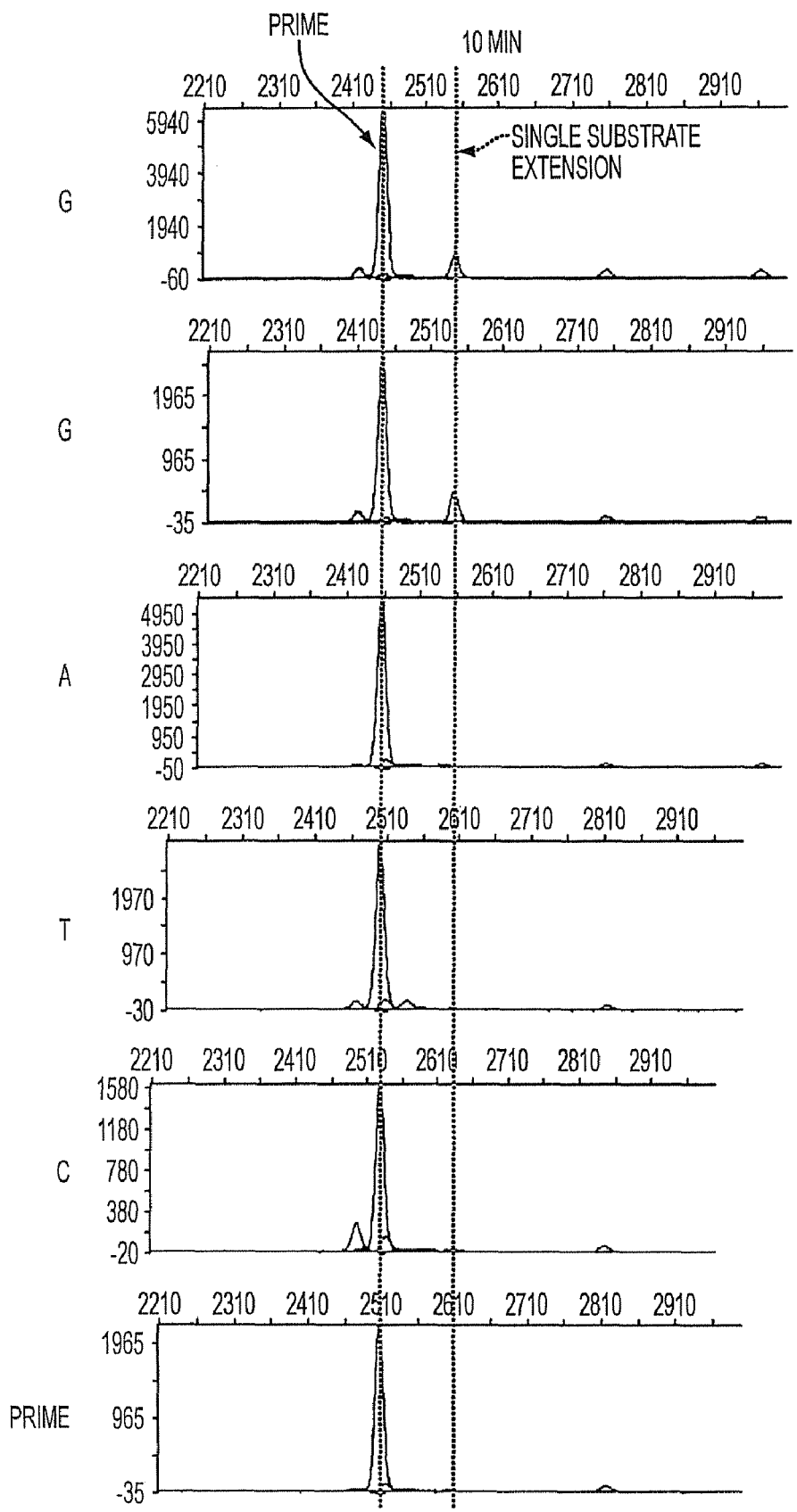
Figure 37B:
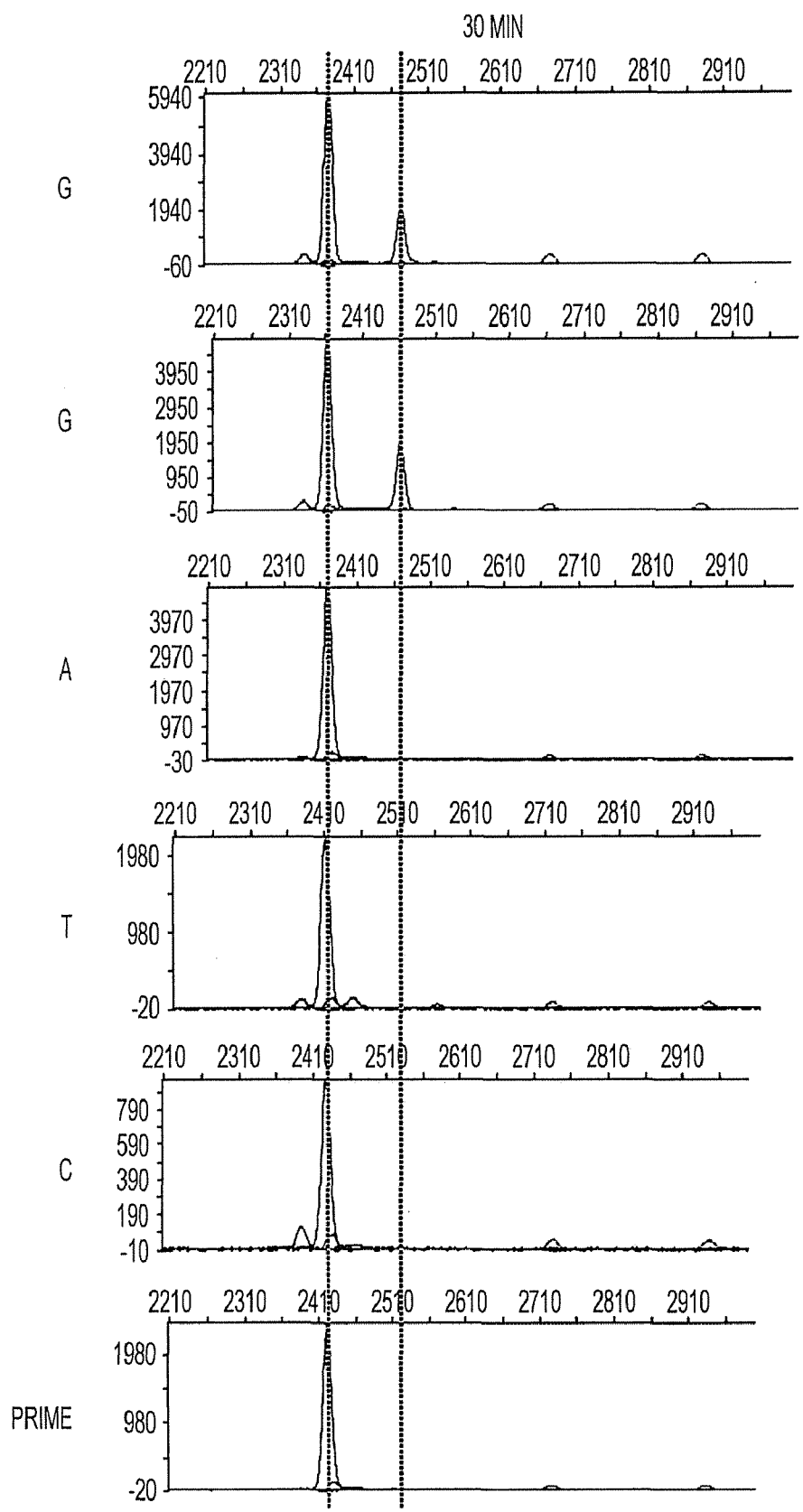
Figure 37C:
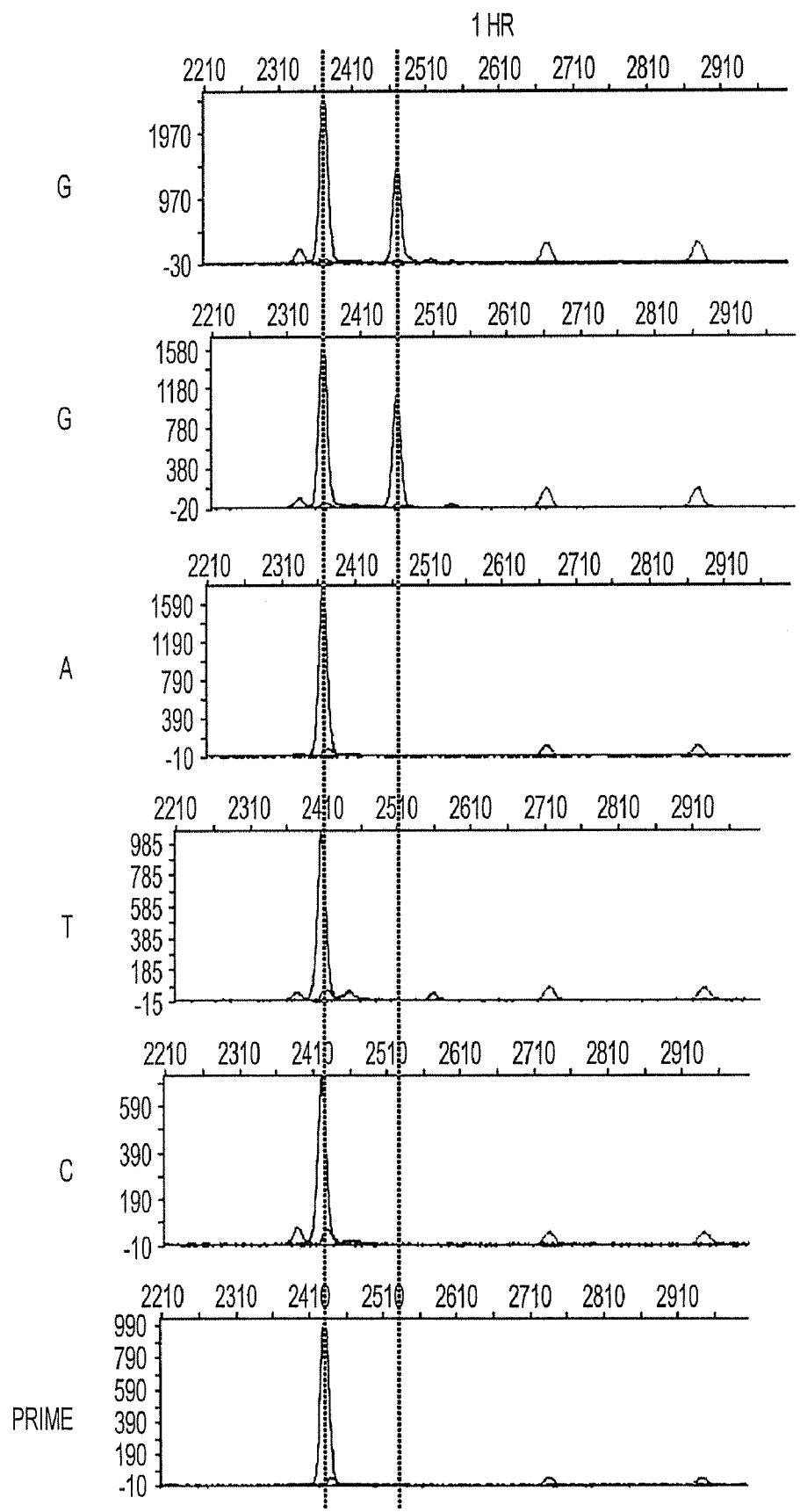

FIG. 37 are electropherograms showing the termination and mis-incorporation properties of γ-imidazolium-dCTP.

Figure 38A:
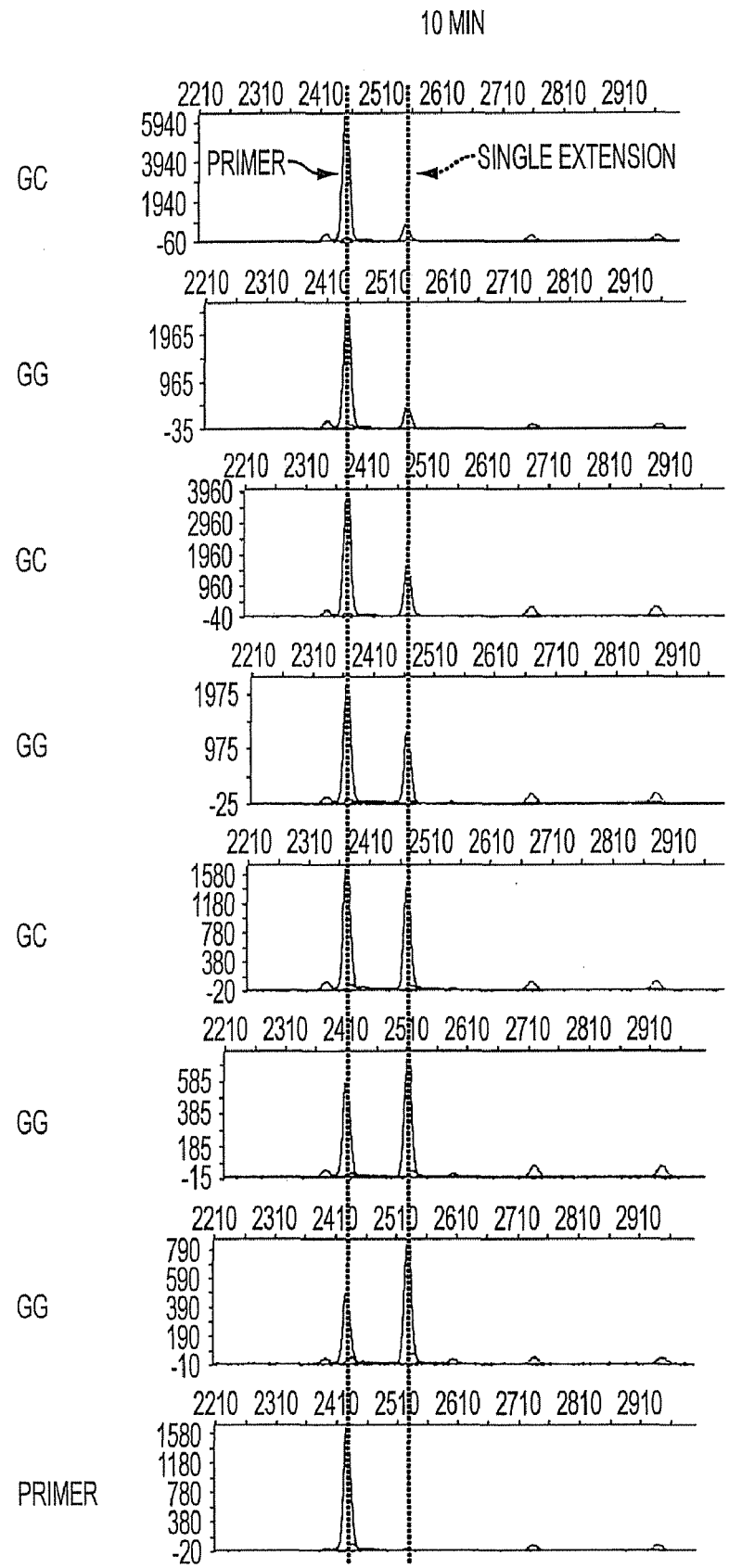
Figure 38B:
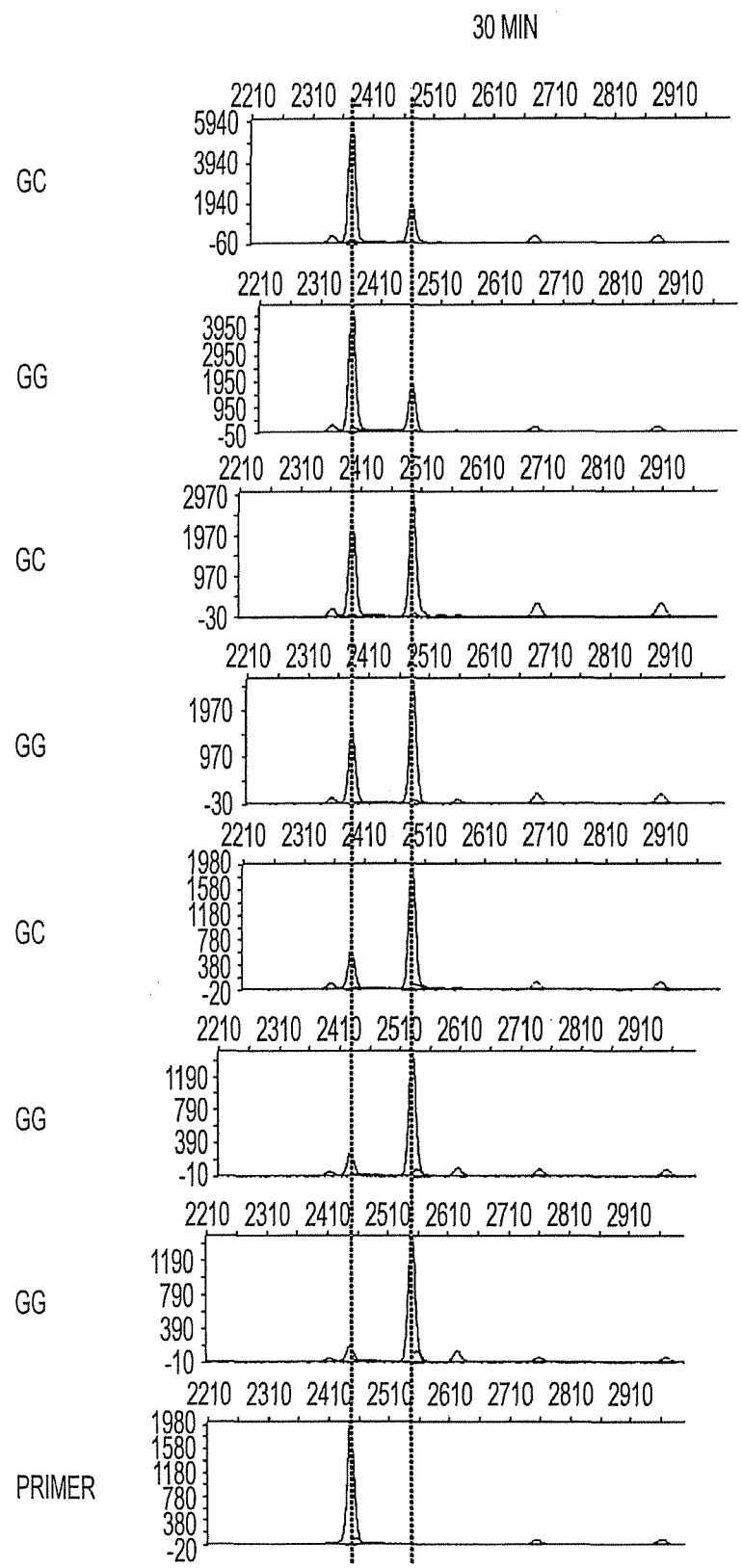
Figure 38C:
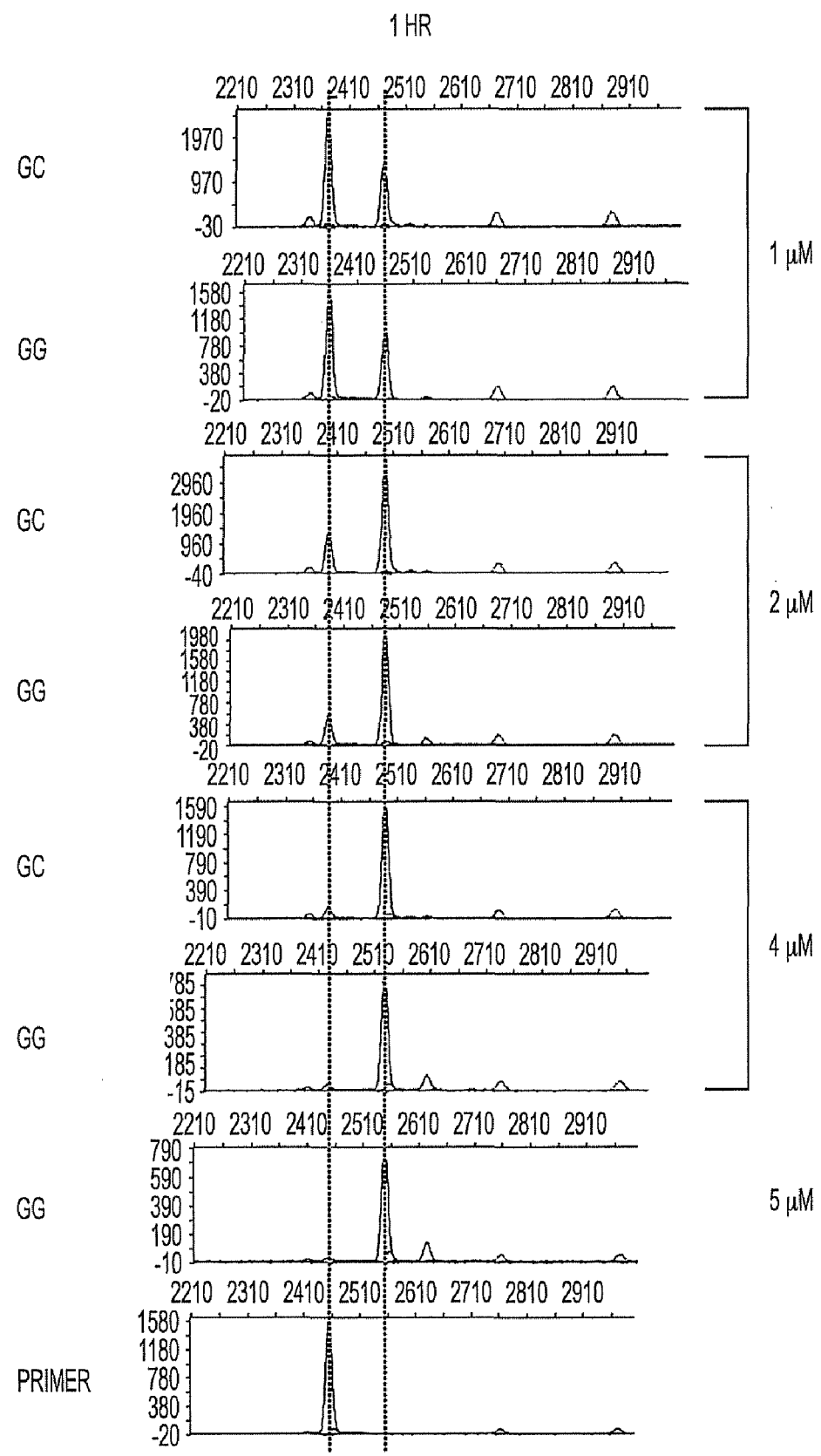

FIG. 38 are electropherograms showing the termination properties of γ-imidazolium-dCTP at various substrate concentrations.

Figure 39A:
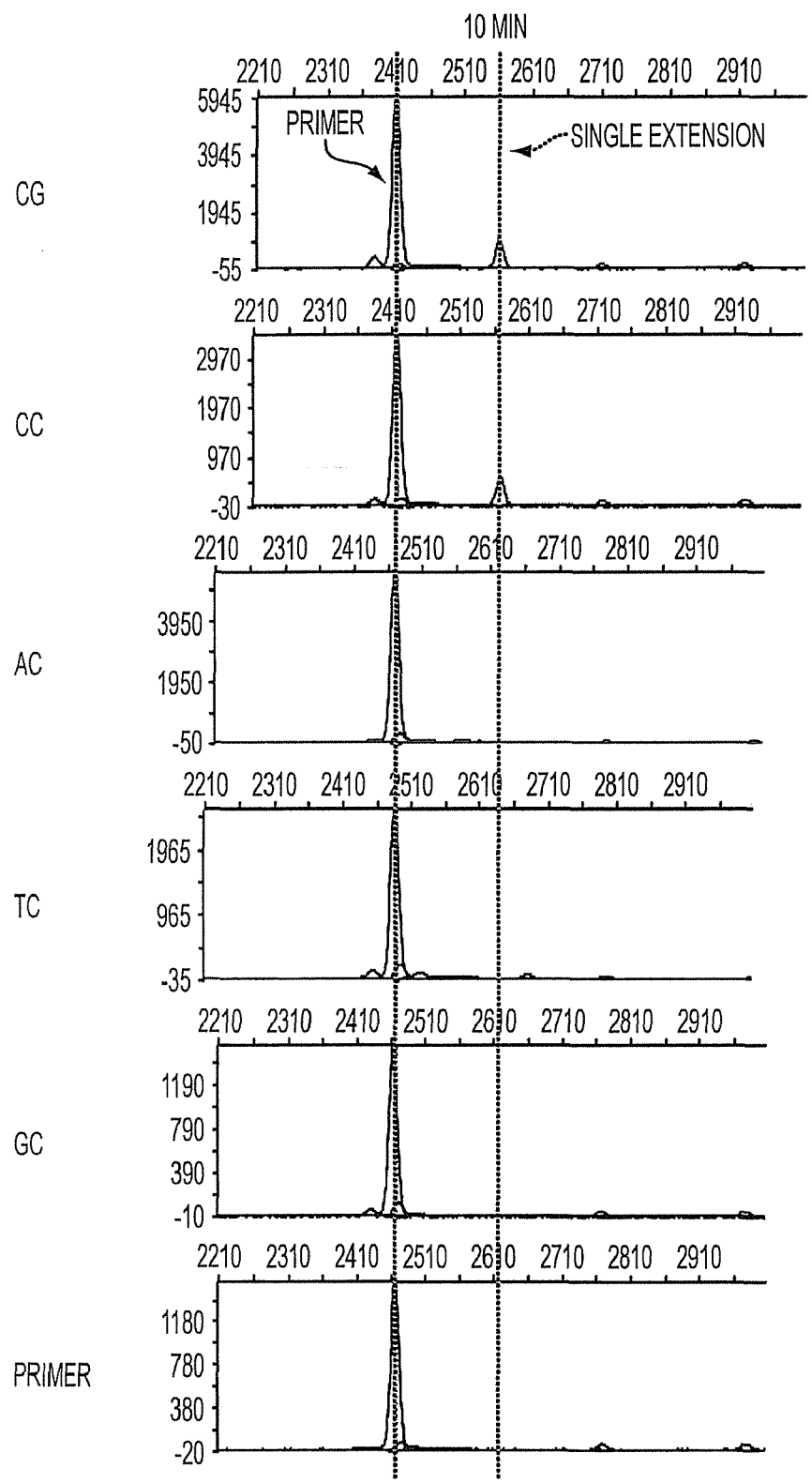
Figure 39B:
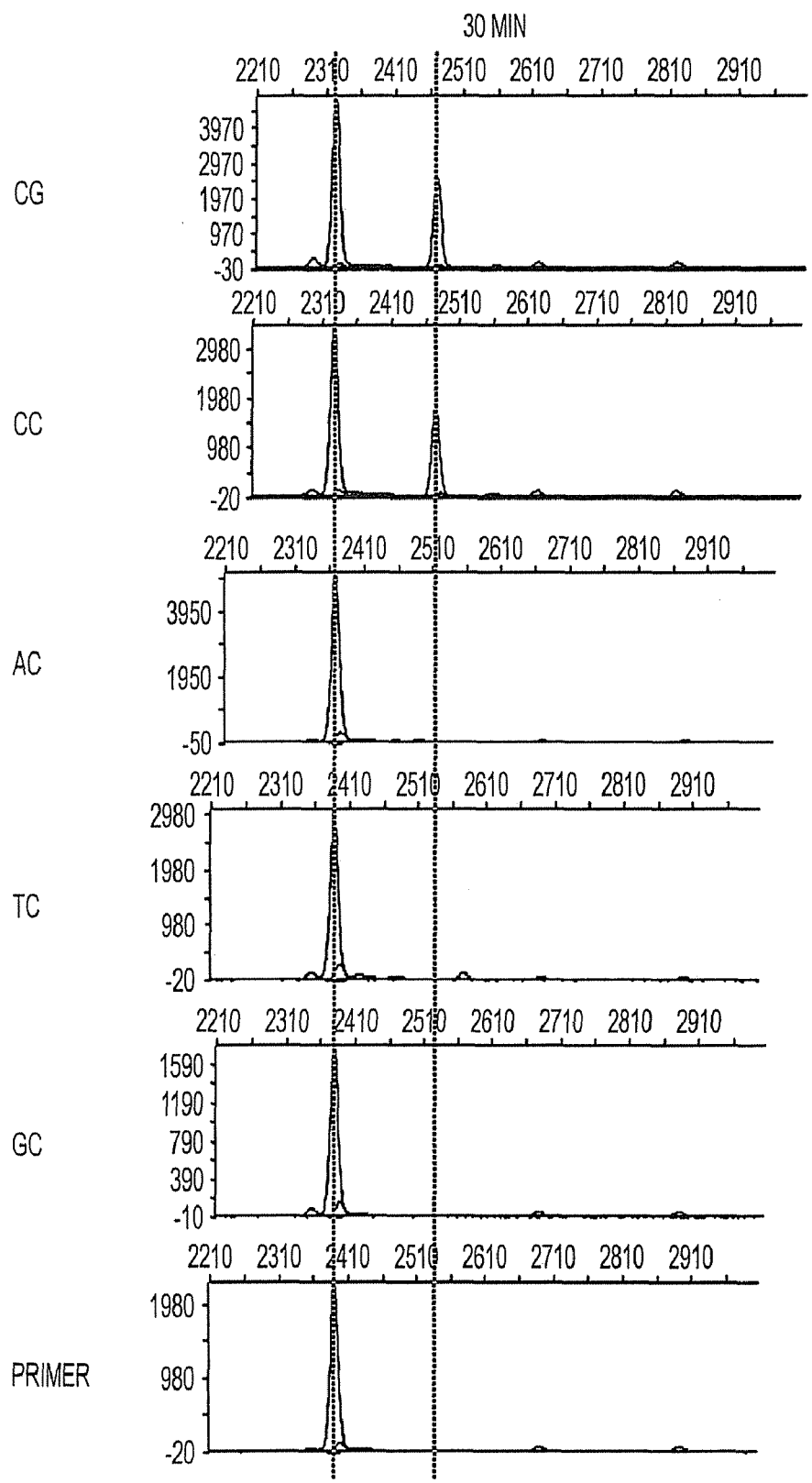
Figure 39C:
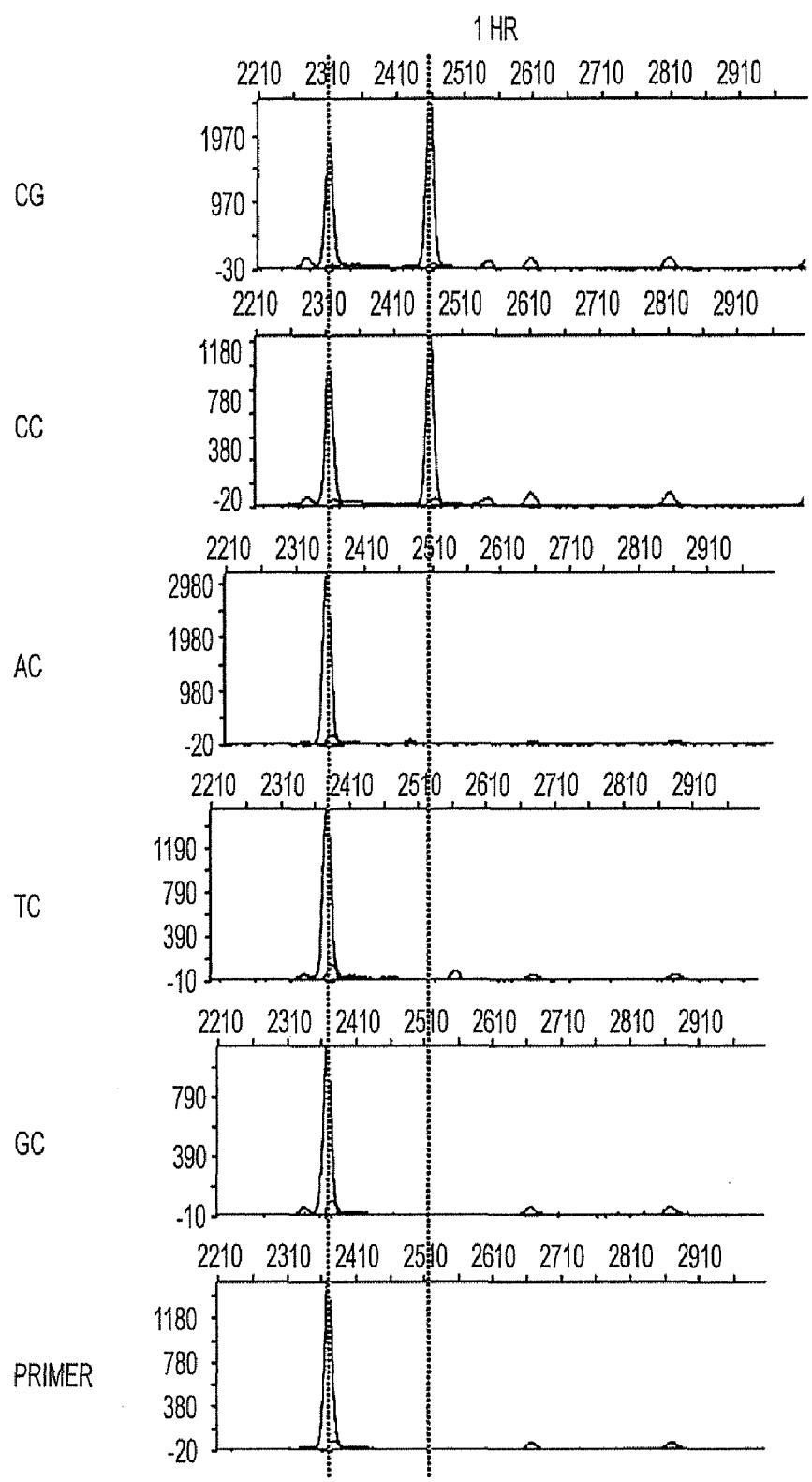

FIG. 39 are electropherograms showing the termination and mis-incorporation properties of γ-imidazolium-dGTP.

Figure 40A:
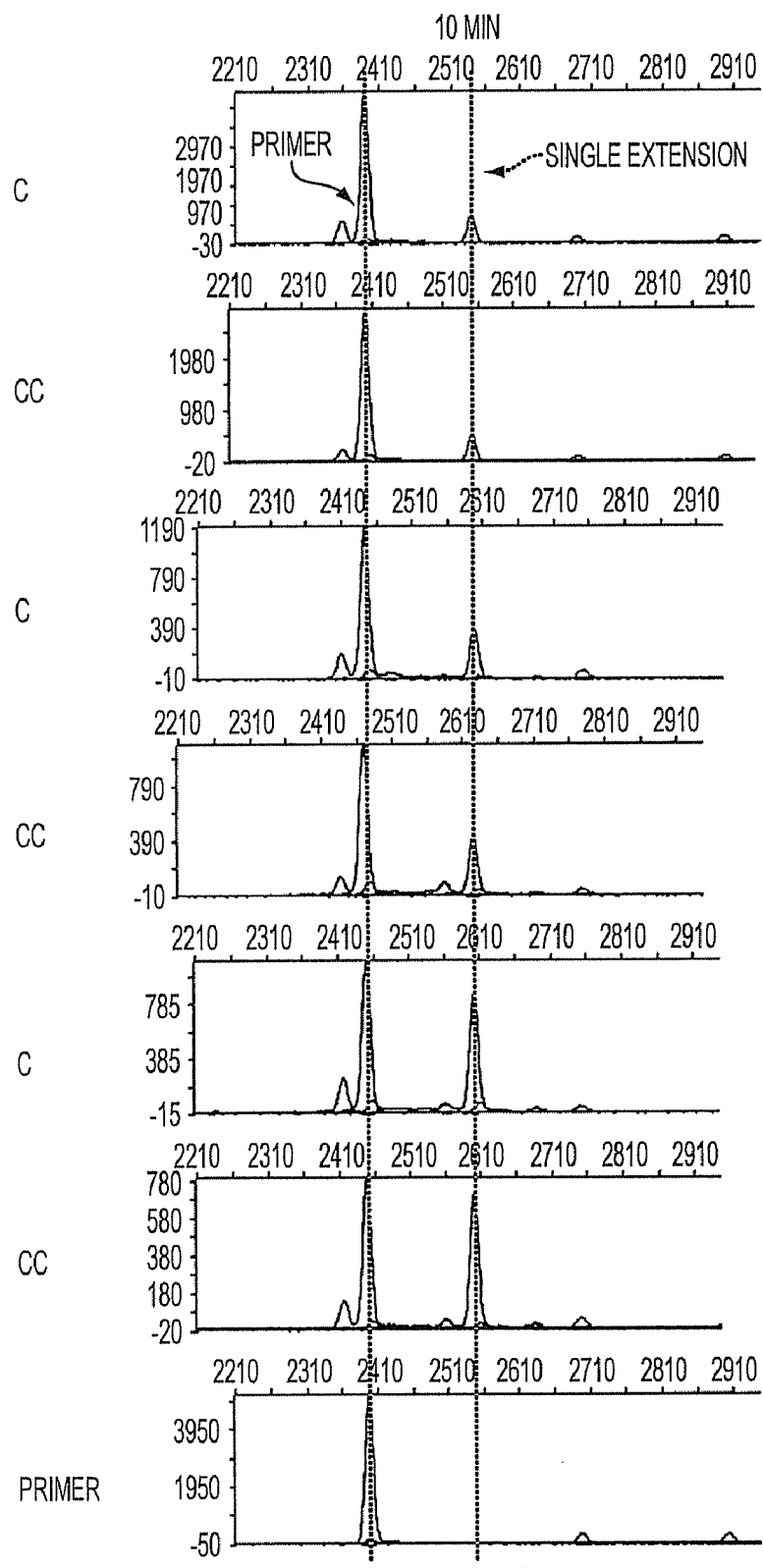
Figure 40B:
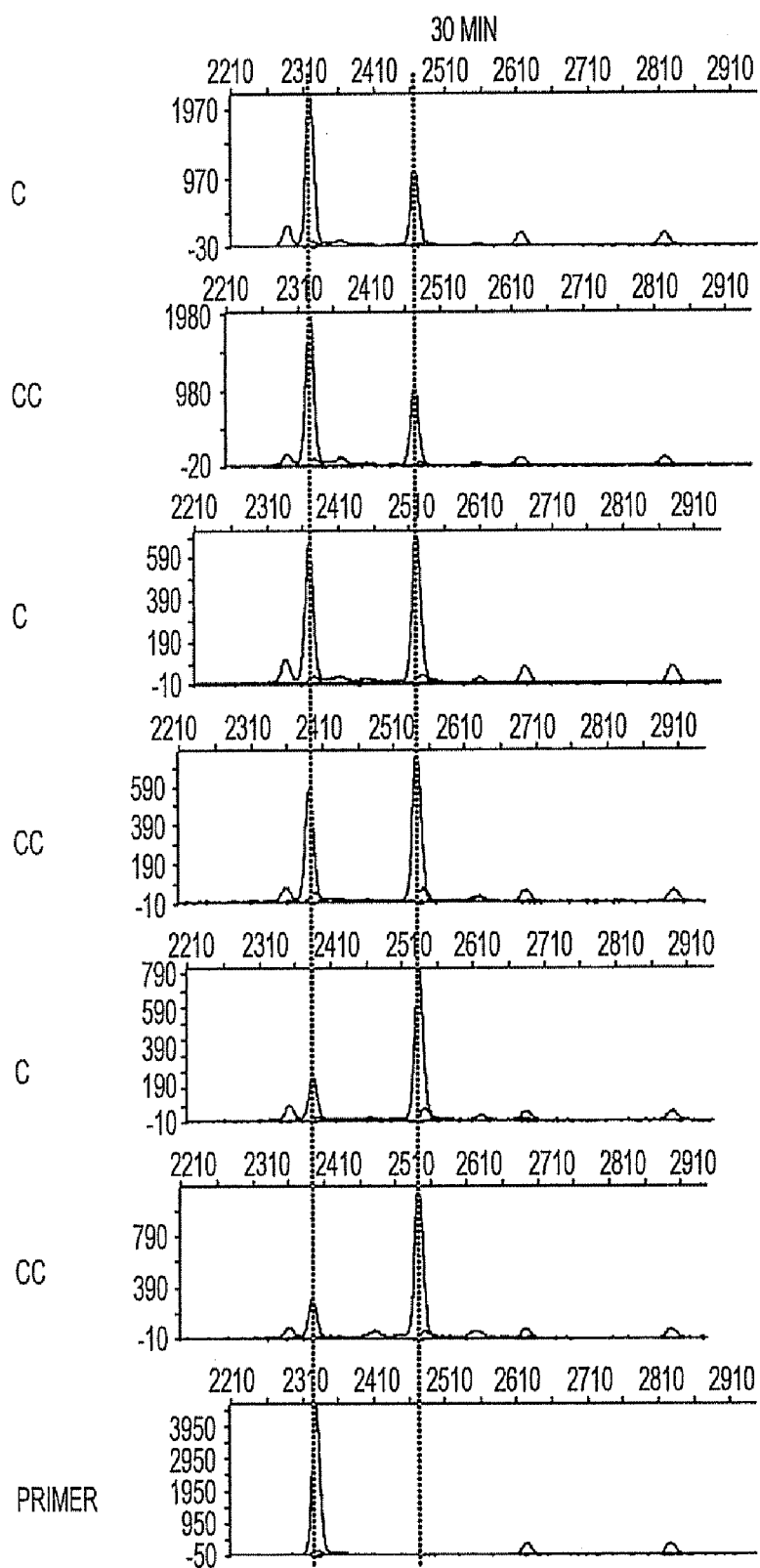
Figure 40C:
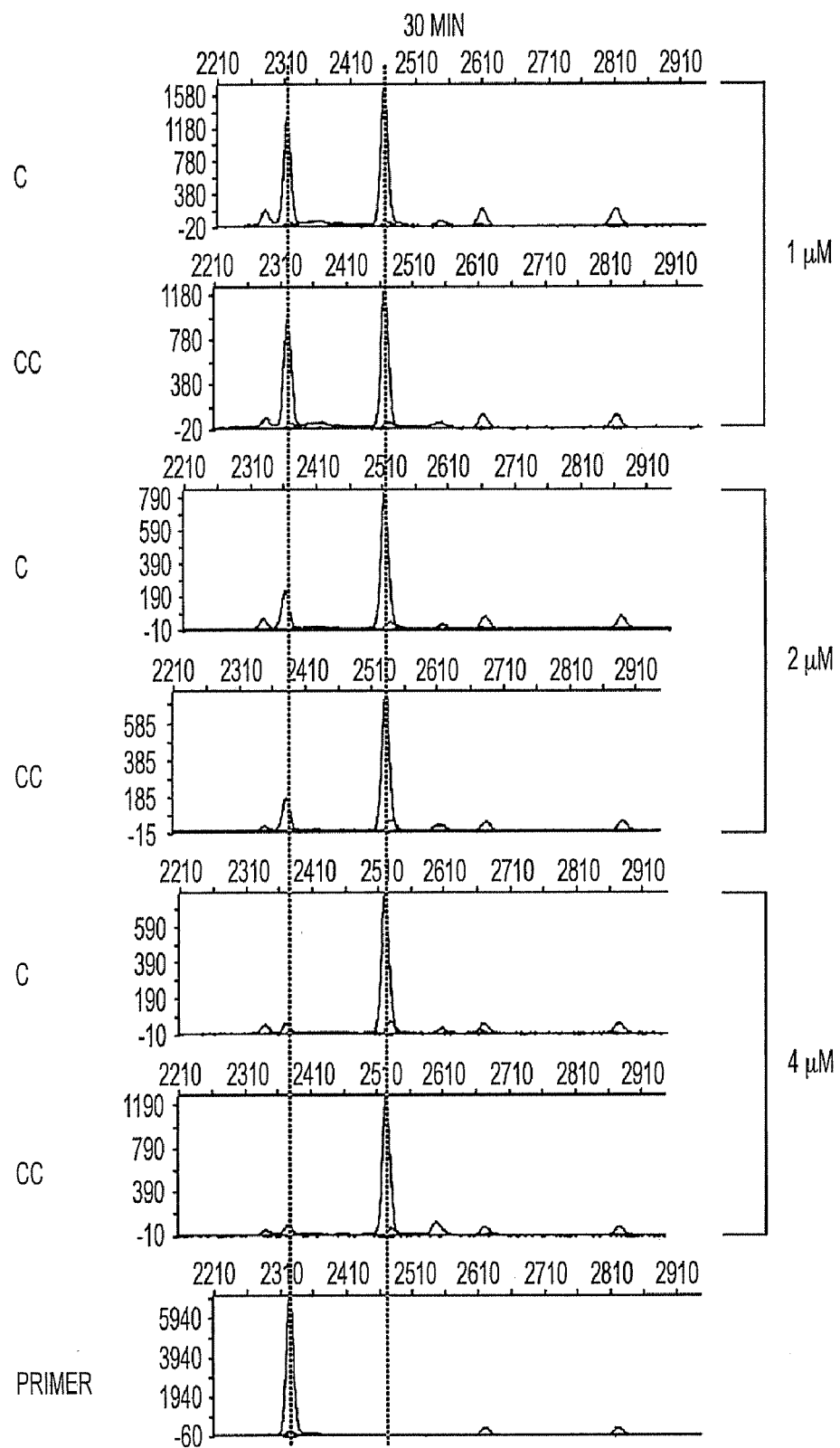

FIG. 40 are electropherograms showing the termination properties of γ-imidazolium-dGTP at various substrate concentrations.

DESCRIPTION OF THE VARIOUS EMBODIMENTS

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

As used herein, the term "nucleoside" includes 2'-deoxy nucleosides and 2'-hydroxyl nucleosides. The term "analogs" in reference to nucleosides includes synthetic nucleosides having modified base moieties and/or modified sugar moieties. Such analogs include synthetic nucleosides designed to enhance binding properties, reduce degeneracy, increase specificity, and the like. Such analogs also include nucleosides having residues attached to the base which do not occur in the natural nucleoside.

As used herein, the term "heteroatom" means an atom other than H or C.

As used herein, the phrase "terminal group" refers to the functional group at the terminal position of a moiety. For example, cleavage of the linker connecting the reporter (e.g., Dye) to the base of a nucleotide analog can leave a residue having a terminal group attached to the base. The terminal group remaining after cleavage is dependent upon the site of the cleavage reaction. The terminal group includes at least one atom other than H. Exemplary and non-limiting examples of terminal groups include hydroxyl and sulfhydryl groups.

As used herein, the phrase "nucleotide analog" refers to a chemical compound that is structurally and functionally similar to a nucleotide and which can be recognized by a polymerase as a substrate. Nucleotide analogs include nucleotides comprising labels attached to the nucleotide via a cleavable linker and nucleotides in which the —OH group at the 3' position of the deoxyribose is capped (e.g., with a chemical moiety such as —CH$_2$OCH$_3$ or —CH$_2$CH=CH$_2$). Nucleotide analogs of this type are disclosed in U.S. Pat. No. 6,664,079 B2.

As used herein, the phrase "oligonucleotide" refers to a linear oligomer of nucleosides or analogs thereof, including deoxyribonucleosides, ribonucleosides and the like. Oligonucleotides can range in size from a few monomeric units (e.g., 3 to 4 units) to several hundred monomeric units.

As used herein, the term "label" and the term "reporter" are used interchangeably and refer to a detectable moiety (i.e., a moiety which emits a detectable signal). The moiety can be a fluorescent moiety.

As used herein, the term "quencher" refers to a moiety which reduces the signal emitted by the label or reporter when in close proximity thereto (e.g., when attached to the same compound as the label). If the label is a fluorescent moiety, the quencher can be a moiety which reduces fluorescent emissions via a fluorescence energy transfer (such as FRET) mechanism. FRET occurs between a donor fluorophore (i.e., the fluorescent label, e.g., a reporter in the FRET system which provides a detectable signal in the absence of FRET, when for example the quencher is removed, and functions as an energy transfer donor in the presence of FRET, when for example the quencher is present) and an acceptor (e.g., a quencher which in FRET functions as a non-fluorescent energy transfer acceptor) when the absorption spectrum of the quencher molecule overlaps with the emission spectrum of the donor fluorophore or when the two molecules are in close proximity. Other mechanisms of fluorescence quenching are also known and include, but are not limited to, collisional and charge transfer quenching.

As used herein, the phrase "unique label" refers to a detectable moiety that can be distinguished from other detectable moieties in the sample. For example, each of the nucleotide analogs of T, G, A and C can have a unique label. The presence of the signal associated with a given label is therefore indicative of the presence of the nucleotide analog to which it is attached. The use of unique labels therefore allows for the determination of the nucleotide analog added to the end of the extending nucleic acid during sequencing by synthesis.

As used herein, the phrase "permanent linkage" refers to a linkage that is not cleaved.

As used herein, the phrase "transient linkage" refers to a linkage that can be cleaved (e.g., a chemically labile linkage, a photo-cleavable linkage).

DNA sequencing via "sequencing by synthesis" involves the interrogation of each base on a target by primer/polymerase based synthesis of the target's complement in a stepwise manner. This technique involves the serial incorporation of a "reversible terminator" which contains a reporter and which blocks synthesis once the terminator is incorporated. The terminator contains a reporter specific for the base to which it is attached. The reporter can be a fluorescent reporter and is a detectable moiety. Termination can be reversed by the removal of a blocking group (e.g., on the 3' hydroxyl of the incorporated reversible terminator) and further extension can then be sustained. The reporter can be removed after interrogation and prior to further extension, or the reporter and blocking groups can be removed simultaneously.

Reporters that signify incorporation events can reside on the γ-position of the triphosphate where the reporter can be removed from the interrogation volume by diffusion of the resulting pyrophosphate from the extension product. Alternatively, reporters can be attached to the base. When attached to the base, the reporter must be removed in a separate step from the extension product prior to the next incorporation event in order to prevent the reporter dyes from quenching each other and to ensure that each signal can be unambiguously identified with an incorporating base. Further information is provided in Mitra, R. D. et al., "Fluorescent in situ sequencing on polymerase colonies" Analytical Biochemistry, vol. 320(1), pp. 55-65 (2003), incorporated by reference herein in its entirety. Several different approaches have been attempted for single molecule sequencing. For example, the use of a "nanopore" (i.e., a nanometer scale pore in an insulating membrane) is disclosed in Nakane et al., Condens. Matter 15 (2003) R1365-R1393. In addition, the use of a zeromode wave guide is disclosed in Levene et al., Science 299 (2003), pp. 682-686. Also, the simultaneous stepwise extension of many fragments with a dye labeled nucleotide on a flat surface is disclosed in Braslavsky et al., PNAS 100 (2003), pp. 3960-3964. Additional nucleic acid sequencing and single-molecule detection schemes are described in U.S. patent application Ser. No. 11/345.979 by McKernan et al., filed Feb. 1, 2006 and U.S. patent application Ser. No. 11/737,308 by K. J. McKernan et al., filed Apr. 19, 2007, incorporated herein by reference in its entirety for all purposes.

Figure 1:
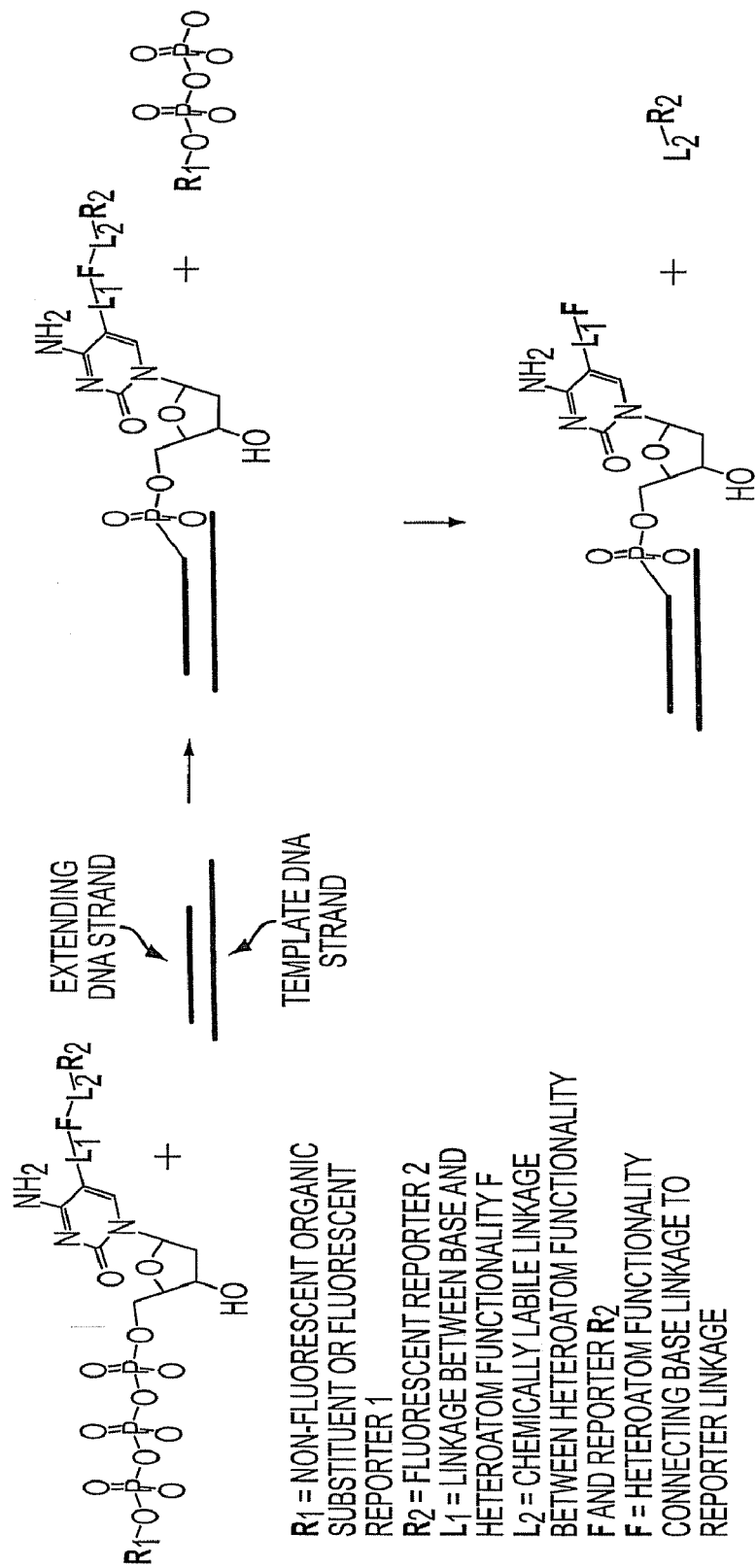
FIG. 1 is a schematic illustrating a method for the serial release of a reporter for a dual reporter system during DNA sequencing by synthesis.

The addition of a nucleotide analog having an organic substituent (e.g., a fluorescent reporter) $R_1$ attached to the γ-position of the triphosphate and a fluorescent reporter $R_2$ attached to the base is shown in FIG. 1. As shown in FIG. 1, the nucleotide analog is added to an extending DNA strand resulting in the removal of the substituent $R_1$. After the nucleotide has been added to the extending DNA strand, the linker $L_2$ and fluorescent reporter $R_2$ can be removed via cleavage of the linkage connecting $R_2$ to the base thereby allowing for a further incorporation event.

When the reporter is attached to the base, its removal during sequencing can yield a product that is not the same structure as the natural deoxynucleoside triphosphate (dNTP) substrate due, for example, to the need for linkers (e.g., $L_2$ and $L_3$ in FIG. 1) and functional groups (e.g., F in FIG. 1) that enable binding and releasing of the reporter from the base. Moreover, once the moiety is cleaved, a residue from the linker can remain attached to the base which is then incorporated into the extending double stranded DNA. Reversible terminators having residues with terminal amino groups on the base after cleavage of the reporter are disclosed in Ju et al., "Four Color DNA Sequencing by Synthesis Using Cleavable Fluorescent Nucleotide reversible Terminators," PNAS, vol. 35 U.S.C. §103(a), No. 52, pp. 19635-19640 (Dec. 26, 2006).

Figure 2A:
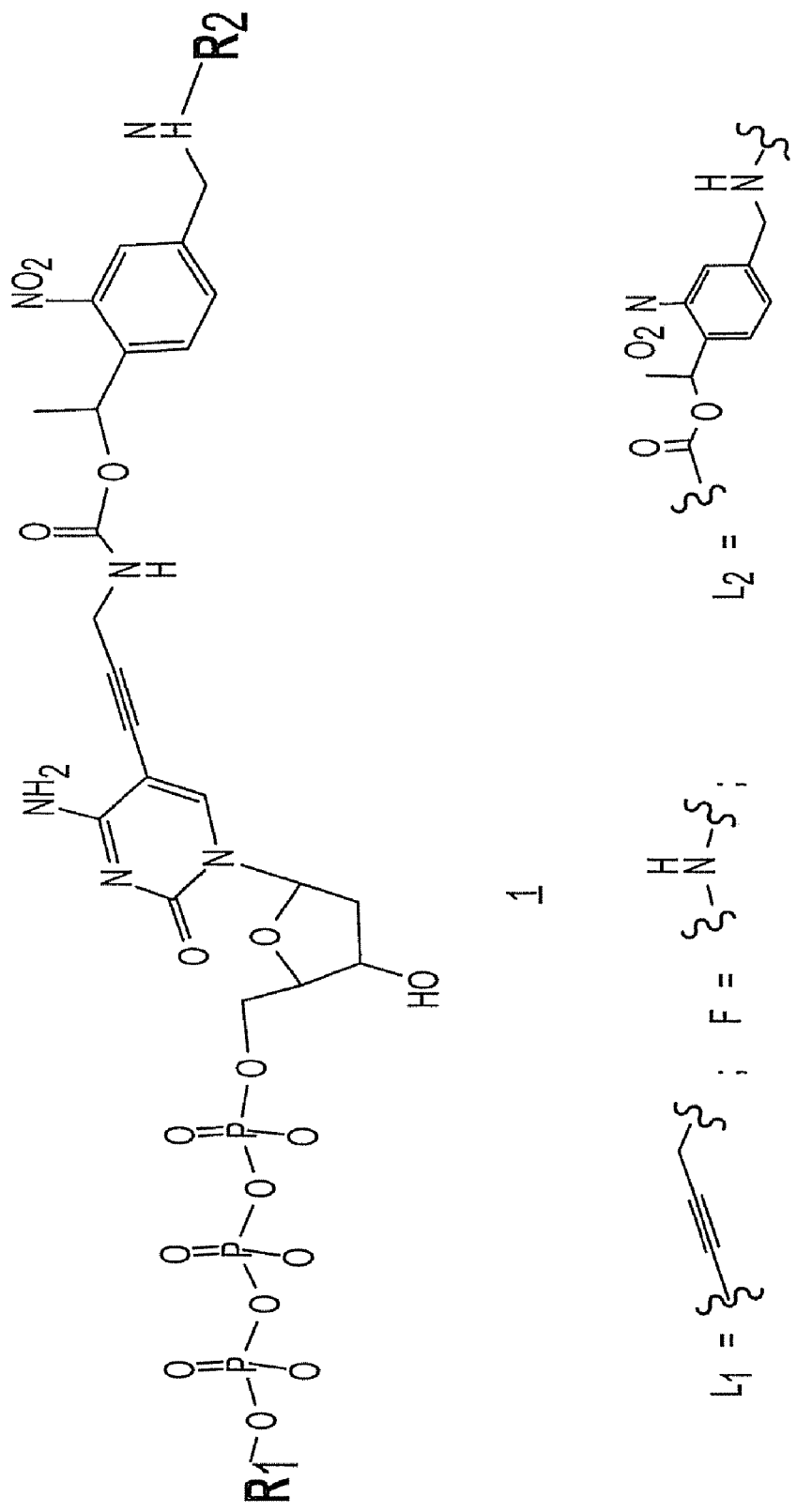
FIGS. 2A and 2B are schematics illustrating the chemical structures of two unnatural DNA substrates having photocleavable linkers.
Figure 2B:
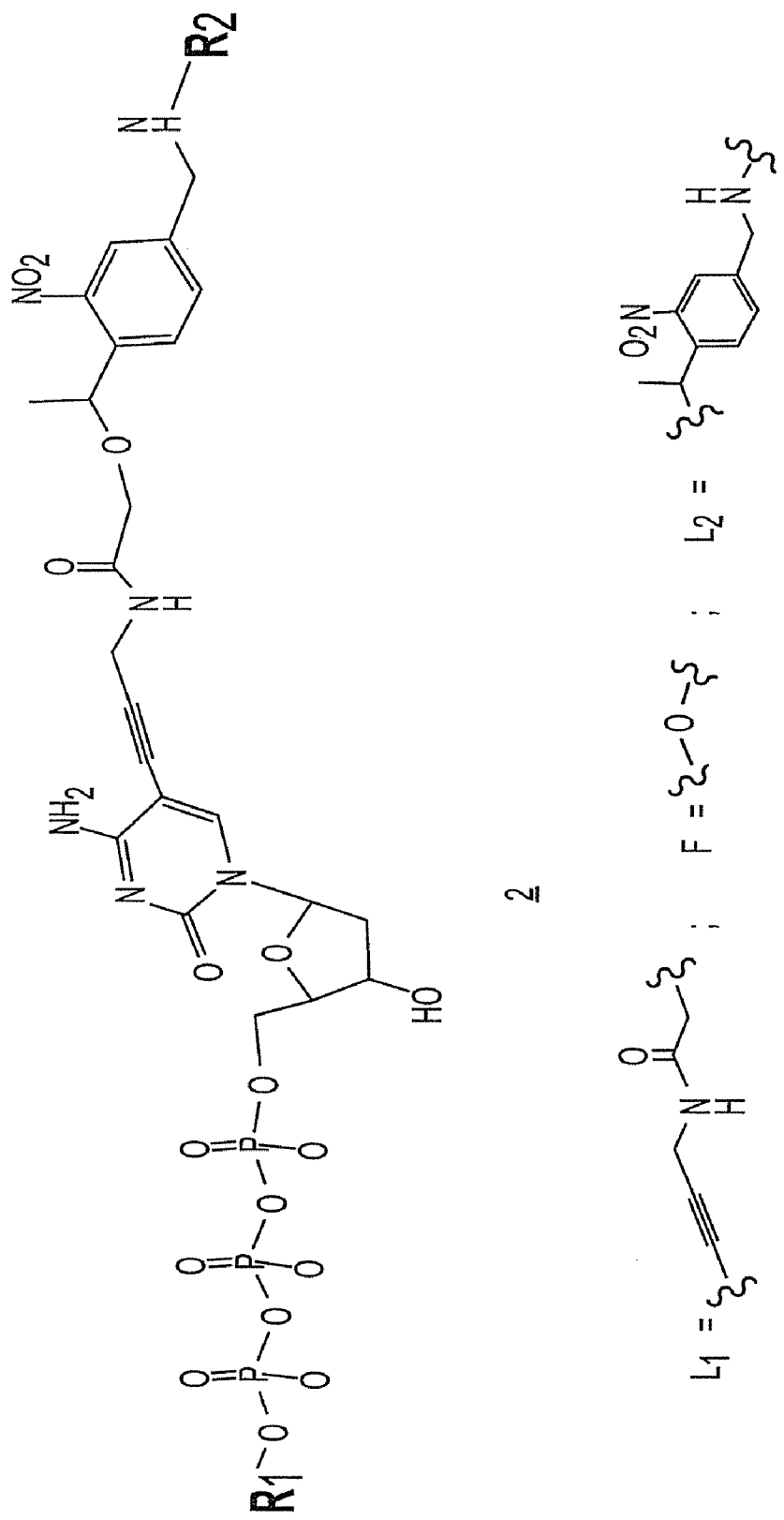

As set forth above, the reporter can be attached to the base via a cleavable linker. According to some embodiments, the linker connecting the reporter to the base can be a photo-cleavable linker. Polymerase substrates wherein the reporter is attached to the base via a photo-cleavable linker are shown in FIGS. 2A and 2B. In FIGS. 2A and 2B, F is N or O, $L_1$ is propargyl (i.e., —C—C≡C—) and $L_2$ is a photo-cleavable linker moiety represented by the structure:

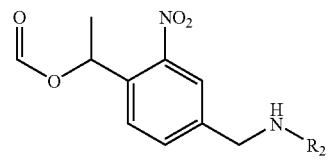

wherein $R_2$ is a fluorescent reporter.

Figure 3:
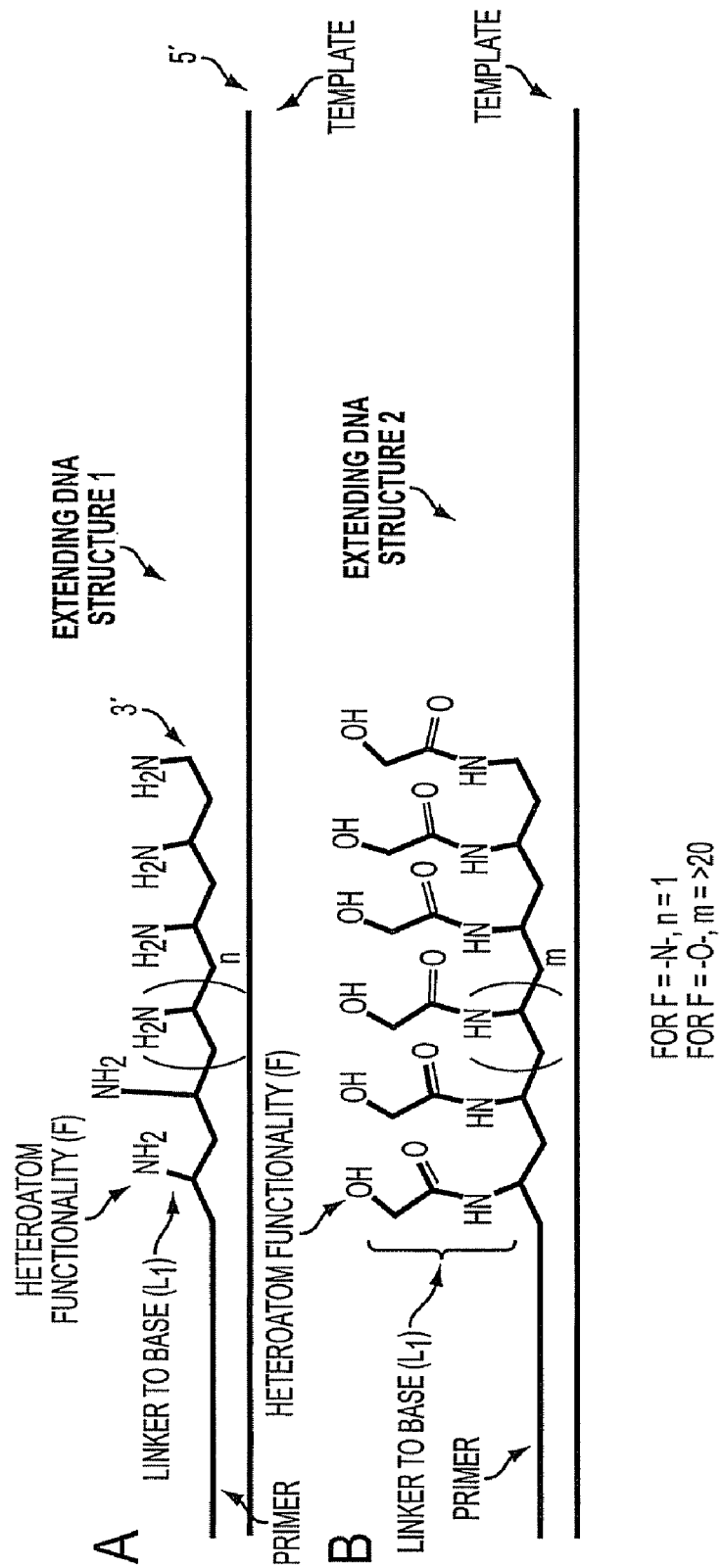
FIGS. 3A and 3B are schematics illustrating the polymerase incorporation of nucleotide analogs having amino terminal residues (FIG. 3A) and glycolate terminal residues (FIG. 3B) into an extending DNA strand over a template.
Figure 4:
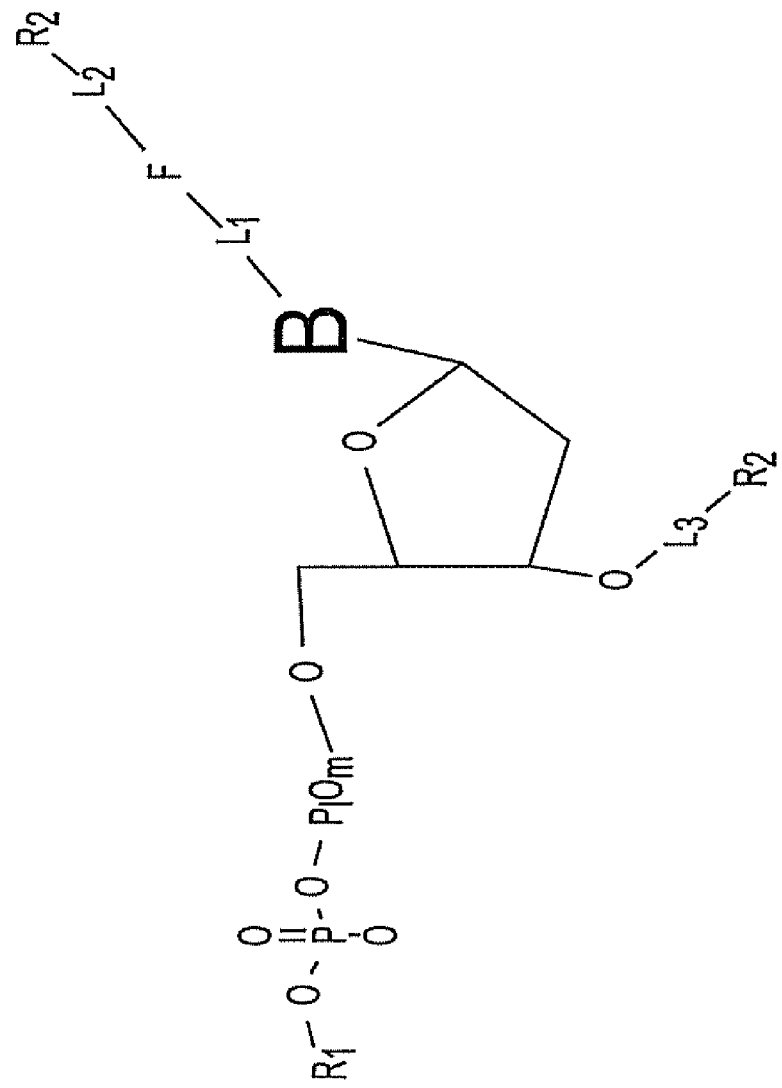
FIG. 4 is a schematic showing the general structure of a reversible terminator.

In FIG. 2A, the terminal functional group on the residue remaining after cleavage of the linkage between the reporter and the base is an amino group. When such a substrate is incorporated into an extending DNA strand (e.g., in a sequencing by synthesis method), the extending DNA would include residues having terminal amino groups as illustrated in extending DNA in FIG. 3A. As can be seen from FIG. 3A, this structure comprises amino group terminated residues on each of the bases in the extended nucleic acid strand.

Based on experiments that are described in detail below, it was discovered that certain residues remaining on the base after cleavage are more compatible with extension over the resulting double-stranded DNA than other residues. In particular, it has been discovered that linker residues in unnatural bases in the extending strand comprising terminal amino groups can severely retard incorporation of the triphosphate substrates after 8-10 incorporation events. However, when the linker residues in the unnatural bases in the extending strand are terminated with a methyl or hydroxyl-groups (as shown in extending DNA in FIG. 3B), incorporation can be sustained for at least 50 bases.

Under certain conditions (e.g., with variations of linker structure and polymerase), triphosphate nucleosides containing a free 3' hydroxyl and a linker-reporter extending off of the base will incorporate once but will fail to incorporate a second time until the linkage coming off of the base is cleaved to remove the reporter. For example, reversible terminators having free 3'-hydroxyl groups are disclosed in Wu et al., "Termination of DNA Synthesis by N6-alkylated, not 3'-O-alkylated, photo-cleavable 2'-Deoxyadenosine Triphosphates", Nucleic Acids Research (2007), 35(19), 6339-6349) and Wu et al., 3'-O-modified nucleotides as reversible terminators for pyrosequencing, Proceedings of the National Academy of Sciences of the United States of America (2007), 104(42), 16462-16467. These reversible terminators have 2-nitrobenzyl groups on the base which can be removed via UV light to restore the natural nucleotide and allow incorporation into the extending DNA strand. However, the terminating effects of the un-cleaved extended substrate on the ability of the next dNTP to incorporate are very sensitive to the structure of the linker on the base, and the polymerase.

Accordingly, a compound represented by the following formula (I) is provided:

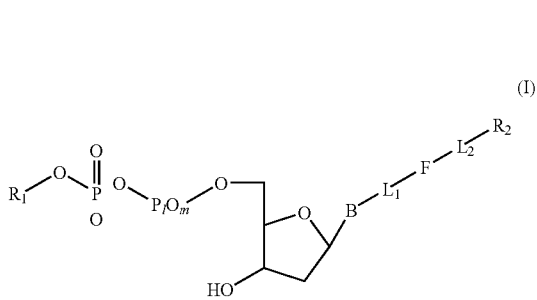

(I)

wherein:

B is a base selected from the group consisting of adenine, guanine, cytosine, uracil and thymine or their respective analogs;

$L_1$ is a group that forms a linkage to the base B and F;

F is a heteroatom that forms a linkage between $L_1$ and $L_2$;

$L_2$ is a chemically labile group with respect to F and forms a chemical linkage to reporter $R_2$;

$L_3$ is either H or a chemically labile group comprising a heteroatom which forms a chemical linkage to reporter $R_2$;

each $R_2$ is, independently, a group comprising a reporter, wherein the combination of $L_2$ and $R_2$ prevents the template directed polymerase incorporation of the compound onto the 3' end of an extending oligonucleotide onto which a compound of the formula (I) has been incorporated;

$R_1$ is a neutral substituent, selected from substituted or un-substituted alkyl, substituted or unsubstituted aromatic, substituted or un-substituted heterocycle, substituted or unsubstituted aromatic heterocycle substituents, or (anionic or cationic forms thereof, where the substituent suppresses the template directed polymerase incorporation rate of the nucleoside triphosphate onto the 3' end of an extending oligonucleotide prior to the cleavage of $L_2$-$R_2$ from the previous incorporation event;

l is an integer; and m=3l−1.

According to some embodiments, cleavage of the chemically labile group $L_2$ leaves a linker residue moiety having a terminal group attached to the base. According to some embodiments, the terminal group of the residue is not an amino group. According to some embodiments, the terminal group of the residue is an hydroxyl group. According to some embodiments, l is 2, 3, or 4.

As set forth above, $L_3$ can be H (i.e., the compound can have a free or unblocked 3' hydroxyl group). In contrast to the reversible terminators where the 3'-hydroxyl is blocked and must be removed prior to the next incorporation event, reversible terminators with unblocked 3'-hydroxyl groups do not require a separate unblocking step. The substrates with blocked 3'-hydroxyl groups can also be poor substrates for polymerases and the rates of incorporation can be very slow, requiring elevated substrate concentration and long reaction times.

Accordingly, a compound is also provided which has a structure represented by the following formula (II):

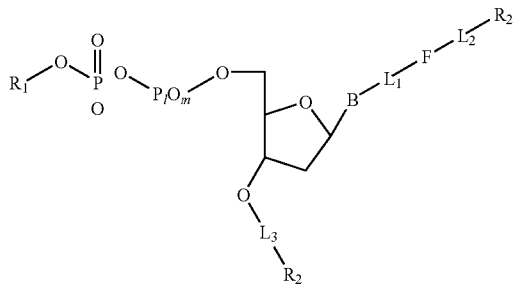

(II)

wherein B, $R_1$, $L_1$, F, $L_2$, $R_2$, l and m are defined as set forth above for formula (I).

For these compounds, the 3'-hydroxyl is always free and the selectivity of the "termination" (i.e., the suppression of incorporation of the next base until the linker $L_2$-$R_2$ is cleaved) can be optimized by altering structures at $L_2$ and $R_1$.

In the compounds of formulae (I) and (II) above: F can be a linkage which results in an hydroxyl terminating residue upon cleavage; $L_2$ and $L_3$ can be a chemically cleavable group such as a thioacetal, a thioester, or an ester; $L_2$-$R_2$ is a linker-reporter combination wherein the presence of the linker and/or reporter on the incorporated base in the extending strand suppresses the polymerase catalyzed incorporation of the next base which contains a similar linker-reporter $L_2$-$R_2$; and $R_1$ is a group bound to the γ-phosphate of a triphosphate or the δ-phosphate of a tetraphosphate which acts to suppress the rate of incorporation of the next nucleotide when the previous nucleotide incorporated still contains $L_2$-$R_2$.

As set forth above, $R_1$ is a group that suppresses the template directed polymerase incorporation rate of the nucleoside triphosphate onto the 3' end of an extending oligonucleotide prior to the cleavage of $L_2$-$R_2$ from the previous incorporation event. According to some embodiments, $R_1$ can be a substituted or unsubstituted hydrocarbon group. Non limiting examples of substituted or unsubstituted hydrocarbon groups include, (i) substituted or un-substituted alkyls, substituted or unsubstituted aromatics, substituted or un-substituted heterocycles, substituted or unsubstituted aromatic heterocycles, or (ii) neutral, anionic, or cationic forms of (i).

The structures of four exemplary reversible terminator bases having free 3' hydroxyl groups are shown in FIGS. 5A-5D. The variables in FIGS. 5A-5D are defined as follows: $L_2$ is a chemically labile linking group such as C(O)S—, C(O)O—, CH(SMe)phenyl-, [RO]$_2$P(O)S—; $R_2$ is a group containing a reporter moiety that in combination with $L_2$ suppresses the incorporation rate of the nucleoside triphosphate during polymerase dependent template directed DNA synthesis when the preceding nucleotide contains a group $L_2$-$R_2$ with the same or similar structure, but allows incorporation when the group on the preceding nucleotide has been cleaved at $L_2$, resulting in cleavage residue F; and $R_1$ is an organic substituent selected from (i) substituted or un-substituted alkyls such as methyl, propargyl or benzyl, substituted or unsubstituted aromatics such as phenyl, methoxyphenyl, or naphthyl, substituted or un-substituted heterocycles such as tetryhydropyrrole or piperazine, substituted or unsubstituted aromatic heterocycles such as quinolyl, methylimidazolyl, pyridyl, imidazolyl, or benzoimidazolyl or (ii) neutral, anionic (e.g., benzenesulfonate), or cationic (e.g., trimethylammonium, phenyl or imidazolium) forms of (i).

Figure 6:
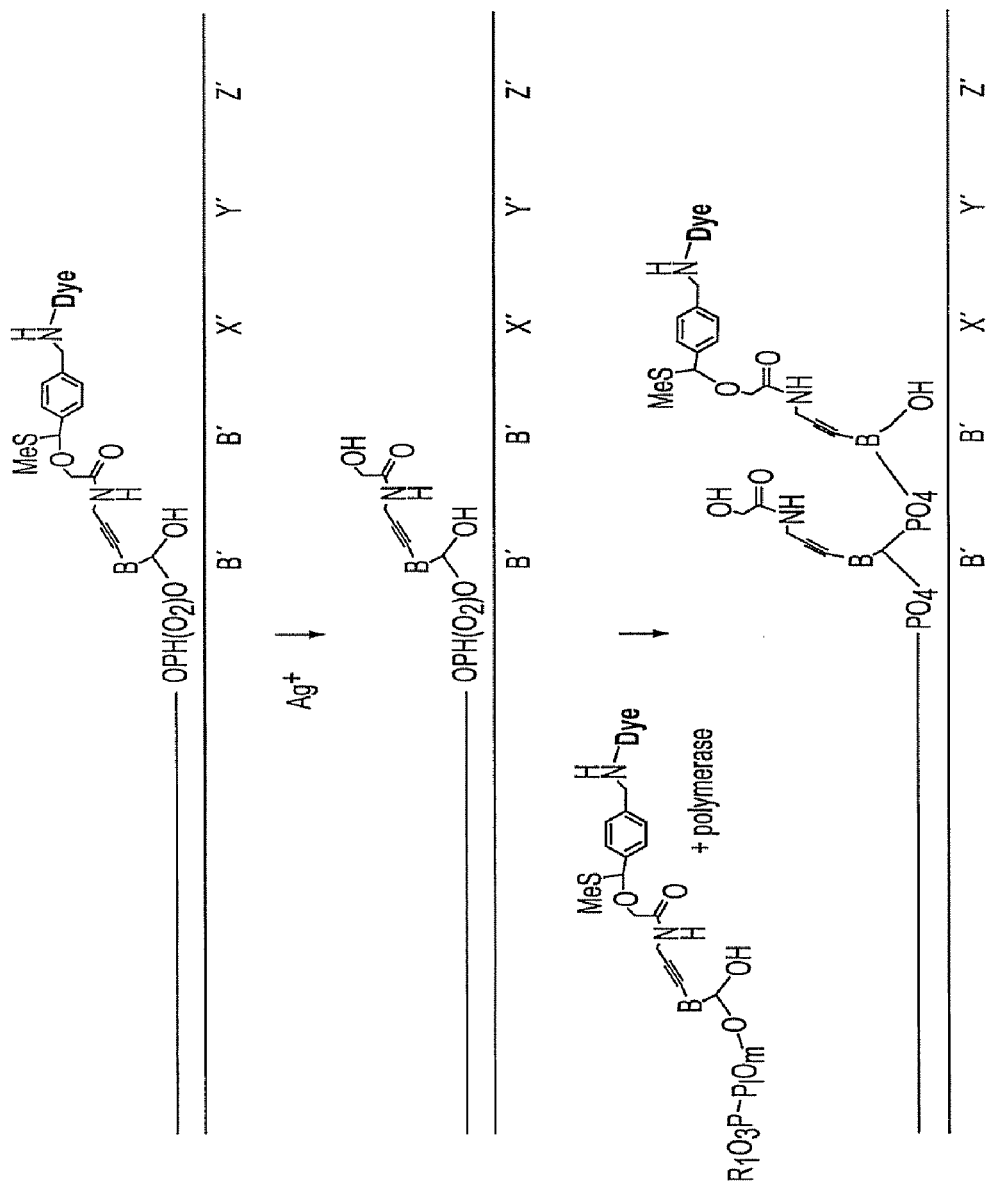

An example of the use of a reversible terminator having a free 3'-hydroxyl group is shown in FIG. 6. In FIG. 6, the cleavable group $L_2$ is thioacetal, the linker residue $L_1$-F from the cleavage is —C≡C—CH$_2$—NH—C(O)—CH$_2$—OH, and the moiety which suppresses the incorporation of the next nucleotide is the substituted aromatic structure. The thioacetal group shown in FIG. 6 is cleavable by a silver ion.

FIG. 7 shows the structure of a reversible terminator having a free 3' hydroxyl group wherein the cleavable group linking the reporter to the base is a thiocarbonate group. The thiocarbonate group is also cleavable by a silver ion. FIG. 7 also illustrates the chemistry involved in the silver ion chemical cleavage of the substrate after incorporation into a DNA strand.

FIG. 8 shows the structure of a polymerase substrate wherein the cleavable group $L_2$ is a thioacetal group. The thioacetal group is also cleavable by a silver ion. FIG. 8 also illustrates the chemistry involved in the silver ion chemical cleavage of the substrate after incorporation into a DNA strand.

FIGS. 9A-9D illustrate the structures of polymerase substrates having different cleavable linkers between the base and the reporter that can be cleaved by a basic compound (e.g., ammonia) where F=oxygen atom and $L_1$=propargyl.

FIGS. 10A-10D are schematics illustrating the structure of silver ion cleavable linkers with dye labeling capabilities that can be cleaved to yield hydroxyl or amine groups at the terminal end of the linker residue.

FIG. 11 is a schematic illustrating the use of silver ion cleavable groups which leave a phosphate terminal group on the residue. In the structure shown in FIG. 11, the benzene ring to which the "DYE" is attached can be unsubstituted (as shown) or substituted (not shown).

The label that is attached to the nucleotide analogue can be a fluorescent moiety. The fluorescent moiety can be a moiety selected from the group consisting of fluorescein, rhodamine, cyanine, and/or bodipy dyes.

According to some embodiments, the unique label is attached through a cleavable linker to a 5-position of cytosine or thymine or to a 7-position of deaza-adenine or deaza-guanine. The unique label can also be attached through a cleavable linker to another position in the nucleotide analogue as long as the attachment of the label is stable during the polymerase reaction and the nucleotide analog can be recognized by polymerase as a substrate.

The nucleotide analogues disclosed herein can be used for detection of single nucleotide polymorphisms, genetic mutation analysis, methylation detection, serial analysis of gene expression, gene expression analysis, identification in forensics, genetic disease association studies, DNA sequencing, RNA sequencing, genomic sequencing, translational analysis, and transcriptional analysis.

Accordingly, a method of sequencing a nucleic acid is also provided which comprises:

(a) hybridizing a primer to a target polynucleotide to form a primer-target duplex, wherein the target polynucleotide is attached to a solid support at the 3' or 5' end;

(b) contacting the primer-target duplex with a polymerase and one or more nucleotide analogs to incorporate a nucleotide analog onto the 3' end of the primer thereby forming an extended primer strand, wherein the incorporated nucleotide analog terminates the polymerase reaction and wherein each of the one or more nucleotide analogs comprises: (i) a base selected from the group consisting of adenine, guanine, cytosine, thymine, uracil and their analogs; (ii) a label attached to the base or analog thereof via a cleavable linker; (iii) a deoxyribose; (iv) three or more phosphate groups, wherein the label is unique for the base and wherein the linker and/or the label inhibits the template directed polymerase incorporation of a further nucleotide analog onto the extended primer strand; and (v) an organic moiety on the terminus of the polyphosphate, wherein the presence of the moiety inhibits incorporation of the next nucleotide analog prior to cleavage of the organic moiety from a previous incorporation of (ii) but allows the incorporation of the next nucleotide analog after cleavage of the organic moiety from a previous incorporation of (ii).

(c) washing the surface of the solid support to remove unincorporated nucleotide analogs;

(d) detecting the unique label attached to the just-incorporated nucleotide analog to thereby identify the just-incorporated nucleotide analog;

(e) cleaving the cleavable linker between the just incorporated nucleotide analog and the unique label thereby allowing the incorporation of a further nucleotide analog onto the extended primer strand;

(f) washing the surface of the solid support to remove cleaved compound fragments; and (e) repeating steps (b), (c), (d), (e) and (f).

Each of the one or more nucleotide analogs can have a structure represented by formula (I) or formula (II) above. The one or more nucleotide analogs may comprise: A first nucleotide analog wherein B is adenine having a first label; a second nucleotide analog wherein B is guanine having a second label; a third nucleotide analog wherein B is cytosine having a third label; and a fourth nucleotide analog wherein B is thymine having a fourth label. The labels may be fluorescent labels. One of skill in the art would understand the use of uracil as a fourth label for RNA sequencing and analyses.

Non-limiting examples of the DNA polymerase include Thermo Sequenase, Taq FS DNA polymerase, T7 DNA polymerase, Therminator, Therminator II, and Vent (exo-) DNA polymerase. The structure of the nucleotide analog can be optimized for the polymerase used for extension. Structure optimization can include the structure and selection of substituents for $R_1$ and $L_2$ and in the selection of the "Dye" (detection moiety).

The fluorescence emission from each specific dye can be detected using a fluorimeter that is equipped with an accessory to detect fluorescence from a solid surface. For large scale evaluation, a multi-color scanning system capable of detecting multiple different fluorescent dyes (e.g., 500 nm-700 nm, 400 nm-800 nm and so on) can be used.

The nucleotide analogs described herein can be used in DNA and RNA sequencing strategies that utilize single molecule detection, real time DNA and RNA sequencing, or any other technique where the DNA or RNA sequence is determined serially by interrogation of each incorporation event with a base labeled reporter, followed by chemical, thermal, enzymatic or other physical cleavage of the reporter prior to the next incorporation event.

The methods and compounds described herein can be used to sequence amplified targets as well as single molecules.

EXAMPLES

Aspects of the present teachings may be further understood in light of the following examples, which should not be construed as limiting the scope of the present teachings in any way. Although the examples are for DNA nucleotides, RNA nucleotides are also envisioned as would be understood to one of skill in the art.

In order to determine if a polymerase would continue to extend an unnatural DNA (i.e., a DNA including moieties not present in natural DNA) comprising residues having amino groups, an experiment was designed using aminopropargyldUTP (deoxyuridine triphosphate) and dCTP (deoxycytidine triphosphate) which yields extended DNA having residues with terminal amino functional groups on the incorporated dUTP moieties. The dUTP used is represented by the formula:

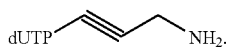

The experiment was conducted using an FAM (i.e., 6-carboxyfluorescein) labeled primer over an $(AAG)_{14}$ [SEQ ID NO: 1] template.

As illustrated in FIG. 12B, electrophoresis of the product shows poor extension as illustrated by the multiple FAM peaks (dark peaks, light peaks are a size standard) in the electropherogram trace which demonstrate failure to sustain the synthesis. These results indicate no extension beyond about 14 bases of the 42 base target template.

This contrasts with the use of methylpropynyl dUTP and dCTP over the same template which shows extension to a single product as illustrated in the electropherogram of FIG. 12A. It should be noted that the size differences in the electropherograms of FIG. 12A and FIG. 12B results from the large apparent size of the amino fragments due to low mobilities imparted to the fragments by the positively charged amino groups While not wishing to be bound by theory, it appears that the amino-group in the residue attached to the incorporating base interferes with the polymerase enzyme activity. A neutral substrate was therefore designed having a structure as set forth below and in FIG. 2B:

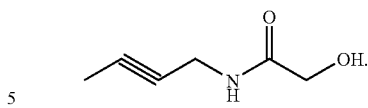

Figure 5B:
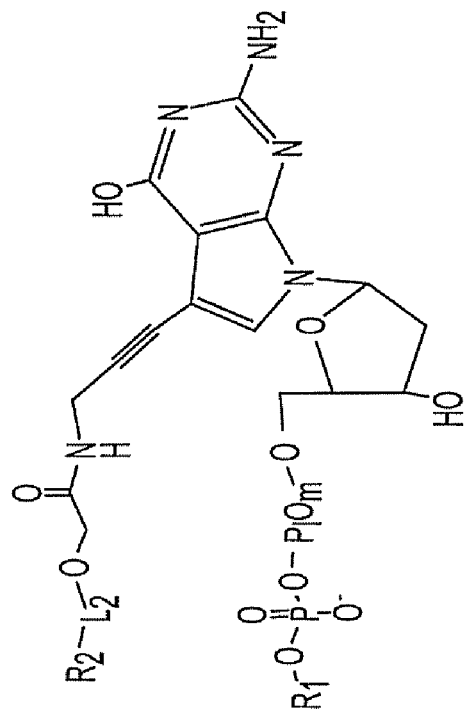
FIGS. 5A-5D are schematics illustrating exemplary chemical structures of four reversible terminator bases that have free 3' hydroxyl groups.
Figure 5A:
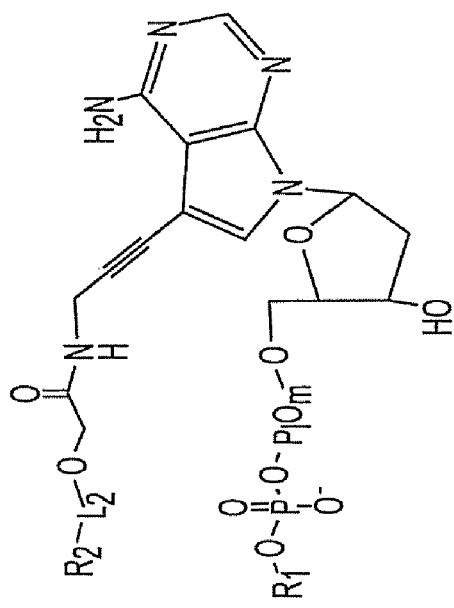
Figure 5D:
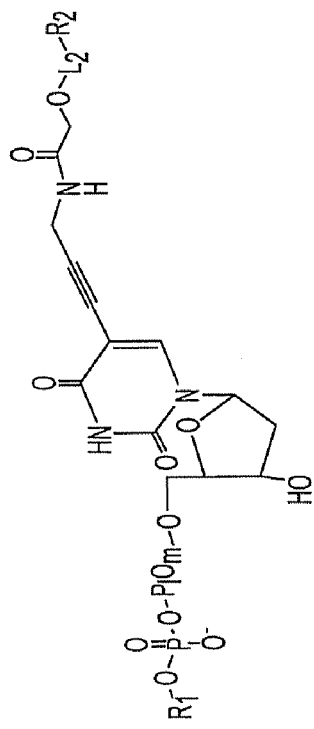
Figure 5C:
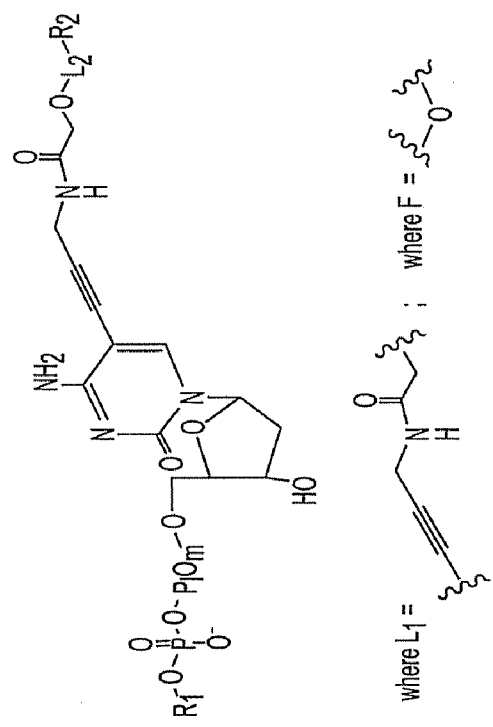

The structure of the dUTP analog used in this experiment is set forth in FIG. 5D. This nucleotide analog therefore has an hydroxyl terminal moiety attached to the base.

These substrates were tested against the same template/primer system used in the experiments shown in FIGS. 12A and 12B {i.e., Klenow enzyme at 37° C. for 1 minute over an $(AAG)_{14}$ [SEQ ID NO: 1] template}. The concentration of the nucleotides for this experiment was 5 μM. The results of this experiment are summarized in the electropherogram of FIG. 13C.

Similar experiments were conducted over the same template for natural dCTP/dTTP, with results shown in the electropherogram of FIG. 13A, and the methylpropynyl analogs of these substrates, with results shown in the electropherogram of FIG. 13B.

The electropherogram of FIG. 13C shows excellent synthesis of the extension product for the nucleotide analogs having an hydroxyl terminal moiety attached to the base. Moreover, the electropherograms of FIGS. 13A, 13B and 13C show that the extension in each case goes to completion with similar efficiencies. Therefore, hydroxyl terminal residues on the base of the nucleotide analogs do not appear to interfere with polymerase directed extension of the nucleic acid strand over a template.

The use of a glycolate linker enables photo-chemical cleavage and provides a practical synthesis route to these compounds. The functionalized substrate is active to photo-chemical cleavage and the resulting product has an hydroxyl terminal residue which does not interfere with enzymatic synthesis of DNA on the extending strand.

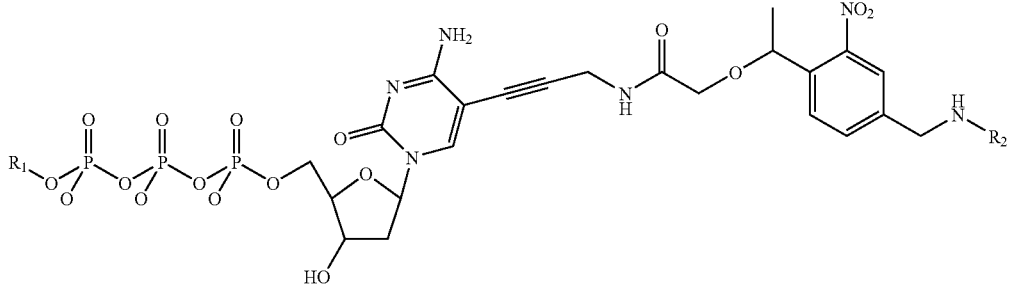

wherein F is O, $L_1$ is propargylamide (i.e., —C—C≡C—C—NH—C(O)—C—), and $L_2$ is a moiety represented by the structure:

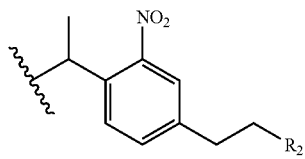

wherein $R_2$ is a fluorescent reporter. This structure corresponds to the general structure of FIG. 1 wherein $L_1$-F is glycolate. This structure therefore yields a glycolate linkage instead of an amino-linkage upon photo-chemical cleavage.

To conduct these experiments, a dUTP substrate having the following moiety attached to the 5-position of the base was synthesized.

Additional experiments were conducted to determine the effects of a γ-phosphate substituent (i.e., $R_1$) and a substituent on the base (i.e., -$L_1$-F-$L_2$-$R_2$) on the termination of nucleotide analogs having a free 3' hydroxyl group.

FIGS. 14 and 15 are schematics illustrating the polymerase directed addition of a nucleotide analog having a γ-phosphate substituent ($R_1$) and a -linker- Dye ($L_2$-$R_2$) substituent on the base to the 3' end of a nucleic acid over a template, where -$L_2$-represents any combination of functional linkages including, but not limited to, ester, amide and benzylic ether linkages between the linker and Dye that will maintain enzyme activity and enable directed cleavage of the dye from the linker after enzymatic incorporation of the nucleotide. FIG. 14 shows a first nucleotide analog being incorporated into the nucleic acid. As illustrated in FIG. 15, when $R_1$ is H, a second nucleotide analog can be added to the 3' end of the nucleic acid resulting in primer extension. However, when $R_1$ is a hydrocarbon group (e.g., methyl, propargyl or benzyl), the second nucleotide analog is not added to the 3' end of the nucleic acid until the -$L_2$-$R_2$ substituent is cleaved from the base. As shown in FIG. 15, $R_1$ can be H or $R_1$ can be a hydrocarbon or a heteroatom substituted hydrocarbon.

FIGS. 16A-16D are schematics showing the chemical structures of four different non-cleavable nucleotide analogs, dATP-L-Cy5, dCTP-L-Cy3, Benz-dATP-L-Cy5, and HC-dATP-L-Cy5 respectively. The dATP-L-Cy5 (FIG. 16A) and dCTP-L-Cy3 (FIG. 16B) analogs do not have a γ-phosphate substituent (i.e., $R_1$ is H) whereas the Benz-dATP-L-Cy5 analog shown in FIG. 16C has a benzyl group as a γ-phosphate substituent and the HC-dATP-L-Cy5 analog shown in FIG. 16D has a hydrocarbon (HC) group as a γ-phosphate substituent. The hydrocarbon group can be a substituted or unsubstituted alkyl or aromatic group, and the substituents can be heteroatoms that result in neutral, cationic or anionic groups. The R substituent on the phenyl ring can be hydrogen, a hydrocarbon, a cationic group or an anionic group.

Figure 16B:
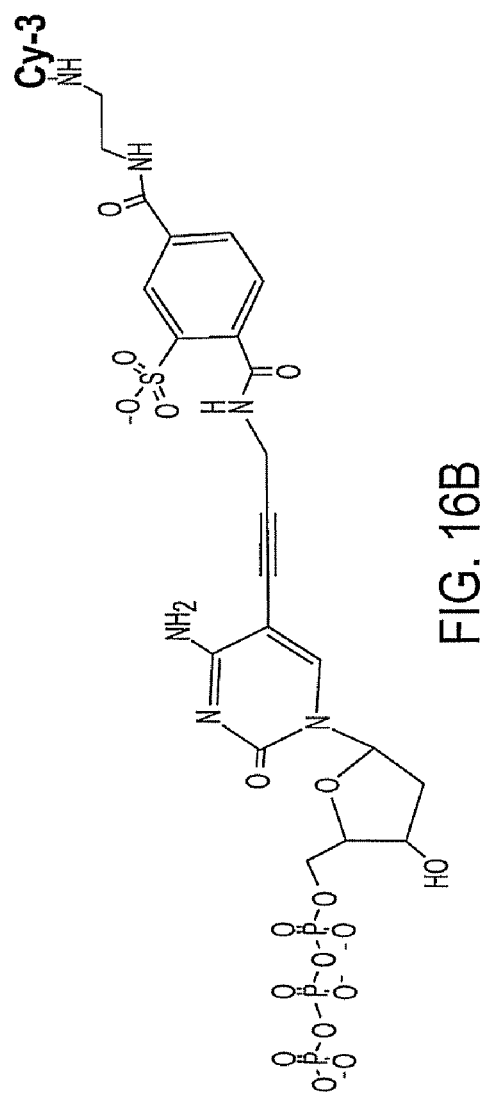

FIGS. 17A and 17B are electropherograms illustrating the termination effect of a γ-phosphate benzyl substituent on the nucleotide analog. The template used in this experiment includes the following sequence:

```
3' ACATTTGCTGCCGGTCAGTGT . . . 5'   [SEQ ID NO: 2]
``` wherein the underlined portion of the sequence indicates where the dye-labeled primer hybridized. The electropherogram of FIG. 17A shows the incorporation of dATP-L-Cy5 (FIG. 16A) after the incorporation of dCTP-L-Cy3 (FIG. 16B). In particular, the signals from both Cy-3 and Cy-5 can be seen in the electropherogram of FIG. 17A. In FIG. 17A, a relatively small peak can be observed for the first dC incorporation, a big peak can be observed for the unsubstituted dA incorporation, and a third peak can be observed for an additional dC incorporation. The electropherogram of FIG. 17B shows that Benz-dATP-L-Cy5 (FIG. 16C) is not incorporated after the incorporation of dCTP-L-Cy3 (FIG. 16B). In particular, only the signal for Cy-3 can be seen in the electropherogram of FIG. 17B.

FIGS. 18A and 18B are electropherograms illustrating that a nucleotide analog which does not have a γ-phosphate substituent can be incorporated after a nucleotide analog having a γ-phosphate benzyl substituent (i.e., the nucleotide analog of FIG. 16C). The template used in this experiment includes the following sequence:

```
3' ACATTTGCTGCCGGTCATGTC . . . 5'   [SEQ ID NO: 3]
``` wherein the underlined portion of the sequence indicates where the dye-labeled primer hybridized. Compared to the template used in the experiments of FIGS. 17A and 17B, for this template the first two bases on the template 5' of the primer have been switched to verify that the Benz-dATP-L-Cy5 was in fact a substrate for the polymerase. The electropherogram of FIG. 18A shows the incorporation of dCTP-L-Cy3 (FIG. 16B) after the incorporation of dATP-L-Cy5 (FIG. 16A). In particular, the signals from both Cy-3 and Cy-5 can be seen in the electropherogram of FIG. 18A. The electropherogram of FIG. 18B shows that dCTP-L-Cy3 (FIG. 16B) is incorporated after the incorporation of Benz-dATP-L-Cy5 (FIG. 16C). In particular, the signals from both Cy-3 and Cy-5 can be seen in the electropherogram of FIG. 18B. As can be seen from FIG. 18B, the Benz-dATP-L-Cy5 is readily incorporated followed by the incorporation of dCTP-L-Cy3. At this point, incorporation of additional nucleotide analogs stops due to the presence of the linker from the incorporated dCTP-L-Cy3 in the extended primer.

FIG. 19 is a schematic illustrating the use of reversible terminators having silver ion cleavable linkers between the dye and the base wherein terminator activity is selectively controlled by the presence of a γ-phosphate substituent ($R_1$) and the Linker group (L) linking the base of the nucleotide analog to the dye. As shown in FIG. 19, silver ion cleavage yields a linker residue on the base having a phosphate terminal group and phosphatase cleavage subsequently yields a propargyl alcohol residue on the base. It has been found that the propargyl residue remaining on the base after cleavage does not interfere with further extension of the nucleic acid.

FIGS. 20A and 20B are electropherograms showing incorporation data for a 31 p(dA) template (i.e., 31 contiguous dA's) using Therminator II polymerase with dTTP (FIG. 20A) and a dUTP nucleotide analog having a propargyl alcohol residue on the base (FIG. 20B). FIGS. 20A and 20B demonstrate the ability of polymerases to incorporate nucleotide analogs having a propargyl alcohol residue on the base. In particular, more than 31 peaks are observed in both FIG. 20A for dTTP and in FIG. 20B for the dUTP nucleotide analog having a propargyl alcohol residue on the base indicating incorporation over the length of the template.

FIGS. 21A-21D are electropherograms showing the termination properties of γ-phosphate substituted dUTP analogs having an O-propargyl-S-substituent at the 5 position over a p(dA) template. The nucleotide analog used in these experiments had a general structure as set forth below:

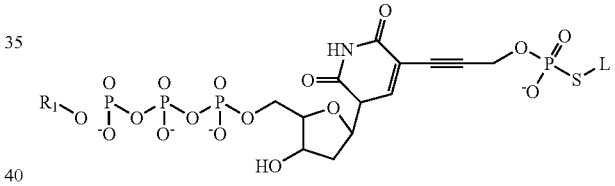

wherein $R_1$ is a methyl group. The substrate concentration was 1 μM. FIG. 21A is an electropherogram for the primer. FIGS. 21B-D are the electropherograms after 10, 30 and 60 minutes of extension, respectively. As can be seen from FIGS. 21A-21D, the presence of the γ-phosphate substituent and the O-propargyl-S-substituent at the 5 position prevents the extension of the nucleotide analog over the p(dA) template. In particular, as can be seen from FIG. 21B, extension to the first p(dA) is almost complete after 10 minutes. However, even after one hour (FIG. 21D), there has been no observable incorporation of the nucleotide analog onto the second p(dA).

FIGS. 22A-22D are electropherograms showing the mis-incorporation properties of γ-phosphate substituted dUTP analogs having an O-propargyl-S-substituent at the 5 position and a benzyl group as a γ-phosphate substituent. The nucleotide analog used in these experiments had the same general structure as set forth above in the description of FIGS. 21A-21D. For these experiments, all reactions were conducted for 10 minutes at a substrate concentration of 1 μM using $Mg^{2+}$. Two templates were used:

```
                                         [SEQ ID NO: 4]
5' (BIO-TEG)(C18)(C18)CCCCCCGTGTGTGCTAAACTGGCCGTCG
TTTTACA 3'
``` which is referred to as the AA template and

```
5' (BIO-TEG)(C18)(C18)CCCCCCGTGTGTGCTANACTGGCCGTCG
TTTTACA 3'
```
[SEQ ID NO: 5]

wherein N can be G, C or T, which is referred to as the NA template (i.e., the GA, CA or TA templates). The primer used was:

```
5'-(6-FAM)TGTAAAACGACGGCCAGT 3'.    [SEQ ID NO: 6]
```

FIG. 22A is the electropherogram for the primer. As can be seen from FIGS. 22B-D, the γ-phosphate substituted dUTP analog having an O-propargyl-S-substituent at the 5 position is incorporated into the AA template (FIG. 22B) but not into the GA template (FIG. 22C) or the TA template (FIG. 22D). Moreover, the γ-phosphate substituted dUTP analog is not mis-incorporated over the dG or dT in the GA and TA templates, respectively.

FIGS. 23A-23C are electropherograms and a schematic showing polymerase incorporation of a nucleotide analog and Ag$^+$ and phosphatase cleavage reactions. FIG. 23A shows the incorporation of dU onto a primer-target duplex. FIG. 23B shows a nearly quantitative cleavage of the linker with silver ions to the phosphate wherein the peak can be seen to have shifted to the left due to the effect of the loss of the large linker group at the end of the extended fragment. FIG. 23C shows the loss of the phosphate group from the fragment by treatment with Calf Intestine Phosphatase wherein the peak can be seen to have shifted to the right due to the loss of the negatively charged phosphate group upon cleavage by the phosphatase.

ADDITIONAL EXAMPLES

Example 1

Synthesis of propargyl ester of phosphorothiolate linker (8) (FIG. 24). Thiophosphoryl trichloride (4) (4.7 mL) was added drop-wise to a cooled (−15° C.) solution of triethyl phosphate (40 mL) and lutidine (8.7 mL) under argon. Propargyl alcohol (1.7 mL) was then added drop wise and stirred for 1 hr. at −5° C. After cooling to −15° C., the reaction was quenched with 0.5 M tetraethylammonium bicarbonate (TEAB) (100 mL) and stirred for 6 hours at room temperature. The solution was washed with dichloromethane (DCM) two times, and the aqueous phase was concentrated yielding (5), which was used without further purification. To 0.76 g of (5) in MeOH (10 mL) and water (1 mL) was added methyl-3-(bromomethyl)benzoate (6) (0.23 g). After stirring for 2 hr. at room temperature, the reaction mixture was concentrated and the residue was taken in DCM and extracted with water. The DCM layer was concentrated and purified by silica gel column chromatography affording desired pure compound (7). A solution of 1:1 ethanol:ethylene diamine (5 mL) was added to 0.1 g of (7), the reaction was stirred overnight at 90° C. under dry argon, and then evaporated to dryness under high vacuum. The residue was dissolved in 5 mL of methanol, and treated with 0.5 mL of ethyl trifluoroacetate. After 3 hr. at room temperature, the reaction mixture was evaporated to dryness, and purified by column chromatography. Factions containing (8) were identified by mass spectrometry, combined and evaporated to dryness.

Example 2

Synthesis of dU-5'-monophosphate (10) (FIG. 25). To a solution of (8) (55 μmol) in DMF (0.6 mL) was added 22 mg of CuI (115 μmol) followed by 44 μL of triethylamine (TEA) (322 μmol) under an argon atmosphere. After all of the CuI had dissolved, 80 μL of a 250 mM solution of Iodo dUMP (1) (20 μmol) in DMF was added followed by 23 mg of Pd(PPh$_3$)$_4$ (20 μmol). After stirring overnight at room temperature under argon the reaction was diluted with 14 mL of 100 mM TEAA buffer, the suspension was filtered and the supernatant concentrated. The residue was purified by reverse phase HPLC using a triethylammonium acetate (TEAA)/acetonitrile gradient. Fractions containing (10) were further purified by anion exchange HPLC using a TEAB/acetonitrile gradient. M/S: (M−H)−729.2

Example 3

Synthesis of dC 5'-monophosphate (12) (FIG. 26). (12) was prepared from (11) and (8) in a similar manner compared to the synthesis of (10) in Example 2.

Example 4

Synthesis of dA 5'-monophosphate (14) (FIG. 27). (14) was prepared from (13) and (8) in a similar manner compared to the synthesis of (10) in Example 2.

Example 5

Synthesis of dG 5'-monophosphate (16) (FIG. 28). (16) was prepared from (15) and (8) in a similar manner compared to the synthesis of (10) in Example 2.

Example 6

Synthesis of methylpyrophosphate (19) (FIG. 29). 9.1 grams (10 mmol) of tris(tetrabutylammonium)pyrophosphate (18) were dissolved in 4.5 mL of acetonitrile and treated with 1.86 grams (10 mmol) of the methyltosylate (17). After 30 minutes the reaction was diluted to 100 mL with water and purified on a Dowex 1X8 200 column, equilibrated with 300 mmol tetraethyl ammonium bicarbonate (TEAB), and eluted with a TEAB gradient. The fractions were analyzed for phosphate using a 20 μL portion of each fraction, which was added to 300 μl of 0.5 N HCl in a 13 mm by 100 mm teat tube and heated to a boil; 600 μl of 0.42% solution of ammonium molybdate tetrahydrate in 1 N H$_2$SO$_4$ and 100 μL of a 10% ascorbic acid solution were added to each tube, heated to a boil and then placed in a 40° C. heating block. The tubes that developed blue indicated a phosphate containing fraction. A 2 mL sample from each of these fractions was stripped and examined by 31 PNMR for mono-substituted pyrophosphate (31 P NMR D2O (no reference) −8.06 ppm, 2H, dd, J1=63.19, J2=24.6).

Example 7

Synthesis of benzylpyrophosphate (21) (FIG. 30). 9.1 grams (10 mmol) of tris(tetrabutylammonium) of pyrophosphate (18) was dissolved in 4.5 mL of acetonitrile and treated with 1.71 benzyl bromide (20). After 30 minutes the reaction was diluted to 100 mL with water and purified on a Dowex 1X8 200 column, equilibrated with 300 mmol tetraethyl ammonium bicarbonate (TEAB), and eluted with a TEAB gradient. The fractions were analyzed for phosphate using the procedure shown in Example 6. A sample from each of these fractions was stripped and examined by 31 PNMR for mono-substituted pyrophosphate (31 P NMR D2O (no reference) 1HNMR (D2O) δ 7.3 (m, 5 H), 4.8 (d, 2H)

Example 8

Synthesis of 2-(N-(3-methylimidazolium))-ethyl pyrophosphate (25) (FIG. 31). 4.1 grams, 50 mmol, of methylimidazole (22) and 18.5 grams, 50 mmol, of ethylene di(p-toluenesulfonate) (23) were heated together for 24 hrs at 70° C. in 50 mL of dry acetonitrile, generating a white precipitate. The suspension was filtered, and the filtrate dried under reduced pressure. The residue was triturated with about 30 ml of methanol, the methanol solution being collected, evaporated to dryness, and crystallized from 30 ml of ethyl acetate. After filtration and vacuum drying, 6.4 grams, of solid white (24) was isolated. 1H NMR (DMSOd6) δ 9.06 (s, 1H), 7.68 (d, 2H), 7.61 (t, 2H), 7.48 (d, 2H), 7.46 (d, 2H), 7.11 (d, 2H) 4.47 (t, 2H), 4.41 (t, 2H) 3.81 (s, 3H) 2.42 (s, 3H), 2.18 (s, 3H).

14.4 grams of tris(tetrabutylammonium)pyrophosphate of (18) were dissolved in 5 mL of acetonitrile and all 6.4 grams of the solid (24) was added. After 30 minutes the reaction was diluted into 100 mL of water and loaded on a Dowex 1X8 200 equilibrated with TEAB and eluted with a TEAB gradient. The fractions were analyzed for phosphate using the procedure shown in Example 6. A sample from each of these fractions was stripped and examined by 31 PNMR for mono-substituted pyrophosphate. 1HNMR (D2O) δ 8.7 (s, 1H), 7.38 (t, 1H), 7.27 (t, 1H), 4.3 (t, 2 H), 4.09 (m, 2H), 3.74 (s, 3H), 3.1 (q, 6 H), 1.2 (t, 9 H).

Example 9

Synthesis of γ-methyl-dUTP (26) (FIG. 32). Tri-n-butylamine (2.2 μL, 9.3 μmol) was added to a dimethylformamide (DMF) solution (0.2 mL) of methyl pyrophosphate (19) (1.2 mg, 5 μmol from Example 2) that was previously co-evaporated two times with anhydrous DMF (0.2 mL). Carbonyldiimidazole (CDI, 4 mg, 25 μmol) was added and the mixture was stirred at room temperature overnight. Excess CDI was destroyed by addition of MeOH (2.2 μL) and stirring for 30 minutes. To the resulting mixture was added (19) from Example 6 (0.5 μmol in 0.1 mL DMF), which was stirred at room temperature for 3 days. After concentration at reduced vacuum, the residue was purified on anion exchange HPLC with an acetonitrile/TEAB gradient. The fractions containing (26) were combined and further purified by reverse phase HPLC: M/S: M−1=779.2 (calc. 779.0)

Example 10

Synthesis of γ-benzyl-dATP (27) (FIG. 33). This compound was assembled and purified in a similar manner compared to Example 9, using pyrophosphate (27) from Example 7 and dAMP (14) from Example 4.

Example 11

Synthesis of γ-(2-(N-(3-methylimidazolium))-ethyl)-dCTP (28) (FIG. 34). This compound was assembled and purified in a similar manner compared to Example 9, using pyrophosphate (25) from Example 8 and dCMP (12) from Example 3.

Example 12

Synthesis of γ-(2-(N-(3-methylimidazolium))-ethyl)-dGTP (29) (FIG. 35). This compound was assembled and purified in a similar manner compared to Example 9, using pyrophosphate (25) from Example 8 and dGMP (16) from Example 5.

Example 13

General procedure for evaluation of termination properties of γ-substituted-dNTP's comprising silver ion cleavable linker arms attached to the base. All evaluations performed with Therminator (NEB) DNA polymerases were 3' to 5' exonuclease negative. Three types of templates were used in testing each substrate, where N denotes the complement of the base that is being evaluated for its termination properties, and the underlined portion of the target is the priming site: 1) a single correct base immediately after the priming site followed by incorrect bases; 2) two correct bases immediately after the priming site followed by incorrect bases; 3) each incorrect base followed by the correct base and then additional incorrect bases. The first two primers were used to show incorporation and termination, while the third set of templates was used to study mis-incorporation. All substrates were evaluated by capillary electrophoresis with analysis for extension of 0, 1, or 2 bases from a fluorescein labeled −21 M13 primer (the binding site of the primer corresponds to the underlined portion of the templates shown below).

```
                                            [SEQ ID NO: 7]
1. (BIO-TEG)(C18)(C18)CCCCCCGTGTGTGCTTNACTGGCCGTCG
   TTTTACA

[SEQ ID NO: 8]
2. (BIO-TEG)(C18)(C18)CCCCCCGTGTGTGCTNNACTGGCCGTCG
   TTTTACA

[SEQ ID NO: 9]
3. (BIO-TEG)(C18)(C18)CCCCCCGTGTGTGCTNTACTGGCCGTCG
   TTTTACA

[SEQ ID NO: 10]
   (BIO-TEG)(C18)(C18)CCCCCCGTGTGTGCTNCACTGGCCGTCG
   TTTTACA

[SEQ ID NO: 11]
   (BIO-TEG)(C18)(C18)CCCCCCGTGTGTGCTNGACTGGCCGTCG
   TTTTACA:

[SEQ ID NO: 12]
   (BIO-TEG)(C18)(C18)CCCCCCGTGTGTGCTNAACTGGCCGTCG
   TTTTACA:
```

Templates were pre-hybridized to the primer at 2 μM final concentration. The final assay concentration of the primer/template hybrid was 40 nM.

Unless otherwise noted, substrates were tested at 1 μM final concentration with 1 μL of the appropriate commercial enzyme at the concentration supplied by the manufacturer (usually 2-5 U/μL in 2× buffer composed of 40 mM Tris, pH 7.6, 10 mM DTT, 10 mM $Mg_2SO_4$ and 30 mM isocitrate). Each buffer was used at 1× in the final assay.

Generally, assays were set up as 10 μL final volume and run at 65° C. The termination properties were evaluated at 10 minutes, 30 minutes and 1 hr. At the end of each reaction, 4 mL of the reaction mix was pipetted into 25 μL of 0.5 M EDTA, to quench the reaction, in a streptavidin coated microtiter plate well (Applied Biosystems Part No. 4357279) to capture the biotin labeled template for purification of the primer. Plates were shaken at room temperature for 10 minutes. Excess fluid was discarded and the microtiter wells were washed 3× with 4×SSC containing 0.1% Tween 20. Plates were centrifuged briefly upside down to remove excess buffer. To remove the primer from the template, 20 μL of HiDi Formamide (Applied Biosystems Part No. 4311320) was added with size ladder (LIZ® dye-labeled SNPlex™ internal size standard) to each well. The plate was incubated at 50° C. with shaking for 10 minutes. 10 mL of the HiDi Formamide solution was transferred to a 96 well plate (Applied Biosystems Part No. N8010560) and covered with a 96 well plate septa (Applied Biosystems Part No. 4315933). Samples were separated electrophoretically on an AB 3100XL with a 36 cm capillary with POP6™ polymer separating media. The peaks were analyzed with either GeneScan® Software or Peak Scanner™ software, both from Applied Biosystems.

Example 14

Termination and mis-incorporation properties of γ-methyl-dUTP (26). The substrate from Example 9 was evaluated following the procedure of Example 13, using the following templates.

[SEQ ID NO: 13]
1. (BIO-TEG)(C18)(C18)CCCCCCGTGTGTGCTTAACTGGCCGTCG TTTTACA

[SEQ ID NO: 4]
2. (BIO-TEG)(C18)(C18)CCCCCCGTGTGTGCTAAACTGGCCGTCG TTTTACA

[SEQ ID NO: 14]
3. (BIO-TEG)(C18)(C18)CCCCCCGTGTGTGCTATACTGGCCGTCG TTTTACA

[SEQ ID NO: 15]
(BIO-TEG)(C18)(C18)CCCCCCGTGTGTGCTAGACTGGCCGTCG TTTTACA

Figure 21:
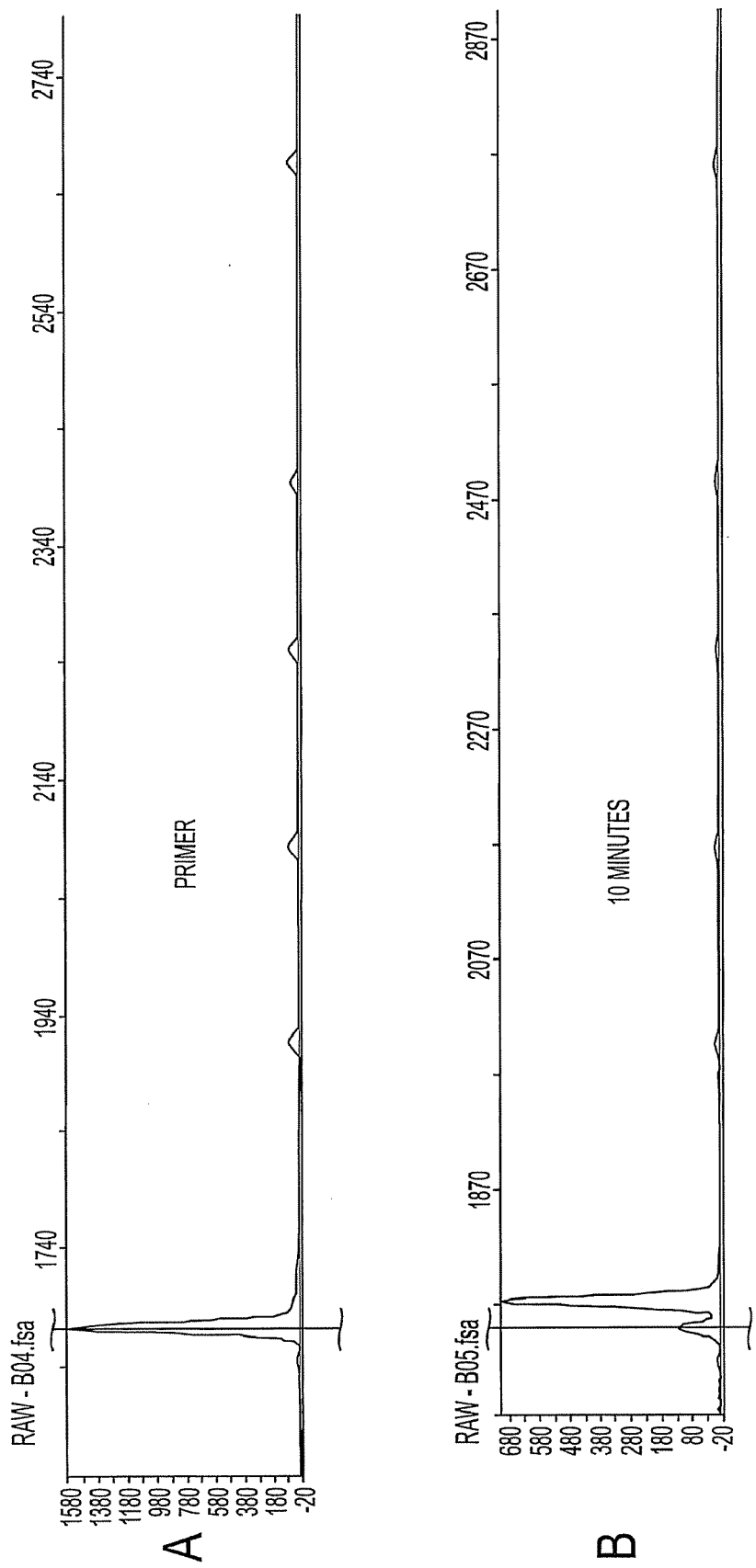
Figure 21:
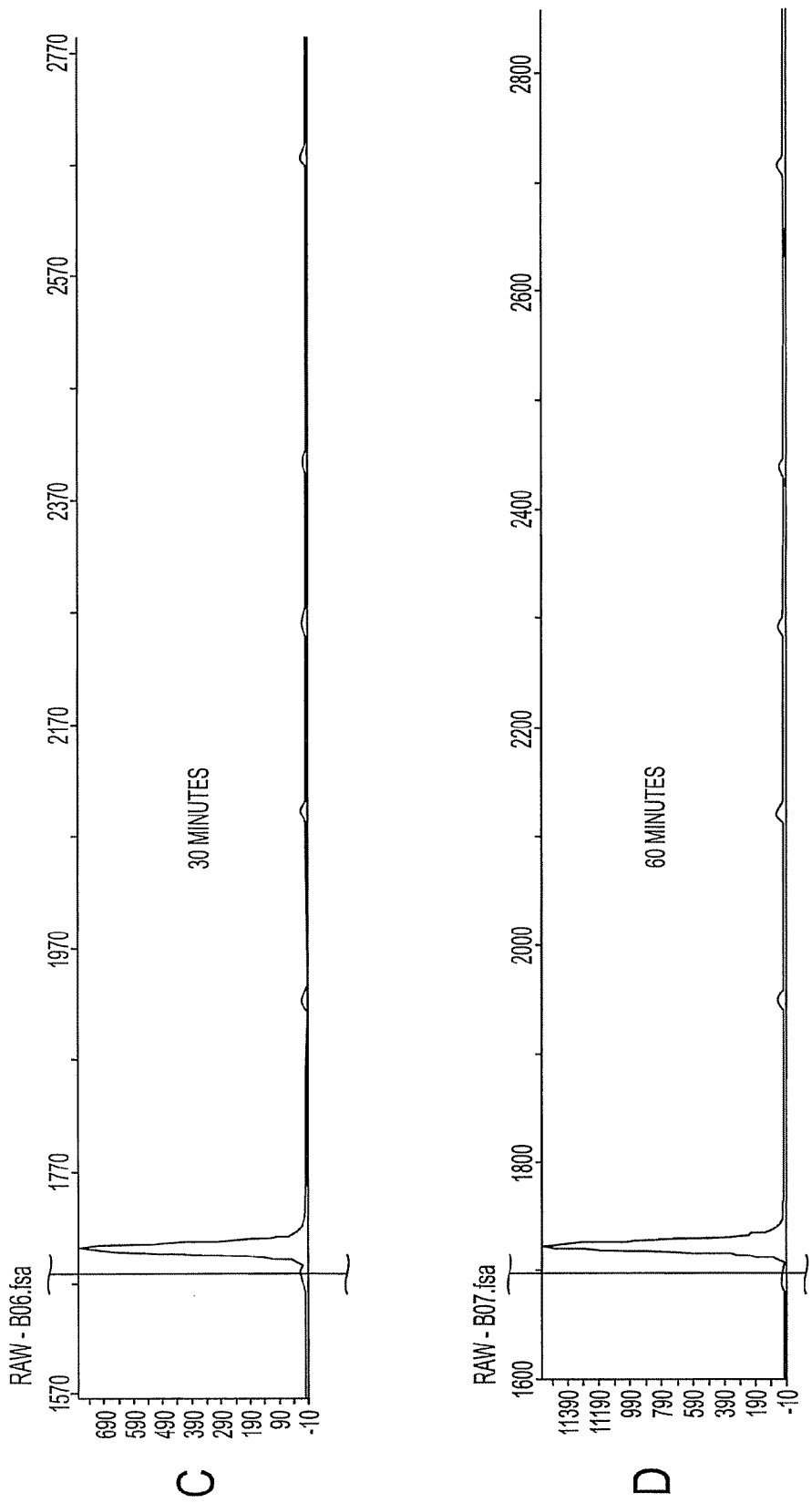
Figure 22:
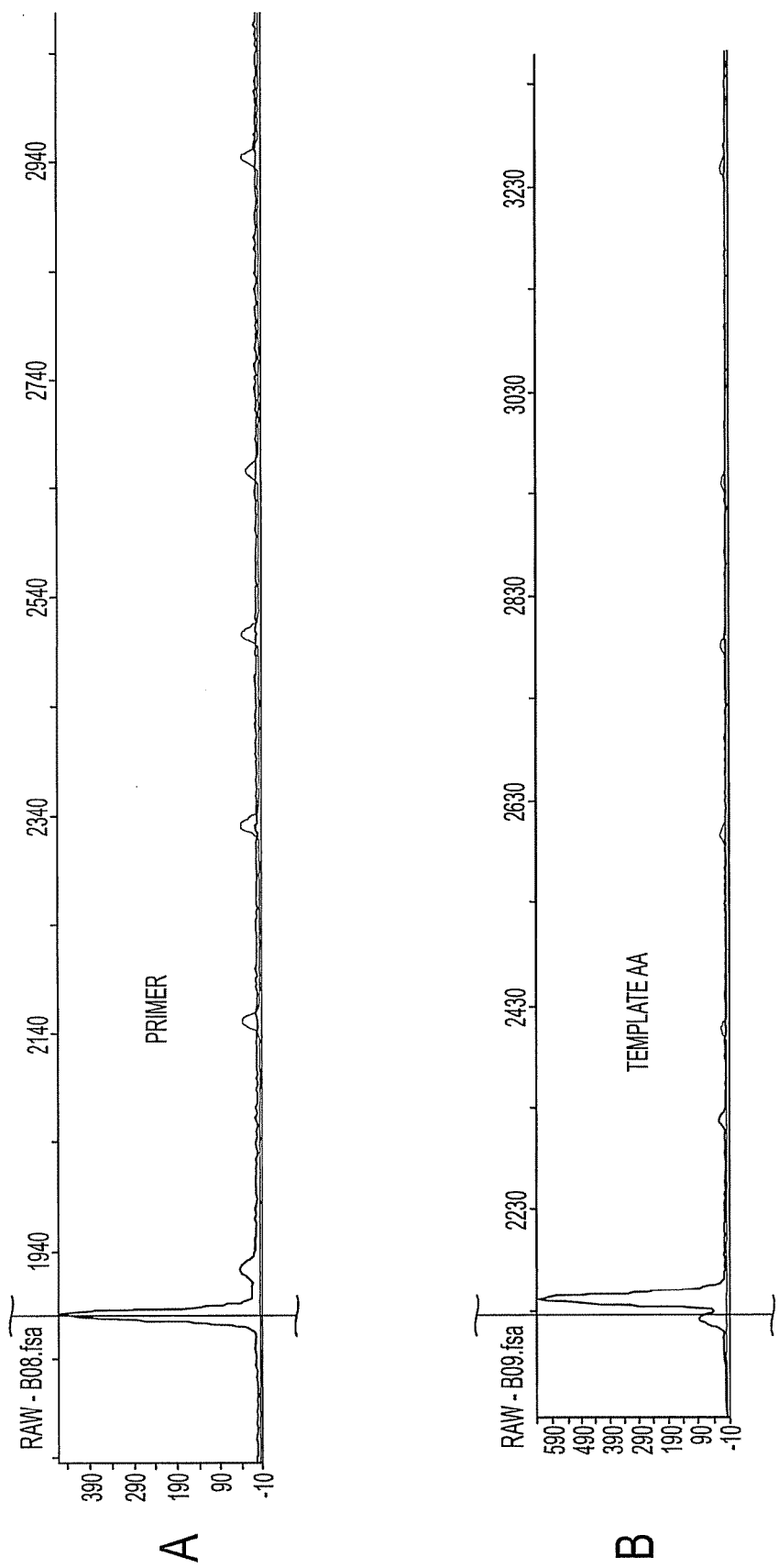
Figure 22:
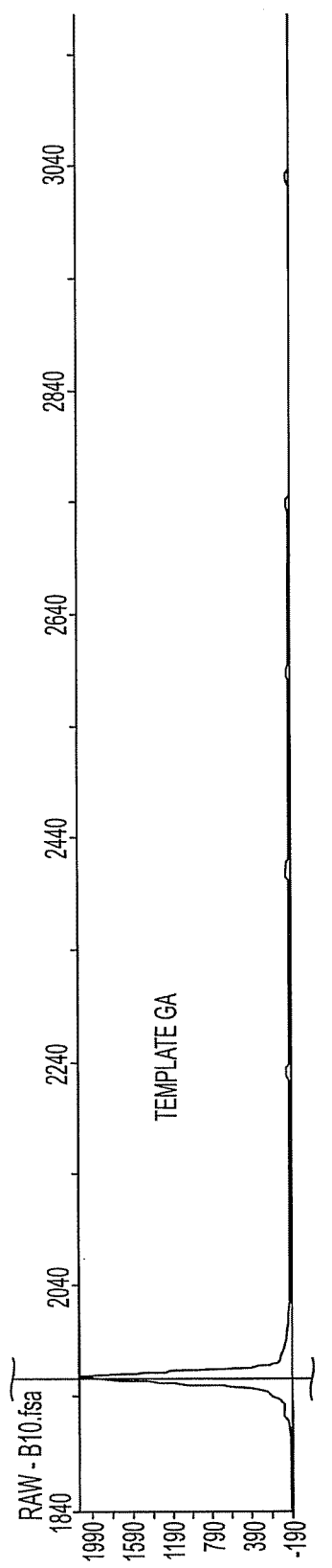
Figure 22:
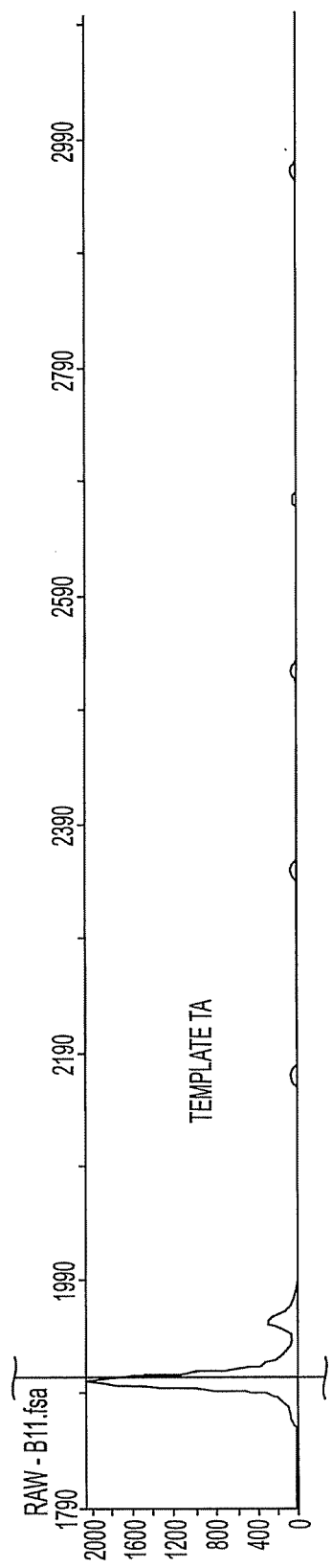

Termination properties are shown in FIG. 21 and mis-incorporation properties are shown in FIG. 22. FIG. 21 shows almost complete consumption of the primer after 10 minutes. No further incorporation is observed over the $2^{nd}$ A of template 2 after 60-minutes, indicating excellent termination properties.

Example 15

Termination and mis-incorporation properties of γ-benzyl-dATP (27). The substrate from Example 10 was evaluated following the procedure of Example 13, using the following templates.

[SEQ ID NO: 14]
1. (BIO-TEG)(C18)(C18)CCCCCCGTGTGTGCTATACTGGCCGTCG TTTTACA

[SEQ ID NO: 16]
2. (BIO-TEG)(C18)(C18)CCCCCCGTGTGTGCTTTACTGGCCGTCG TTTTACA

[SEQ ID NO: 13]
3. (BIO-TEG)(C18)(C18)CCCCCCGTGTGTGCTTAACTGGCCGTCG TTTTACA

[SEQ ID NO: 17]
(BIO-TEG)(C18)(C18)CCCCCCGTGTGTGCTTGACTGGCCGTCG TTTTACA

[SEQ ID NO: 18]
(BIO-TEG)(C18)(C18)CCCCCCGTGTGTGCTTCACTGGCCGTCG TTTTACAZ

Termination and mis-incorporation properties are shown in FIG. 36. FIG. 36 shows almost complete consumption of the primer after 10 minutes; no further incorporation is observed over the $2^{nd}$ T of template 2 after 60 minutes, indicating excellent termination properties.

Example 16

Termination and mis-incorporation properties of γ-imidazolium-dCTP (28). The substrate from Example 11 was evaluated following the procedure of example 13, using the following templates.

[SEQ ID NO: 19]
1. (BIO-TEG)(C18)(C18)CCCCCCGTGTGTGCTCGACTGGCCGTCG TTTTACA

[SEQ ID NO: 20]
2. (BIO-TEG)(C18)(C18)CCCCCCGTGTGTGCTGGACTGGCCGTCG TTTTACA

[SEQ ID NO: 21]
3. (BIO-TEG)(C18)(C18)CCCCCCGTGTGTGCTGAACTGGCCGTCG TTTTACA

[SEQ ID NO: 22]
(BIO-TEG)(C18)(C18)CCCCCCGTGTGTGCTGTACTGGCCGTCG TTTTACA

[SEQ ID NO: 23]
(BIO-TEG)(C18)(C18)CCCCCCGTGTGTGCTGCACTGGCCGTCG TTTTACA

Termination and mis-incorporation properties at 1 μM [(28)] are shown in FIG. 37. As can be seen from FIG. 37, the activity of (28) is quite low, significant incorporation of (28) is observed after 1 hr. and no mis-incorporation is observed after 1 hr. Termination properties of (28) at higher concentrations are shown in FIG. 38. As can be seen from FIG. 38, at 5 μM [(28)] the primer is completely consumed after 30 minutes, with only a trace of extension past the first base on the GG template.

Example 17

Termination and mis-incorporation properties of γ-imidazolium-dGTP (29). The substrate from Example 12 was evaluated following the procedure of Example 13, using the following templates.

[SEQ ID NO: 23]
1. (BIO-TEG)(C18)(C18)CCCCCCGTGTGTGCTGCACTGGCCGTCG TTTTACA

[SEQ ID NO: 24]
2. (BIO-TEG)(C18)(C18)CCCCCCGTGTGTGCTCCACTGGCCGTCG TTTTACA

[SEQ ID NO: 25]
3. (BIO-TEG)(C18)(C18)CCCCCCGTGTGTGCTCAACTGGCCGTCG TTTTACA

[SEQ ID NO: 19]
(BIO-TEG)(C18)(C18)CCCCCCGTGTGTGCTCGACTGGCCGTCG TTTTACA

[SEQ ID NO: 26]
(BIO-TEG)(C18)(C18)CCCCCCGTGTGTGCTCTACTGGCCGTCG TTTTACA

Termination and mis-incorporation properties at 1 μM [(29)] are shown in FIG. 39. As can be seen from FIG. 39, the activity of (29) is quite low, significant incorporation of (29) is observed only after 1 hr. and no mis-incorporation is observed after 1 hr. Termination properties of (29) at higher concentrations are shown in FIG. 40. As can be seen from FIG. 40, at 4 μM [(29)] the primer is completely consumed after 1 hr., with only a trace of extension past the first base on the CC template.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A compound having a structure of formula (I) or formula (II):

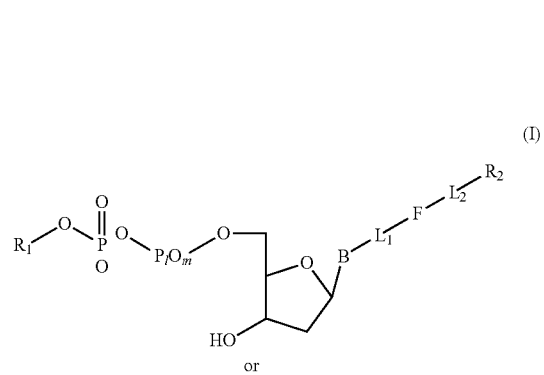

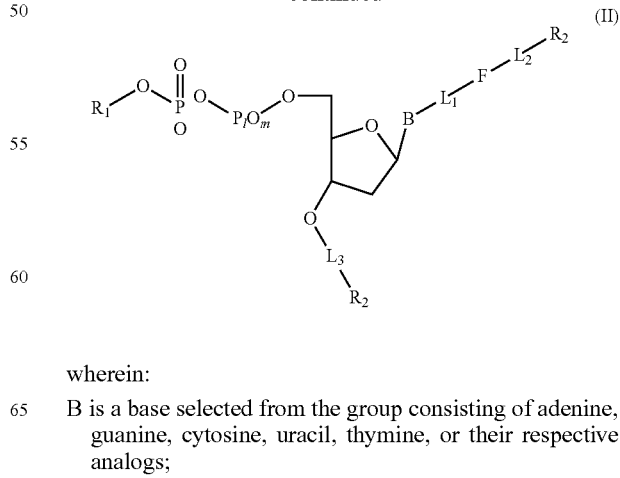

wherein:

B is a base selected from the group consisting of adenine, guanine, cytosine, uracil, thymine, or their respective analogs;

L₁ is a group that forms a linkage between the base B and F;

F is a heteroatom that forms a linkage between L₁ and L₂;

L₂ is a chemically labile group with respect to its attachment to F and forms a chemical linkage to R₂;

L₃ is a chemically labile group comprising a heteroatom and forms a chemical linkage to R₂;

R₂ is a group comprising a reporter;

R₁ is a group that suppresses the template directed polymerase incorporation rate of the nucleoside triphosphate onto the 3' end of an extending oligonucleotide prior to cleavage of L₂-R₂ from the previous incorporation event;

L₂-R₂ prevents the template directed polymerase incorporation of the compound of the formula (I) onto the 3' end of an extending oligonucleotide onto which a compound of the formula (I) has been incorporated;

l is an integer; and m=3l−1.

2. The compound of claim 1 where $R_1$ is an organic substituent selected from the group consisting of neutral forms of substituted or un-substituted alkyls, substituted or un-substituted aromatics, substituted or un-substituted heterocycles, substituted or un-substituted aromatic heterocycles, or anionic or cationic forms thereof.

3. The compound of claim 2, wherein cleavage of the chemically labile group $L_2$ leaves a linker residue moiety attached to the base having a terminal group F.

4. The compound of claim 3, wherein the terminal group F is not an amino group.

5. The compound of claim 3, wherein the terminal group F is an hydroxyl group.

6. The compound of claim 1, wherein l is 2 or 3.

7. The compound of claim 1, wherein the compound has a structure represented by the following formula (II):

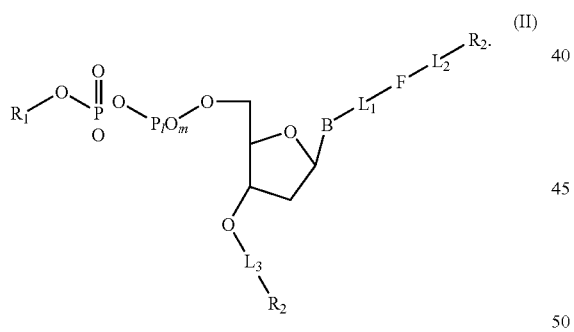

8. The compound of claim 1, wherein $L_2$ comprises a chemically labile group selected from the group consisting of: —C(O)—S—; —C(O)O—; —CH—(SCH₃)-Ph- and [RO]₂P(O)S—; wherein Ph is a substituted phenyl group or a substituted aromatic ring; and wherein $R_1$ is an organic substituent selected from the group consisting of neutral forms of substituted or un-substituted alkyls, substituted or un-substituted aromatics, substituted or un-substituted heterocycles, substituted or un-substituted aromatic heterocycles, or anionic or cationic forms thereof.

9. The compound of claim 2, wherein $L_1$ forms a permanent linkage between the base and the heteroatom F, and $L_2$ forms a transient linkage between the heteroatom F and $R_2$.

10. The compound of claim 9, wherein the heteroatom is O, S, or N.

11. The compound of claim 9, wherein $L_1$ comprises a moiety represented by the formula:

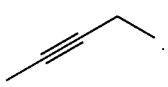

12. The compound of claim 9, wherein $L_1$ comprises a moiety represented by the formula:

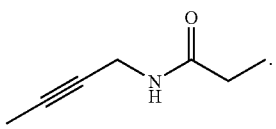

13. The compound of claim 9, wherein $L_2$-$R_2$ comprises a moiety represented by the formula:

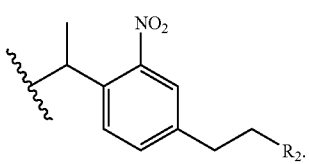

14. The compound of claim 1, wherein the compound has a structure represented by the following formula (VI):

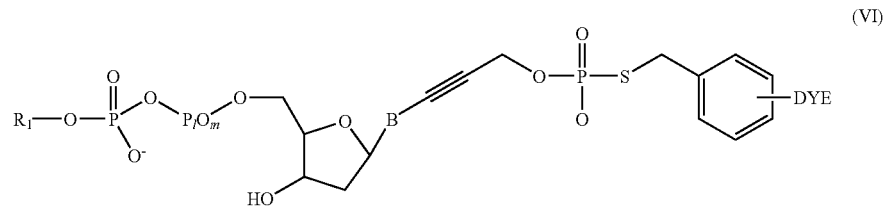

wherein "Dye" represents the reporter.

15. The compound of claim 1, wherein the chemically labile group $L_2$ is cleavable by Ag⁺ between the dye and the base ₂.

16. The compound of claim 1, wherein F-L$_2$ comprises a moiety selected from the group consisting of:

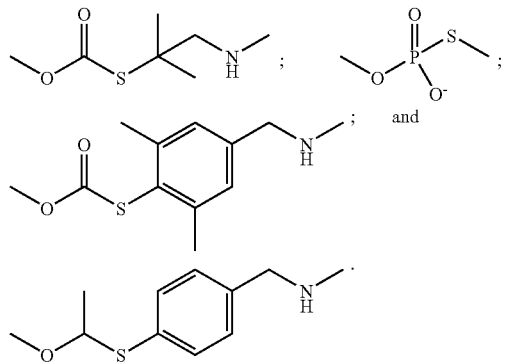

17. The compound of claim 1, wherein L$_2$ comprises a moiety of the following formula:

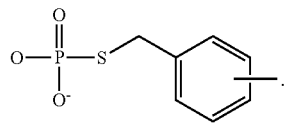

18. The compound of claim 1, wherein R$_1$ is a group that suppresses the template directed polymerase incorporation rate of the nucleoside triphosphate onto the 3' end of an extending oligonucleotide prior to cleavage of L$_2$-R$_2$ from the previous incorporation event.

19. The compound of claim 18, wherein R$_1$ is a reporter or quencher.

20. The compound of claim 1, wherein the compound has a structure represented by the following formula (VI):

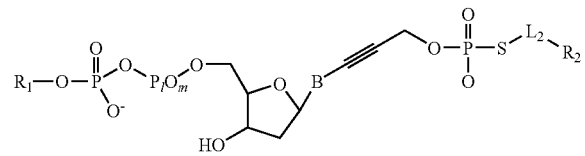

wherein R$_1$ is not H.

21. The compound of claim 20, wherein R$_1$
is an organic substituent selected from the group consisting of neutral forms of substituted or un-substituted alkyls, substituted or un-substituted aromatics, substituted or un-substituted heterocycles, substituted or un-substituted aromatic heterocycles, or anionic or cationic forms thereof.

22. The compound of claim 7, wherein R$_1$ is not H.

23. The compound of claim 22, wherein R$_1$ is an organic substituent selected from the group consisting of neutral forms of substituted or un-substituted alkyls, substituted or un-substituted aromatics, substituted or un-substituted heterocycles, substituted or un-substituted aromatic heterocycles, or anionic or cationic forms thereof.

24. The compound of claim 1, wherein the compound has a structure of formula (I):

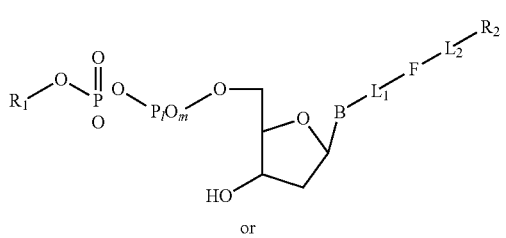

or

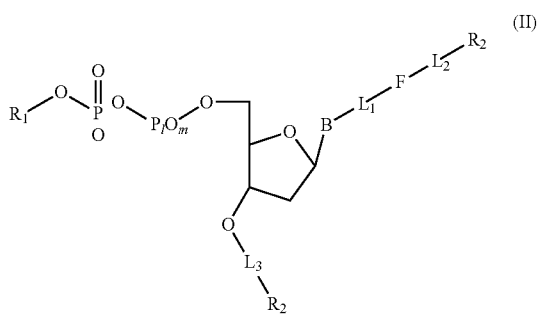

25. The compound of claim 17, wherein the L$_2$ benzene group to which R$_2$ is attached is further substituted.

* * * * *